US012758644B2

(12) United States Patent
Urello et al.

(10) Patent No.: US 12,758,644 B2

(45) **Date of Patent: *Oct. 13, 2026**

(54) PEPTIDE DENDRONS AND METHODS OF USE THEREOF

(71) Applicant: ASTRAZENECA AB, Sodertalje (SE)

(72) Inventors: Morgan Audrey Urello, Gaithersburg, MD (US); Ronald James Christie, Gaithersburg, MD (US); Hannah Vaughan, Gaithersburg, MD (US)

(73) Assignee: ASTRAZENECA AB, Sodertalje (SE)

(*) Notice: Subject to any disclaimer, the term of this patent is extended or adjusted under 35 U.S.C. 154(b) by 223 days.

This patent is subject to a terminal disclaimer.

(21) Appl. No.: 18/698,811

(22) PCT Filed: Oct. 7, 2022

(86) PCT No.: PCT/IB2022/059608

§ 371 (c)(1),
(2) Date: Apr. 5, 2024

(87) PCT Pub. No.: WO2023/057975

PCT Pub. Date: Apr. 13, 2023

(65) Prior Publication Data

US 2024/0408220 A1 Dec. 12, 2024

Related U.S. Application Data

(60) Provisional application No. 63/262,269, filed on Oct. 8, 2021.

(51) Int. Cl.

| | |
|---|---|
| ***A61P 35/00*** | (2006.01) |
| ***A61K 47/18*** | (2017.01) |
| ***A61K 47/54*** | (2017.01) |
| ***A61K 47/64*** | (2017.01) |
| ***A61K 47/69*** | (2017.01) |

(52) U.S. Cl.

CPC ........ *A61K 47/6455* (2017.08); *A61K 47/183* (2013.01); *A61K 47/543* (2017.08); *A61K 47/6929* (2017.08); *A61P 35/00* (2018.01)

(58) Field of Classification Search

CPC .............. A61K 47/6455; A61K 47/183; A61K 47/543; A61K 47/6929; A61K 47/554; A61P 35/00; A61P 31/16

See application file for complete search history.

(56) References Cited

U.S. PATENT DOCUMENTS

| | | | | |
|---|---|---|---|---|
| 2013/0345284 A1 | 12/2013 | Lu et al. | | |
| 2014/0288150 A1* | 9/2014 | Guan | ..................... | C08G 75/14 435/375 |

FOREIGN PATENT DOCUMENTS

| | | |
|---|---|---|
| WO | 2008121153 A2 | 10/2008 |
| WO | 2011116152 A2 | 9/2011 |
| WO | 2021023891 A1 | 2/2021 |
| WO | 2022075459 A1 | 4/2022 |
| WO | 2022212838 A1 | 10/2022 |

OTHER PUBLICATIONS

National Center for Biotechnology Information (2026). PubChem Compound Summary for CID 67831919, (2S)-2-amino-6-(morpholine-4-carbonylamino)hexanoic acid. Retrieved Jan. 28, 2026 from https://pubchem.ncbi.nlm.nih.gov/compound/67831919. (Year: 2026).*

Arnida A., et al., "Novel Ternary Polyplex of Triblock Copolymer, pDNA and Anionic Dendrimer Phthalocyanine for Photochemical Enhancement of Transgene Expression", Journal of Controlled Release, vol. 116, No. 2, Nov. 28, 2006, pp. e75-e77, XP024957751, Issn: 0168-3659, DOI: 10.1016/J.JCONREL.2006.09.058, the whole document.

Deriu M.A., et al., "Elucidating the Role of Surface Chemistry on Cationic Phosphorus Dendrimer-siRNA Complexation", Nanoscale, vol. 10, No. 23, 2018, pp. 1-22, XP093020365, Issn: 2040-3364, DOI: 10.1039/ C8NR01928B, abstract figures p. 10960, left-hand column, paragraph Conclusions.

Fukushima S., et al., "PEGylated Polyplex Micelles from Triblock Catiomers with Spatially Ordered Layering of Condensed pDNA and Buffering Units for Enhanced Intracellular Gene Delivery", Journal of the American Chemical Society, vol. 127, No. 9, Mar. 9, 2005, pp. 2810-2811, XP093020246, ISSN: 0002-7863, DOI: 10.1021/ja0440506, the whole document.

Guo L., et al., "Morpholino-terminated Dendrimer Shows Enhanced Tumor pH-triggered Cellular Uptake, Prolonged Circulation Time, and Low Cytotoxicity", Polymer, vol. 84, Jan. 2, 2016, pp. 189-197, XP029406685, ISSN: 0032-3861, Doi: 10.1016/J.POLYMER.2015.12.056, abstract figures, table 1.

International Search Report and Written Opinion for International Application No. PCT/IB2022/059608, mailed Feb. 16, 2023, 17 Pages.

(Continued)

*Primary Examiner* — Lianko G Garyu
*Assistant Examiner* — Claudia Espinosa
(74) *Attorney, Agent, or Firm* — Global IP ASTRAZENECA

(57) ABSTRACT

The specification relates to peptide dendrons comprising one or more residues derived from a modified lysine of formula (I), pharmaceutical delivery systems comprising these peptide dendrons, pharmaceutical compositions containing them, and to their use in therapy.

(I)

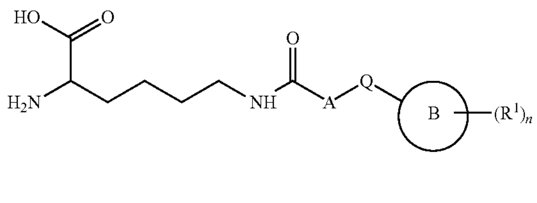

14 Claims, 19 Drawing Sheets

Specification includes a Sequence Listing.

(56) References Cited

OTHER PUBLICATIONS

Padie C., et al., "Polycationic Phosphorus Dendrimers: Synthesis, Characterization, Study of Cytotoxicity, Complexation of DNA, and Transfection Experiments", New Journal of Chemistry, vol. 33, No. 2, 2009, pp. 318-326, XP055422695, ISSN: 1144-0546, DOI: 10.1039/B815259D, abstract, p. 319 figures.

Xiong Z., et al., "Zwitterion-functionalized Dendrimer-entrapped Gold Nanoparticles for Serum-enhanced Gene Delivery to Inhibit Cancer Cell Metastasis", Acta Biomaterialia, vol. 99, Sep. 9, 2019, pp. 1-10, XP085897108, ISSN: 1742-7061, DOI: 10.1016/J.ACTBIO.2019.09.005, abstract figures.

Zeng H., et al., "Structure-Based Design of Dendritic Peptide Bolaamphiphiles for siRNA Delivery", ACS Central Science, vol. 1, No. 6, Sep. 23, 2015, pp. 303-312, XP055374816, ISSN: 2374-7943, DOI: 10.1021/acscentsci.5b00233, abstract, p. 304 figures.

* cited by examiner

Figure 1
Fmoc-GV{Cit}GGSC-
(1) 20% Piperidine in DMF
(2) Fmoc-K(Fmoc)
(3) 20% Piperidine in DMF
NH2–KGV{Cit}GGSC-
NH2
(1) Fmoc-K(Fmoc)K(modified)LR
(2) 20% Piperidine in DMF
NH2–KK(modified)LR-KGV{Cit}GGSC-
RLK(modified)K–NH2
(1) Fmoc-K(Fmoc)K(modified)LR
(2) 20% Piperidine in DMF
NH2–KK(modified)LR-KK(modified)LR–KGV{Cit}GGSC-
RLK(modified) K–RLK(modified) K–NH2
RLK(modified)K–NH2
(1) Fmoc-K(modified)LR
(2) 20% Piperidine in DMF
K(modified)LR–KK(modified)LR–KK(modified)LR–KGV{Cit}GGSC-
RLK(modified) K–RLK(modified) K–RLK(modified)
RLK(modified) K–RLK(modified)
RLK(modified)

Fold Improvement over Non-Targeted with PEG-PD3(MN)

| Target | H1299 | C2C12 | CT26 STK11 KO |
|---|---|---|---|
| TfR Peptide | 2.64 | 3.54 | N/A |
| cRGD | 1.56 | 2.10 | 3.1 |

PEPTIDE DENDRONS AND METHODS OF USE THEREOF

CROSS-REFERENCE TO RELATED APPLICATION

This application claims the benefit of priority to U.S. Provisional Application No. 63/262,269, filed on Oct. 8, 2021, which is incorporated by reference herein in its entirety for all purposes.

FIELD

The present specification relates to peptide dendrons comprising one or more residues derived from a modified lysine, and the use of these peptide dendrons for delivering pharmaceutically active agents, particularly genetic material, into a cell. The present specification further relates to the use of these peptide dendrons in therapy.

BACKGROUND

Gene therapy is the medical field that focuses on the therapeutic delivery of (foreign) genetic material (such and DNA and RNA) into a patient's cells in order to treat a disease. To date, several gene therapies including Luxturna® (RPE65 mutation-induced blindness) and Kymriah® (chimeric antigen receptor T cell therapy) have received regulatory approval for a number of different medical conditions.

Gene delivery is the process used to introduce the genetic material into a cell. To be successful, the genetic material must remain stable during transport and ultimately be internalized into the targeted cell. When the genetic material is DNA, it must be internalized into the targeted cell and delivered into the nucleus. Gene delivery requires a vector, and suitable vectors generally fall into two categories: viral, and non-viral.

Virus mediated gene delivery utilizes the ability of a virus to inject its DNA inside a host cell. The genetic material is packaged into a replication-deficient viral particle in order to form a viral vector. Viral methods are highly efficient but can induce an immune response. Furthermore, they can only deliver very small pieces of genetic material into the cells, producing them is labour-intensive, and there are risks of random insertion sites, cytopathic effects and mutagenesis.

Synthetic vectors offer several advantages over viruses for gene delivery applications in regard to structural versatility and scalability; and they may be designed solely and specifically to achieve one desired purpose. These materials can be designed to package the genetic material into nanoparticles or vesicles which have been engineered to overcome biological barriers associated with cell uptake, transport into the cytosol, and (if desired) delivery into the nucleus. A common approach is to package the genetic material into multimolecular assemblies with materials such as polymers, peptides, or lipids comprising positive charges which associate with the anionic nucleic acids. Electrostatic interactions between the positive and negative charges drive self-assembly into nano- or microparticle structures, and the size and shape of these particles can be controlled by material type and condensation conditions (Park et al. Adv Drug Del Rev, 2006, 58 (4): 467-86).

Formulation of DNA, for example, into a suitable vector like a nanoparticle significantly improves cellular uptake of DNA when compared to uptake of unformulated DNA. DNA is too large and negatively charged to internalize into cells (which also have a net negative charge) on its own by passive processes such as diffusion across the cell membrane. Unformulated DNA also tends to trigger an immune response which leads to its degradation. Formulation of the DNA into a suitable vector can neutralize its negative charge and protect it from degradation in the extracellular space.

In order for the vector to be effectively internalised, it must be transported into the cell via a process called endocytosis. During this process, the vector is surrounded by an area of cell membrane, which then buds off inside the cell to form an endosome. The vector must be designed to allow this process to occur, but then mitigate the possibility of lysosome entrapment, i.e. sequestration into the acidic membrane-bound lysosome compartments. One way of achieving this is to ensure the endosome ruptures before lysosomal trafficking can occur. This may be achieved by the vector buffering the endosome pH (the endosome becomes increasingly acidic after cell uptake) until the resulting osmotic gradient causes the endosome to burst and release the genetic material into the cytoplasm where it can be available for transcription/translation. Suitable vector materials with efficient buffering capacity over the endosomal buffering range (pH 7.4-pH 5.0) can slow the acidification of the endosome by accepting protons, which causes an influx of further protons and counter ions from the cytosol.

Current synthetic gene delivery systems are limited in vivo by low stability, high toxicity, and inefficient cytoplasmic entry of the genetic material. Engineering a multi-functional material suitable for gene delivery that achieves an optimal balance between formulation properties (size, charge, etc.), stability, buffering capacity, and toxicity, whilst maintaining a high delivery efficiency has proved difficult and complex, but would significantly simplify the resulting formulation.

Peptide dendrons (PDs) are 3-dimensional structures comprising amino acid residues, wherein the side chain of one of the residues, e.g. the ε-amine of a lysine, is utilised to form branches or generations, building up the molecule into a 3-D macromolecule. Peptide dendrons are typically produced using solid-phase peptide synthesis allowing for precise control of amino acid residue sequence and geometry within a well-defined structure. Final products are monodisperse, with highly tailorable properties (i.e. hydrophobicity, charge density, and molecular weight) allowing for multi-functional optimization and flexible application.

Peptide dendrons have been widely explored, but production costs and low proteolytic stability have hindered clinical success. Kwok et al (ACS Nano, 2013 May 28; 7 (5): 4668-82, doi: 10.1021/nn400343z and ChemBioChem, 2016, 17 (23), 2223-2229) explored peptide dendrimer/lipid hybrid systems as DNA and RNA transfection reagents, but were limited to dipeptide branches by synthesis limitations, limiting material functionality and in vivo efficacy.

The present application describes certain peptide dendrons comprising one or more residues derived from a modified lysine. These peptide dendrons i) possess enhanced buffering properties tuned to enable protonation during the pH transition that occurs during cellular internalization and lysosomal trafficking, ii) are more stable due to increased nucleic acid binding through electrostatic and non-electrostatic (e.g. pi-pi stacking) interactions, iii) have increased biocompatibility when metabolite-based core units are used which are naturally occurring and less likely to be toxic or immunogenic, and/or iv) achieve responsive nucleic acid release through specific intracellular enzymatic degradation (cathepsin-B). They form nanoparticles with multiple nucleic acid formats including plasmid DNAs, mRNAs, siRNAs and antisense oligonucleotide (ASOs) (~25-100 nm, spheres, rods, and toroids) and demonstrate higher serum stability and prolonged blood circulation following intravenous injection in mice without associated toxicity. They have demonstrated the capacity to deliver and/or co-deliver a wide range of nucleic acid formats including DNAs, mRNAs, siRNAs, and ASOs successfully, and protect the encapsulated genetic material by not disassociating easily until inside a cell. Furthermore, co-delivery of RNA/DNA within the same nanoparticle allows for control over protein expression kinetics, the expression of synergistic therapeutics, and expands nanoparticle application to fields where multiple components are required such as CRISPR.

SUMMARY

This specification describes, in part, a peptide dendron comprising one or more residues derived from a modified lysine of formula (I):

(I)

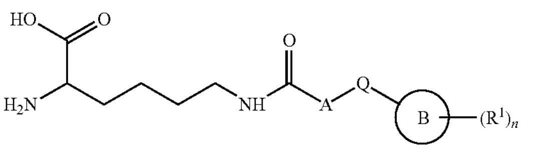

wherein:

A is a bond, $C_{1-6}$alkylene, carbocyclyl or heterocyclyl; wherein said carbocyclyl or heterocyclyl may be optionally substituted on carbon by one or more $R^2$; and wherein if said heterocyclyl contains an —NH— moiety that nitrogen may be optionally substituted by a group selected from $R^A$;

Q is a bond, carbocyclyl or heterocyclyl; wherein said carbocyclyl or heterocyclyl may be optionally substituted on carbon by one or more $R^3$; and wherein if said heterocyclyl contains an —NH— moiety that nitrogen may be optionally substituted by a group selected from $R^B$;

Ring B is morpholinyl or thiomorpholinyl; wherein if said morpholinyl or thiomorpholinyl contains an —NH— moiety that nitrogen may be optionally substituted by a group selected from $R^C$;

$R^1$, $R^2$ and $R^3$ are each independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl and N-methyl-N-ethylsulphamoyl;

n is 0-4;

$R^A$, $R^B$ are $R^C$ are independently selected from methyl, ethyl, propyl, isopropyl, acetyl, mesyl, ethylsulphonyl, methoxycarbonyl, ethoxycarbonyl, propoxycarbonyl, butoxycarbonyl, carbamoyl, N-methylcarbamoyl, N-ethylcarbamoyl, N,N-dimethylcarbamoyl, N,N-diethylcarbamoyl and N-methyl-N-ethylcarbamoyl.

This specification also describes, in part, a peptide dendron as described herein for use in delivering a pharmaceutically active agent into a cell.

This specification also describes, in part, a pharmaceutical composition which comprises one or more peptide dendrons as described herein and a pharmaceutically active agent.

This specification also describes, in part, a method of gene therapy which comprises administering to said animal an effective amount of a pharmaceutical composition as described herein.

DETAILED DESCRIPTION

Many embodiments are detailed throughout the specification and will be apparent to a reader skilled in the art. The disclosure is not to be interpreted as being limited to any of the recited embodiments.

"A" means "at least one". In any embodiment where "a" is used to denote a given material or element, "a" may mean one.

"Comprising" means that a given material or element may contain other materials or elements. In any embodiment where "comprising" is mentioned the given material or element may be formed of at least 1% w/w, at least 5% w/w, at least 10% w/w, at least 20% w/w, at least 30% w/w, or at least 40% w/w of the material or element. "Comprising" may also mean "consisting of" (or "consists of") or "consisting essentially of" (or "consists essentially of") a given material or element.

"Consisting of" or "consists of" means that a given material or element is formed entirely of the material or element. In any embodiment where "consisting of" or "consists of" is mentioned the given material or element may be formed of 100% w/w of the material or element.

"Consisting essentially of" or "consists essentially of" means that a given material or element consists almost entirely of that material or element. In any embodiment where "consisting essentially of" or "consists essentially of" is mentioned the given material or element may be formed of at least 50% w/w, at least 60% w/w, at least 70% w/w, at least 80% w/w, at least 90% w/w, at least 95% w/w or at least 99% w/w of the material or element.

In any embodiment where "is" or "may be" is used to define a material or element, "is" or "may be" may mean the material or element "consists of" or "consists essentially of" the material or element.

In any embodiment of this specification where "about" is mentioned, "about" may mean+/−0 (i.e. no variance), +/−0.01, +/−0.05, +/−0.1, +/−0.5, +/−1, +/−2, +/−5, +/−10 or +/−20 percent of the figure quoted. Where a figure is quoted, in a further embodiment this further refers to about the figure quoted.

Claims are embodiments.

Disclosed herein is a peptide dendron comprising one or more residues derived from a modified lysine of formula (I):

(I)

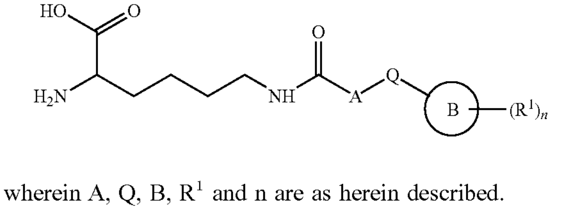

wherein A, Q, B, $R^1$ and n are as herein described.

In one embodiment A is a bond.

In one embodiment A is $C_{1-6}$alkylene.

In one embodiment A is methylene.

In one embodiment A is carbocyclyl; wherein said carbocyclyl may be optionally substituted on carbon by one or more $R^2$.

In one embodiment A is heterocyclyl; wherein said heterocyclyl may be optionally substituted on carbon by one or more $R^2$; and wherein if said heterocyclyl contains an —NH— moiety that nitrogen may be optionally substituted by a group selected from $R^A$.

In one embodiment A is heterocyclyl.

In one embodiment A is a pyridyl.

In one embodiment A is a bond, $C_{1-6}$alkylene or heterocyclyl.

In one embodiment A is a bond, methylene or a pyridyl.

In one embodiment Q is a bond.

In one embodiment Q is carbocyclyl; wherein said carbocyclyl may be optionally substituted on carbon by one or more $R^3$.

In one embodiment Q is heterocyclyl; wherein said heterocyclyl may be optionally substituted on carbon by one or more $R^3$; and wherein if said heterocyclyl contains an —NH— moiety that nitrogen may be optionally substituted by a group selected from $R^B$.

In one embodiment Ring B is morpholinyl.

In one embodiment Ring B is morpholinyl; wherein if said morpholinyl contains an —NH— moiety that nitrogen may be optionally substituted by a group selected from $R^C$.

In one embodiment Ring B is thiomorpholinyl.

In one embodiment Ring B is thiomorpholinyl; wherein if said thiomorpholinyl contains an —NH— moiety that nitrogen may be optionally substituted by a group selected from $R^C$.

In one embodiment $R^1$ is halo.

In one embodiment n is 0.

In one embodiment n is 1.

In one embodiment n is 2.

In one embodiment n is 3.

In one embodiment n is 4.

In one embodiment there is provided a peptide dendron comprising one or more residues derived from a modified lysine of formula (I) wherein:

A is a bond, $C_{1-6}$alkylene or heterocyclyl;

Q is a bond;

Ring B is morpholinyl or thiomorpholinyl; and n is 0.

In one embodiment there is provided a peptide dendron comprising one or more residues derived from a modified lysine of formula (I) wherein:

A is a bond, methylene or a pyridyl;

Q is a bond;

Ring B is morpholinyl or thiomorpholinyl; and n is 0.

In one embodiment the modified lysine of formula (I) is a modified lysine of formula (IA):

(IA)

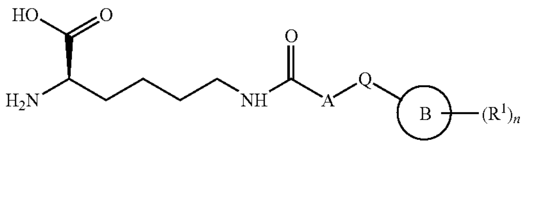

wherein A, Q, B, $R^1$ and n are as herein described. A modified lysine of formula (IA) may also be referred to as a modified D-lysine.

In one embodiment the modified lysine of formula (I) is a modified lysine of formula (IB):

(IB)

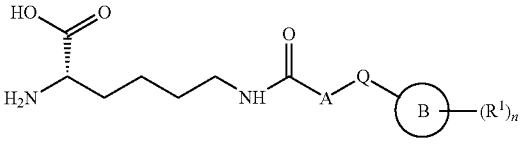

wherein A, Q, B, $R^1$ and n are as herein described. A modified lysine of formula (IB) may also be referred to as a modified L-lysine.

In one embodiment the modified lysine of formula (I) is selected from:

2-amino-6-{[6-(morpholin-4-yl)pyridine-3-carbonyl]amino}hexanoic acid;

2-amino-6-[(thiomorpholine-3-carbonyl)amino]hexanoic acid; and 2-amino-6-[2-(morpholin-4-yl)acetamido]hexanoic acid.

In one embodiment the modified lysine of formula (I) is selected from:

(R)-2-amino-6-{[6-(morpholin-4-yl)pyridine-3-carbonyl]amino}hexanoic acid;

(R)-2-amino-6-[(thiomorpholine-3-carbonyl)amino]hexanoic acid; and (R)-2-amino-6-[2-(morpholin-4-yl)acetamido]hexanoic acid.

In one embodiment the modified lysine of formula (I) is selected from:

(S)-2-amino-6-{[6-(morpholin-4-yl)pyridine-3-carbonyl]amino}hexanoic acid;

(S)-2-amino-6-[(thiomorpholine-3-carbonyl)amino]hexanoic acid; and (S)-2-amino-6-[2-(morpholin-4-yl)acetamido]hexanoic acid.

As used herein, the term "substituted", when refers to a chemical group, means the chemical group has one or more hydrogen atoms that is/are removed and replaced by substituents. As used herein, the term "substituent" has the ordinary meaning known in the art and refers to a chemical moiety that is covalently attached to a parent group. As used herein, the term "optionally substituted" means that the chemical group may have no substituents (i.e. unsubstituted) or may have one or more substituents (i.e. substituted). It is to be understood that substitution at a given atom is limited by valency. Where optional substituents are selected from a list of groups it is to be understood that this definition includes all substituents being chosen from one of the specified groups or the substituents being chosen from two or more of the specified groups. Where there may be more than one of the same substituent, e.g. $R^2$, it is to be understood that this definition also includes all such substituents being chosen from one of the specified groups or the substituents being chosen from two or more of the specified groups.

As used herein, the term "$C_{i-j}$" indicates a range of the carbon atoms numbers, wherein i and j are integers and the range of the carbon atoms numbers includes the endpoints (i.e. i and j) and each integer point in between, and wherein j is greater than i. For examples, $C_{1-6}$ indicates a range of one to six carbon atoms, including one carbon atom, two carbon atoms, three carbon atoms, four carbon atoms, five carbon atoms and six carbon atoms. In some embodiments, the term "$C_{1-6}$" indicates 1 to 6, 1 to 5, 1 to 4, 1 to 3 or 1 to 2 carbon atoms.

As used herein, the term "alkyl", whether as part of another term or used independently, refers to a saturated hydrocarbon chain. The hydrocarbon chain mentioned above may be straight-chain or branched-chain. The term "$C_{i-j}$alkyl" refers to an alkyl having i to j carbon atoms. Examples of $C_{1-6}$alkyl include, but are not limited to, methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. References to groups such as "butyl" without further qualification refer to all forms of butyl, for example n-butyl and tert-butyl etc.

As used herein, the term "alkylene", whether as part of another term or used independently, refers to a saturated hydrocarbon chain. The hydrocarbon chain mentioned above may be straight-chain or branched-chain. The term "$C_{i-j}$alkylene" refers to an alkyl having i to j carbon atoms. Examples of $C_{1-6}$alkylene include, but are not limited to, methylene ($—CH_2—$), ethylene ($—CH_2—CH_2—$), propylene ($—CH_2—CH_2—CH_2—$) and butylene ($—CH_2—CH_2—CH_2—CH_2—$ and $—CH_2—CH(CH_3)—CH_2—$ etc) and the like.

As used herein the term "halo" refers to fluoro, chloro, bromo and iodo.

A "heterocyclyl" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a $—CH_2—$ group can optionally be replaced by a —C(O)— and a ring sulphur atom may be optionally oxidised to form the S-oxides. Examples and suitable values of the term "heterocyclyl" are morpholino, piperidyl, pyridyl, pyranyl, pyrrolyl, pyrazolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone and 4-thiazolidone. A particular example of the term "heterocyclyl" is pyridyl. In one embodiment a "heterocyclyl" is a saturated, partially saturated or unsaturated, monocyclic ring containing 5 or 6 atoms of which at least one atom is chosen from nitrogen, sulphur or oxygen, it may, unless otherwise specified, be carbon or nitrogen linked, a $—CH_2—$ group can optionally be replaced by a —C(O)— and a ring sulphur atom may be optionally oxidised to form the S-oxides.

A "carbocyclyl" is a saturated, partially saturated or unsaturated, mono or bicyclic carbon ring that contains 3-12 atoms; wherein a $—CH_2—$ group can optionally be replaced by a —C(O)—. In one embodiment "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. A particular example of "carbocyclyl" is phenyl.

The "compounds" of the present disclosure encompass all isotopes of atoms in the compounds. Isotopes of an atom include atoms having the same atomic number but different mass numbers. For example, unless otherwise specified, hydrogen, carbon, nitrogen, oxygen, phosphorous, sulphur, fluorine, chlorine, bromide or iodine in the "compound" of present disclosure are meant to also include their isotopes such as but are not limited to: $^{1}H$, $^{2}H$, $^{3}H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{19}F$, $^{35}Cl$, $^{37}Cl$, $^{79}Br$, $^{81}Br$, $^{127}I$ and $^{131}I$. In some embodiments, hydrogen includes protium, deuterium and tritium. In some embodiments, hydrogen refers to protium. In some embodiments, hydrogen refers to deuterium. In some embodiments, hydrogen refers to tritium. In some embodiments, the term "substituted by deuterium" or "deuterium substituted" to replace the other isoform of hydrogen (e.g. protium) in the chemical group with deuterium. In some embodiments, carbon includes $^{12}C$ and $^{13}C$.

Residue

The amino acids in the peptide dendrons described herein are linked together to form a chain via peptide bonds between the α-amino groups and the carboxy groups. Once linked in the chain, an individual amino acid is referred to as a "residue". A "residue" is derived from an amino acid. "Residue" may also be used to describe a terminal amino acid linked only via the α-amino group or the carboxy group; optionally where the terminal amino group is a modified amino group or the terminal carboxy group is a modified carboxy group (as described herein below). References to specific amino acids herein (for example "lysine") may be referring to the amino acid itself or the residue, depending on the context.

Modified Lysine

In any embodiment where modified lysines or residues derived from a modified lysine are mentioned, these refer to lysines modified according to formula (I) and embodiments thereof.

In any embodiment where a modified lysine or residues derived from a modified lysine is mentioned, this may refer to a modified D-lysine.

In any embodiment where a modified lysine or residues derived from a modified lysine is mentioned, this may refer to a modified L-lysine.

Salt Forms

In any embodiment where peptide dendrons are mentioned, this may refer to peptide dendrons in salt form.

As used herein, "salt form" refers to derivatives of the peptide dendrons described herein wherein the parent compound is modified by converting one or more existing acidic moieties (e.g. carboxyl and the like) and/or base moieties (e.g. amine, alkali and the like) to its salt form. In many cases, compounds of present disclosure are capable of forming acid and/or base salts by virtue of the presence of amino and/or carboxyl groups or groups similar thereto. A particular salt form is a pharmaceutically acceptable salt. As used herein a "pharmaceutically acceptable salt" is a salt that is safe and effective for use in mammals, particularly human beings.

Suitable salt forms of a peptide dendron described herein includes, for example, an acid-addition salt, which can be derived from for example an inorganic acid (for example, hydrochloric, hydrobromic, sulfuric, nitric, phosphoric acid and the like) or organic acid (for example, formic, acetic, propionic, glycolic, oxalic, maleic, malonic, succinic, fumaric, tartaric, trimesic, citric, lactic, phenylacetic, benzoic, mandelic, methanesulfonic, napadisylic, ethanesulfonic, toluenesulfonic, trifluoroacetic, salicylic, sulfosalicylic acids and the like). A particular acid-addition salt is a hydrochloride.

Suitable salt forms of a peptide dendron described herein includes, for example, an base-addition salt, which can be derived from for example an inorganic bases (for example, sodium, potassium, ammonium salts and hydroxide, carbonate, bicarbonate salts of metals from columns I to XII of the periodic table such as calcium, magnesium, iron, silver, zinc, copper and the like) or organic bases (for example, primary, secondary, and tertiary amines, substituted amines including naturally occurring substituted amines, cyclic amines, basic ion exchange resins, and the like). Certain organic amines include but are not limited to isopropylamine, benzathine, cholinate, diethanolamine, diethylamine, lysine, meglumine, piperazine and tromethamine. Lists of additional suitable salts can be found, e.g. in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Peptide Dendron Terminology Used Herein

The present application describes a peptide dendron comprising one or more residues derived from a modified lysine of formula (I) as described herein. Herein where a peptide dendron is mentioned, this refers to a 3-dimensional structure comprising amino acid residues, wherein the side chain of one of the residues, e.g. the ε-amine of a lysine, forms a branch point creating subsequent generations, building up the molecule into a 3-D macromolecule. Peptide dendrons comprise at least one branch point, forming a non-linear molecule with at least one generation (G1).

The following terminology is used herein:

- Generation 0: The sequence of amino acid residues preceding the first branch point within the peptide dendron.
- Branch point: The amino acid residue with a sidechain that is modified by the addition of an amino acid residue that begins a new generation.
- Generations: The amino acid residues between branch points, where each successive series of generations are numbered (G1, G2, G3 . . . ).
- Targeting group: A moiety with an affinity for a specific cell-type or organ for example sugar, small molecule, peptide, and/or antibody based.

In line with convention, peptides are drawn N-terminal amino acid first and the C-terminal amino acid at the end (writing left to right).

Lysine (LYS) refers to unmodified lysine unless otherwise stated.

In any embodiment where an amino acid may be chiral, this may refer to a D-amino acid.

In any embodiment where an amino acid may be chiral, this may refer to an L-amino acid.

In any embodiment where an amino acid may be chiral, the amino acid may be a mixture of L- and D-amino acids.

Peptide Dendrons

In any embodiment where a peptide dendron is mentioned, this may refer to a peptide dendron synthesised via techniques that allow precise control over its composition and purity. Suitable techniques include solid phase peptide synthesis.

In any embodiment where a peptide dendron is mentioned, this may refer to a peptide dendron where the branch points, generation 0 and successive generations together comprise fewer than 120 amino acid residues.

In any embodiment where a peptide dendron is mentioned, this may refer to a peptide dendron where the branch points, generation 0 and successive generations together comprise fewer than 100 amino acid residues.

In any embodiment where a peptide dendron is mentioned, this may refer to a peptide dendron where the branch points, generation 0 and successive generations together comprise fewer than 80 amino acid residues.

In any embodiment where a peptide dendron is mentioned, this may refer to a peptide dendron where the branch points, generation 0 and successive generations together comprise fewer than 60 amino acid residues.

In any embodiment where a peptide dendron is mentioned, this may refer to a peptide dendron where the branch points, generation 0 and successive generations together comprise about 52 amino acid residues.

In any embodiment where a peptide dendron is mentioned, this may refer to a peptide dendron where the branch points, generation 0 and successive generations together comprise 52 amino acid residues.

In any embodiment where a peptide dendron is mentioned, the peptide dendron may be in salt form.

In any embodiment where a peptide dendron is mentioned, the peptide dendron comprises one or more residues derived from a modified lysine as defined herein, and one or more leucine residues.

In any embodiment where a peptide dendron is mentioned, the peptide dendron comprises one or more residues derived from a modified lysine as defined herein, and one or more arginine residues.

In any embodiment where a peptide dendron is mentioned, the peptide dendron comprises one or more residues derived from a modified lysine as defined herein, and one or more lysine residues.

In any embodiment where a peptide dendron is mentioned, the peptide dendron comprises one or more residues derived from a modified lysine as defined herein, one or more arginine residues, and one or more lysine residues.

In any embodiment where a peptide dendron is mentioned, the peptide dendron comprises one or more residues derived from a modified lysine as defined herein, one or more leucine residues, and one or more lysine residues.

In any embodiment where a peptide dendron is mentioned, the peptide dendron comprises one or more residues derived from a modified lysine as defined herein, one or more arginine residues and one or more leucine residues.

In any embodiment where a peptide dendron is mentioned, at least one generation comprises one or more residues derived from a modified lysine as defined herein, and one or more leucine residues.

In any embodiment where a peptide dendron is mentioned, at least one generation comprises one or more residues derived from a modified lysine as defined herein, and one or more arginine residues.

In any embodiment where a peptide dendron is mentioned, at least one generation comprises one or more residues derived from a modified lysine as defined herein, and one or more lysine residues.

In any embodiment where a peptide dendron is mentioned, at least one generation comprises one or more residues derived from a modified lysine as defined herein, one or more arginine residues, and one or more lysine residues.

In any embodiment where a peptide dendron is mentioned, at least one generation comprises one or more residues derived from a modified lysine as defined herein, one or more leucine residues, and one or more lysine residues.

In any embodiment where a peptide dendron is mentioned, at least one generation comprises one or more residues derived from a modified lysine as defined herein, one or more arginine residues and one or more leucine residues.

In any embodiment where a peptide dendron is mentioned, the generation(s) comprise one or more residues derived from a modified lysine as defined herein, and one or more leucine residues.

In any embodiment where a peptide dendron is mentioned, the generation(s) comprise one or more residues derived from a modified lysine as defined herein, and one or more arginine residues.

In any embodiment where a peptide dendron is mentioned, the generation(s) comprise one or more residues derived from a modified lysine as defined herein, and one or more lysine residues.

In any embodiment where a peptide dendron is mentioned, the generation(s) comprise one or more residues derived from a modified lysine as defined herein, one or more arginine residues, and one or more lysine residues.

In any embodiment where a peptide dendron is mentioned, the generation(s) comprise one or more residues derived from a modified lysine as defined herein, one or more leucine residues, and one or more lysine residues.

In any embodiment where a peptide dendron is mentioned, the generation(s) comprise one or more residues derived from a modified lysine as defined herein, one or more arginine residues and one or more leucine residues.

In any embodiment where a peptide dendron is mentioned, the % amino acids with a side chain pka>7.4 is 25-50%.

In any embodiment where a peptide dendron is mentioned, the % amino acids with a side chain pka>7.4 is 25-30%.

In any embodiment where a peptide dendron is mentioned, the % amino acids with a side chain pka>7.4 is 30-35%.

In any embodiment where a peptide dendron is mentioned, the % amino acids with a side chain pka=4.0-6.5 is 30-35%.

In any embodiment where a peptide dendron is mentioned, the % amino acids with a side chain pka=4.0-6.5 is 35-40%.

In any embodiment where a peptide dendron is mentioned, the % amino acids with a side chain pka=4.0-6.5 is 40-45%.

In any embodiment where a peptide dendron is mentioned, the % amino acids with a side chain pka=4.0-6.5 is 45-50%.

In any embodiment where a peptide dendron is mentioned, of the amino acid residues in successive generations, the % with a side chain pka>7.4 is 25-50% and the % with a side chain pka=4.0-6.5 is 25-50%.

In any embodiment where a peptide dendron is mentioned, the peptide dendron comprises a peptide dendron of formula (II):

$$(\{X_3\}\{X_2\}\{X_1\})_8(\{BP\}\{X_3\}\{X_2\}\{X_1\})_4(\{BP\}\{X_3\}\{X_2\}\{X_1\})_2\{BP\}$$

wherein:

- one of $X_1$, $X_2$, or $X_3$ is a basic amino acid residue;
- another $X_1$, $X_2$, or $X_3$ is a hydrophobic amino acid residue;
- the remaining $X_1$, $X_2$, or $X_3$ is a residue derived from a modified lysine as defined herein; and
- BP is a branch point amino acid residue.

In formula (II) one $X_1$ group is attached to the α-amine of the BP amino acid, and the other is attached to a reactive group, for example an amino group, on the side chain, for example to the ε-amine of a lysine. Peptide dendrons of formula (II) have the following structure:

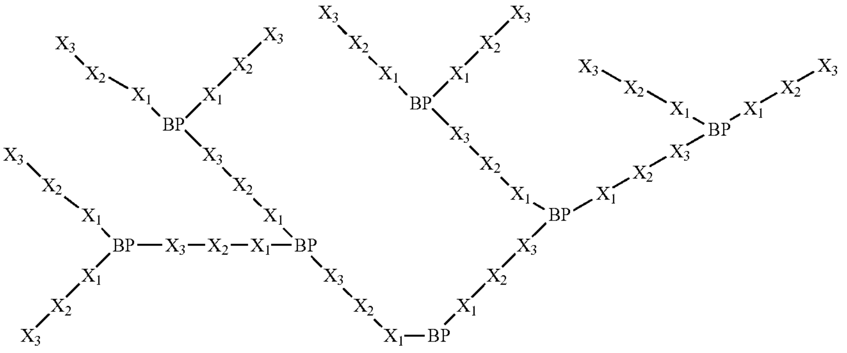

In any embodiment where a peptide dendron is mentioned, the % amino acids with a side chain pka>7.4 is 35-40%.

In any embodiment where a peptide dendron is mentioned, the % amino acids with a side chain pka>7.4 is 40-45%.

In any embodiment where a peptide dendron is mentioned, the % amino acids with a side chain pka>7.4 is 45-50%.

In any embodiment where a peptide dendron is mentioned, the % amino acids with a side chain pka=4.0-6.5 is 25-50%.

In any embodiment where a peptide dendron is mentioned, the % amino acids with a side chain pka=4.0-6.5 is 25-30%.

In peptide dendrons of formula (II), the $X_1$ amino acid residue within the same generation may be the same or different, and/or the $X_1$ amino acid residue in different generations may be the same or different. The same applies to $X_2$ and $X_3$ respectively.

In one embodiment $X_1$ is a basic amino acid residue.

In one embodiment $X_1$ is a hydrophobic amino acid residue.

In one embodiment $X_1$ is a residue derived from a modified lysine as defined herein.

In one embodiment $X_2$ is a basic amino acid residue.

In one embodiment $X_2$ is a hydrophobic amino acid residue.

In one embodiment $X_2$ is a residue derived from a modified lysine as defined herein.

In one embodiment $X_3$ is a basic amino acid residue.

In one embodiment $X_3$ is a hydrophobic amino acid residue.

In one embodiment $X_3$ is a residue derived from a modified lysine as defined herein.

In one embodiment:

$X_1$ is a basic amino acid residue;

$X_2$ is a hydrophobic amino acid residue; and $X_3$ is a residue derived from a modified lysine as defined herein.

In one embodiment:

$X_3$ is a basic amino acid residue;

$X_2$ is a hydrophobic amino acid residue; and $X_1$ is a residue derived from a modified lysine as defined herein.

One of $X_1$, $X_2$, or $X_3$ is a basic amino acid residue. A basic amino acid residue is an amino acid residue with a side chain capable of carrying a positive charge.

In one embodiment the basic amino acid residue is selected from arginine, ornithine and lysine.

In one embodiment the basic amino acid residue is arginine.

In one embodiment the basic amino acid residue is ornithine.

In one embodiment the basic amino acid residue is lysine.

In one embodiment $X_1$ is selected from arginine, ornithine and lysine.

In one embodiment $X_1$ is arginine.

In one embodiment $X_1$ is ornithine.

In one embodiment $X_1$ is lysine.

In one embodiment $X_2$ is selected from arginine, ornithine and lysine.

In one embodiment $X_2$ is arginine.

In one embodiment $X_2$ is ornithine.

In one embodiment $X_2$ is lysine.

In one embodiment the $X_3$ is selected from arginine, ornithine and lysine.

In one embodiment $X_3$ is arginine.

In one embodiment $X_3$ is ornithine.

In one embodiment $X_3$ is lysine.

One of $X_1$, $X_2$, or $X_3$ is a hydrophobic amino acid residue. A hydrophobic amino acid residue is an amino acid residue with a side chain that is composed mostly of carbon and hydrogen, and tends to be repelled from water.

In one embodiment the hydrophobic amino acid residue is selected from alanine, isoleucine, leucine, phenylalanine, tryptophan, tyrosine, methionine and valine.

In one embodiment the hydrophobic amino acid residue is alanine.

In one embodiment the hydrophobic amino acid residue is isoleucine.

In one embodiment the hydrophobic amino acid residue is leucine.

In one embodiment the hydrophobic amino acid residue is phenylalanine.

In one embodiment the hydrophobic amino acid residue is tryptophan.

In one embodiment the hydrophobic amino acid residue is tyrosine.

In one embodiment the hydrophobic amino acid residue is methionine.

In one embodiment the hydrophobic amino acid residue is valine.

In one embodiment $X_1$ is selected from alanine, isoleucine, leucine, phenylalanine, tryptophan, tyrosine, methionine and valine.

In one embodiment $X_1$ is alanine.

In one embodiment $X_1$ is isoleucine.

In one embodiment $X_1$ is leucine.

In one embodiment $X_1$ is phenylalanine.

In one embodiment $X_1$ is tryptophan.

In one embodiment $X_1$ is tyrosine.

In one embodiment $X_1$ is methionine.

In one embodiment $X_1$ is valine.

In one embodiment $X_2$ is selected from alanine, isoleucine, leucine, phenylalanine, tryptophan, tyrosine, methionine and valine.

In one embodiment $X_2$ is alanine.

In one embodiment $X_2$ is isoleucine.

In one embodiment $X_2$ is leucine.

In one embodiment $X_2$ is phenylalanine.

In one embodiment $X_2$ is tryptophan.

In one embodiment $X_2$ is tyrosine.

In one embodiment $X_2$ is methionine.

In one embodiment $X_2$ is valine.

In one embodiment $X_3$ is selected from alanine, isoleucine, leucine, phenylalanine, tryptophan, tyrosine, methionine and valine.

In one embodiment $X_3$ is alanine.

In one embodiment $X_3$ is isoleucine.

In one embodiment $X_3$ is leucine.

In one embodiment $X_3$ is phenylalanine.

In one embodiment $X_3$ is tryptophan.

In one embodiment $X_3$ is tyrosine.

In one embodiment $X_3$ is methionine.

In one embodiment $X_3$ is valine.

In any embodiment where a peptide dendron is mentioned, the peptide dendron comprises a peptide dendron of formula (II) as defined herein wherein:

$X_1$ is arginine;

$X_2$ is leucine;

$X_3$ is a residue derived from a modified lysine as defined herein; and

BP is lysine.

In any embodiment where a peptide dendron is mentioned, the peptide dendron comprises a peptide dendron of formula (II) as defined herein wherein:

$X_1$ is a residue derived from a modified lysine as defined herein;

$X_2$ is leucine;

$X_3$ is arginine; and

BP is lysine.

Generation 0

In any embodiment where a peptide dendron is mentioned, the peptide dendron comprises a sequence of amino acid residues referred to as "Generation 0" attached to the 1st branch point amino acid in the peptide dendron. A Generation 0 sequence of amino acid residues may be at the C-terminus, or the N-terminus, particularly the C-terminus. For example a peptide dendron with a Generation 0 sequence of amino acid residues may be illustrated as follows:

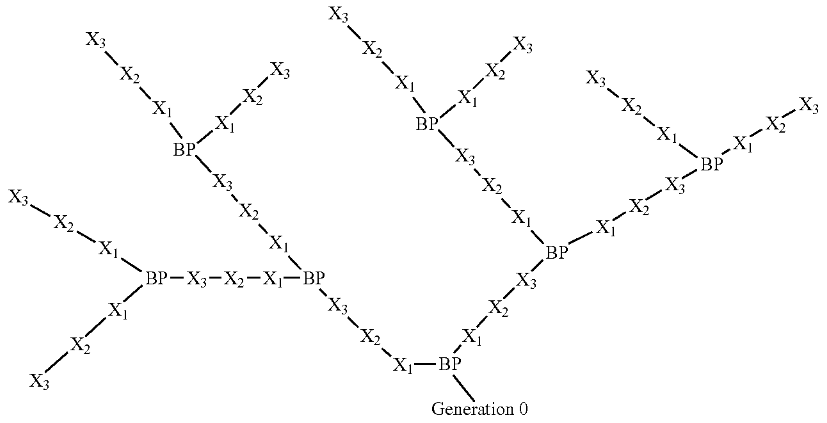

Where the 1st branch point is lysine, the Generation 0 sequence in the above diagram may be attached as follows:

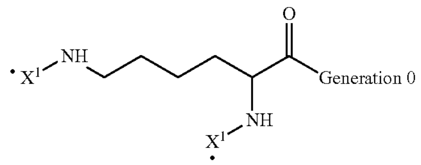

where " . . . " represents the rest of the molecule.

In any embodiment where a peptide dendron is mentioned, the peptide dendron comprises a Generation 0 sequence of amino acids at the C-terminus of the branch point amino acid preceding the first generation.

In any embodiment where a peptide dendron is mentioned, the peptide dendron comprises a Generation 0 sequence of amino acids at the N-terminus of the branch point amino acid preceding the first generation.

In any embodiment where a Generation 0 sequence of amino acids is mentioned, the Generation 0 sequence comprises one or more glycine residues.

In any embodiment where a Generation 0 sequence of amino acids is mentioned, the Generation 0 sequence comprises a glycine residue.

In any embodiment where a Generation 0 sequence of amino acids is mentioned, the Generation 0 sequence comprises two glycine residues.

In any embodiment where a Generation 0 sequence of amino acids is mentioned, the Generation 0 sequence comprises three glycine residues.

In any embodiment where a Generation 0 sequence of amino acids is mentioned, the Generation 0 sequence comprises one or more valine residues.

In any embodiment where a Generation 0 sequence of amino acids is mentioned, the Generation 0 sequence comprises a valine residue.

In any embodiment where a Generation 0 sequence of amino acids is mentioned, the Generation 0 sequence comprises one or more citrulline residues.

In any embodiment where a Generation 0 sequence of amino acids is mentioned, the Generation 0 sequence comprises a citrulline residue.

In any embodiment where a Generation 0 sequence of amino acids is mentioned, the Generation 0 sequence comprises one or more serine residues.

In any embodiment where a Generation 0 sequence of amino acids is mentioned, the Generation 0 sequence comprises a serine residue.

In any embodiment where a Generation 0 sequence of amino acids is mentioned, the Generation 0 sequence comprises one or more cysteine residues.

In any embodiment where a Generation 0 sequence of amino acids is mentioned, the Generation 0 sequence comprises a cysteine residue.

In any embodiment where a Generation 0 sequence of amino acids is mentioned, the Generation 0 sequence may terminate at a cysteine residue. A terminal cysteine permits additional functionalization via thiol chemistry. In another embodiment, the Generation 0 sequence may terminate at a lysine, serine, tyrosine and/or a reactive derivative of an amino acid such as azidophenyl alanine. Other reactive derivatives of amino acids include those containing azide, alkyne, cyclopentadiene, and tetrazine groups.

In any embodiment where a Generation 0 sequence of amino acids is mentioned, the Generation 0 sequence terminates at a cysteine residue wherein the terminal carboxy group has been amidated to form a $C(O)NH_2$ group. Amidation renders the COOH group inert and reduces overall peptide charge and better mimics natural peptides.

In any embodiment where a Generation 0 sequence of amino acids is mentioned, the Generation 0 sequence comprises glycine, valine, citrulline, serine, alanine, lysine, phenylalanine and/or cysteine residues.

In any embodiment where a Generation 0 sequence of amino acids is mentioned, the Generation 0 sequence comprises glycine, valine, citrulline, serine and/or cysteine residues.

In any embodiment where a Generation 0 sequence of amino acids is mentioned, the Generation 0 sequence comprises glycine, valine, citrulline, serine and cysteine residues.

In any embodiment where a Generation 0 sequence of amino acids is mentioned, the Generation 0 sequence consists of GLY-VAL-CIT-GLY-GLY-SER-CYS (SEQ ID NO 5).

In any embodiment where a Generation 0 sequence of amino acids is mentioned, the Generation 0 sequence comprises the sequence VAL-CIT, VAL-ALA, LYS-PHE, GLY-GLY-PHE-GLY (SEQ ID NO 1) or GLY-PHE-LEU-GLY (SEQ ID NO 2).

Branch Point

A branch point is the amino acid residue with a sidechain that is modified by the addition of an amino acid residue that begins a new generation. The branch points are marked as BP in the following diagram:

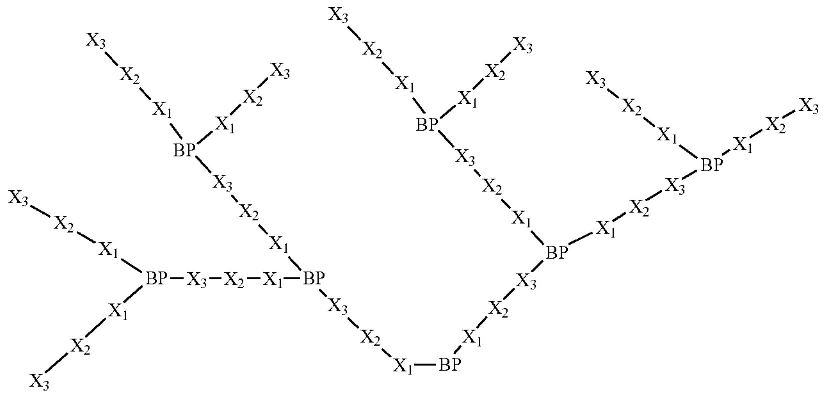

Where a branch point is lysine, the lysine may form the branch points in the above diagram as follows:

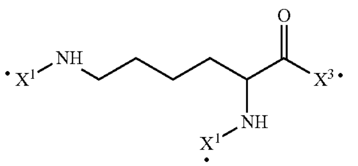

where " . . . " represents the rest of the molecule.

In any embodiment where a peptide dendron is mentioned, the branch points within the peptide dendron may be the same or different amino acid residues.

In any embodiment where a peptide dendron is mentioned, the branch points within the peptide dendron may be the same amino acid residues.

In any embodiment where a peptide dendron is mentioned, this may refer to a peptide dendron wherein a lysine forms one or more branch points.

In any embodiment where a peptide dendron is mentioned, this may refer to a peptide dendron wherein a lysine forms all the branch points.

Generations

Peptide dendrons comprise generations. Generations may be illustrated as follows:

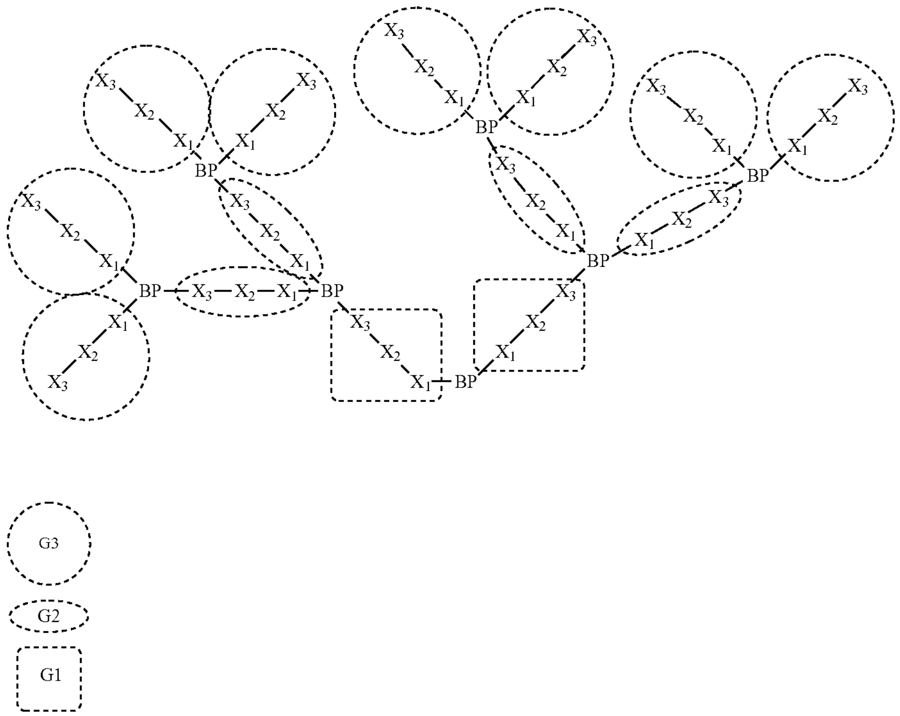

wherein G1 represents the 1st generation, G2 the 2nd generation and G3 the 3rd generation, collectively referred to as generations. A further generation may be added via the addition of a further branch point (BP) amino acid to the terminal $X_3$ groups in the G3 generation, followed by the addition of a G4 generation sequences of amino acid residues, for example additional $X_3$-$X_2$-$X_1$ groups, and so on.

In any embodiment where a peptide dendron is mentioned, this may refer to a peptide dendron comprising generations consisting of 5 amino acid residues.

In any embodiment where a peptide dendron is mentioned, this may refer to a peptide dendron comprising generations consisting of 4 amino acid residues.

In any embodiment where a peptide dendron is mentioned, this may refer to a peptide dendron comprising generations consisting of 3 amino acid residues.

In any embodiment where a peptide dendron is mentioned, this may refer to a peptide dendron comprising generations consisting of 2 amino acid residues.

In any embodiment where a peptide dendron is mentioned, this may refer to a peptide dendron comprising generations consisting of 4 or more amino acid residues.

In any embodiment where a peptide dendron is mentioned, this may refer to a peptide dendron comprising generations consisting of 3 or more amino acid residues.

In any embodiment where a peptide dendron is mentioned, this may refer to a peptide dendron comprising generations consisting of 2 or more amino acid residues.

In any embodiment where a peptide dendron is mentioned, this may refer to a peptide dendron comprising generations consisting of up to 5 amino acid residues.

In any embodiment where a peptide dendron is mentioned, this may refer to a peptide dendron comprising generations consisting of up to 4 amino acid residues.

In any embodiment where a peptide dendron is mentioned, this may refer to a peptide dendron comprising generations consisting of up to 3 amino acid residues.

In any embodiment where a peptide dendron is mentioned, this may refer to a peptide dendron comprising generations consisting of the same peptide chain.

In any embodiment where a peptide dendron is mentioned, this may refer to a peptide dendron comprising generations consisting of the same peptide chain in each generation.

In any embodiment where a peptide dendron is mentioned, this may refer to a peptide dendron comprising generations consisting of different peptide chains.

In any embodiment where a peptide dendron is mentioned, this may refer to a peptide dendron comprising generations consisting of different peptide chains in each generation.

In any embodiment where a peptide dendron is mentioned, this may refer to a peptide dendron comprising generations comprising a basic amino acid residue.

In any embodiment where a peptide dendron is mentioned, this may refer to a peptide dendron comprising generations comprising a hydrophobic amino acid residue.

In any embodiment where a peptide dendron is mentioned, this may refer to a peptide dendron comprising generations comprising a basic amino acid residue and a hydrophobic amino acid residue.

In any embodiment where a peptide dendron is mentioned, this may refer to a peptide dendron comprising generations comprising a basic amino acid residue, a hydrophobic amino acid residue and a residue derived from a modified lysine as defined herein.

In any embodiment where a peptide dendron is mentioned, this may refer to a peptide dendron comprising generations comprising one or more residues derived from a modified lysine as defined herein, and one or more leucine residues.

In any embodiment where a peptide dendron is mentioned, this may refer to a peptide dendron comprising generations comprising one or more residues derived from a modified lysine as defined herein, and one or more arginine residues.

In any embodiment where a peptide dendron is mentioned, this may refer to a peptide dendron comprising generations comprising one or more residues derived from a modified lysine as defined herein, one or more arginine residues and one or more leucine residues.

In any embodiment where a peptide dendron is mentioned, this may refer to a peptide dendron comprising one or more generations comprising ARG-LEU-LYS (modified) wherein LYS (modified) is a residue derived from a modified lysine as defined herein.

In any embodiment where a peptide dendron is mentioned, this may refer to a peptide dendron comprising one or more generations consisting of ARG-LEU-LYS (modified) wherein LYS (modified) is a residue derived from a modified lysine as defined herein.

In any embodiment where a peptide dendron is mentioned, this may refer to a peptide dendron comprising all generations comprising ARG-LEU-LYS (modified) wherein LYS (modified) is a residue derived from a modified lysine as defined herein.

In any embodiment where a peptide dendron is mentioned, this may refer to a peptide dendron comprising all generations consisting of ARG-LEU-LYS (modified) wherein LYS (modified) is a residue derived from a modified lysine as defined herein.

In any embodiment where a peptide dendron is mentioned, this may refer to a peptide dendron comprising one or more generations comprising LYS (modified)-LEU-ARG wherein LYS (modified) is a residue derived from a modified lysine as defined herein.

In any embodiment where a peptide dendron is mentioned, this may refer to a peptide dendron comprising one or more generations consisting of LYS (modified)-LEU-ARG wherein LYS (modified) is a residue derived from a modified lysine as defined herein.

In any embodiment where a peptide dendron is mentioned, this may refer to a peptide dendron comprising all generations comprising LYS (modified)-LEU-ARG wherein LYS (modified) is a residue derived from a modified lysine as defined herein.

In any embodiment where a peptide dendron is mentioned, this may refer to a peptide dendron comprising all generations consisting of LYS (modified)-LEU-ARG wherein LYS (modified) is a residue derived from a modified lysine as defined herein.

In any embodiment where a peptide dendron is mentioned, this may refer to a peptide dendron comprising one generation.

In any embodiment where a peptide dendron is mentioned, this may refer to a peptide dendron comprising two generations.

In any embodiment where a peptide dendron is mentioned, this may refer to a peptide dendron comprising three generations.

In any embodiment where a peptide dendron is mentioned, this may refer to a peptide dendron comprising four generations.

In any embodiment where a peptide dendron is mentioned, this may refer to a peptide dendron comprising five generations.

In any embodiment where a peptide dendron is mentioned, this may refer to a one generation peptide dendron.

In any embodiment where a peptide dendron is mentioned, this may refer to a two generation peptide dendron.

In any embodiment where a peptide dendron is mentioned, this may refer to a three generation peptide dendron.

In any embodiment where a peptide dendron is mentioned, this may refer to a four generation peptide dendron.

polymerization of ethylene oxide. PEG polymers may be linear, or branched. Branched PEGs typically have three to thirty PEG chains emanating from a central core group.

In one embodiment the peptide dendrons described herein may comprise a polyethylene glycol group, referred to herein as a "polyethylene glycol peptide dendron" or "PEG peptide dendron". A PEG group may assist in stabilising the nanoparticle and form a "stealth layer" that reduces non-specific protein interactions through steric shielding.

A PEG group may be attached to the terminal amino acid residue in the Generation 0 sequence of amino acids, optionally via a linking group, of the peptide dendron as follows:

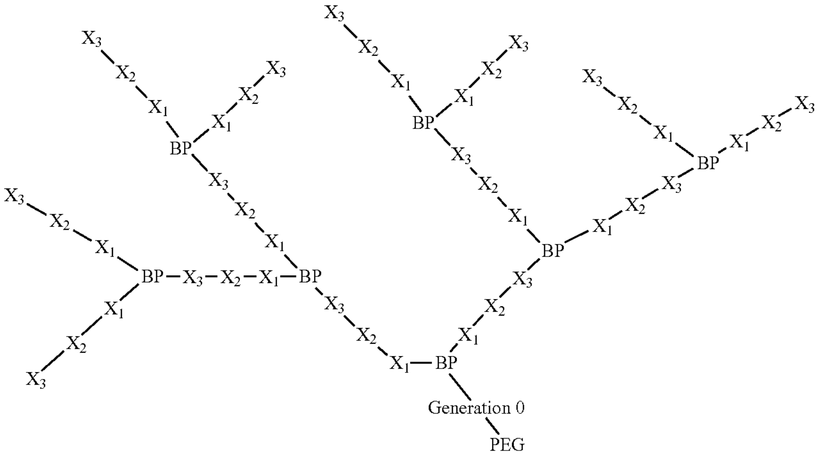

In any embodiment where a peptide dendron is mentioned, this may refer to a five generation peptide dendron.

In any embodiment where a peptide dendron is mentioned, this may refer to a peptide dendron comprising more than one generation.

In any embodiment where a peptide dendron is mentioned, this may refer to a peptide dendron comprising more than two generations.

In any embodiment where a peptide dendron is mentioned, this may refer to a peptide dendron comprising more than three generations.

In any embodiment where a peptide dendron is mentioned, this may refer to a peptide dendron comprising more than four generations.

In any embodiment where a peptide dendron is mentioned, this may refer to a peptide dendron comprising fewer than six generations.

In any embodiment where a peptide dendron is mentioned, this may refer to a peptide dendron comprising fewer than five generations.

In any embodiment where a peptide dendron is mentioned, this may refer to a peptide dendron comprising fewer than four generations.

In any embodiment where a peptide dendron is mentioned, this may refer to a peptide dendron comprising fewer than three generations.

Polyethylene Glycol Peptide Dendrons

In a further embodiment the peptide dendrons described herein may further comprise a biocompatible, hydrophilic polymer, for example a polyethylene glycol or polysarcosine group.

Polyethylene glycol (PEG) is a polymer consisting of $-(OCH2CH_2)_n-$ repeating subunits where typically n>3 and <250. It is typically synthesised using ring-opening polymerization of ethylene oxide.

The PEG group may be attached to the peptide dendron via a terminal-O— group, or via a terminal $-CH_2-$ group of the PEG; and may be attached to the amine or carboxy of the terminal amino acid residue in the Generation 0 sequence of amino acids, optionally via a linking group. The PEG group may also be attached to a reactive group on a side chain of the terminal amino acid residue, for example the —SH group on the side chain of a terminal cysteine, optionally via a linking group, particularly where the terminal carboxy group of the terminal cysteine has also been amidated.

In any embodiment where polyethylene glycol peptide dendrons are mentioned there may be modifications at the terminal end of the PEG group that is not attached to the peptide dendron, or the terminal end may be hydrogen. A suitable modification for the terminal end of the polyethylene glycol group, is for example $C_{1-4}$alkyl, e.g. methyl; or $C_{1-4}$alkoxy, e.g. methoxy.

In any embodiment where polyethylene glycol peptide dendrons are mentioned there may be a reactive group at the terminal end of the PEG group that is not attached to the peptide dendron, or the terminal end may be hydrogen. Suitable reactive groups include maleimide, azide, alkyne (e.g. $C_{2-6}$alkyne), and cyclopentadiene. This reactive group can be used to attach species such as radiolabels, dyes, and cell targeting ligands before or after PEG conjugation to the peptide dendron.

In any embodiment where polyethylene glycol peptide dendrons are mentioned there may be a linking group between the polyethylene glycol group and the peptide dendron. A suitable linking group is $C_{1-4}$alkylamino, for example $-CH_2-CH_2-NH-$, forming for example a PEG-$CH_2$—$CH_2$—NH-PD or a PEG-NH—$CH_2$—$CH_2$-PD; or $C_{1-4}$alkylene, for example $-CH_2-CH_2-$, forming for example a PEG-$CH_2$—$CH_2$-PD; wherein PD is the peptide dendron.

Where the polyethylene glycol group is attached to a reactive group on a side chain of the terminal amino acid residue, for example the —SH group on the side chain of a terminal cysteine, various methods may be employed to attach the polyethylene glycol group. Typically this results in the polyethylene glycol group being attached to the peptide dendron via a linker group. For example, polyethylene glycol functionalised with a 3-maleimido propanoic acid functional group connected to the polyethylene glycol via an amide bond, is a thiol-reactive reagent. The other end of the polyethylene glycol molecule may be methyl-terminated. A reaction employing a functionalised polyethylene glycol group of this nature resulting in a linker group between the PEG group and the peptide dendron may be illustrated as follows:

PD—SH +

-continued

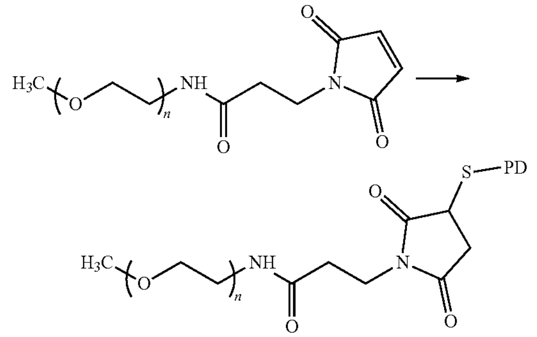

where the "SH" in "PD-SH" refers to the thiol on the cysteine side chain, PD is the peptide dendron, and "n" is the number of $-(OCH_2CH_2)_n-$ repeating subunits.

Examples of further functionalised PEG groups comprising a branched PEG group include:

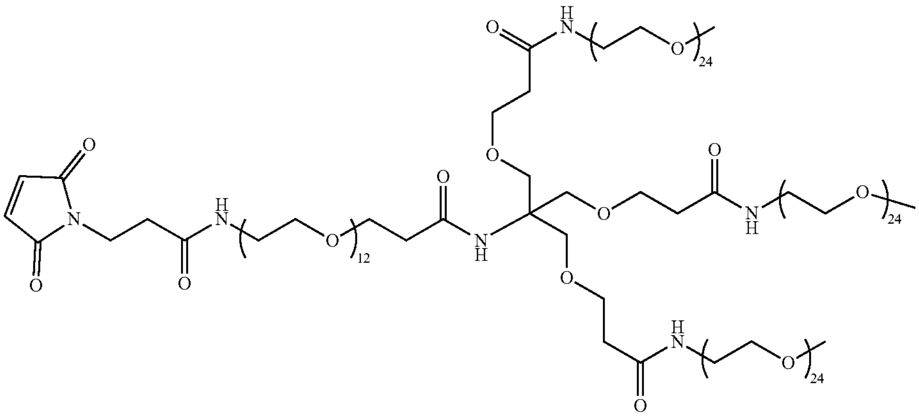

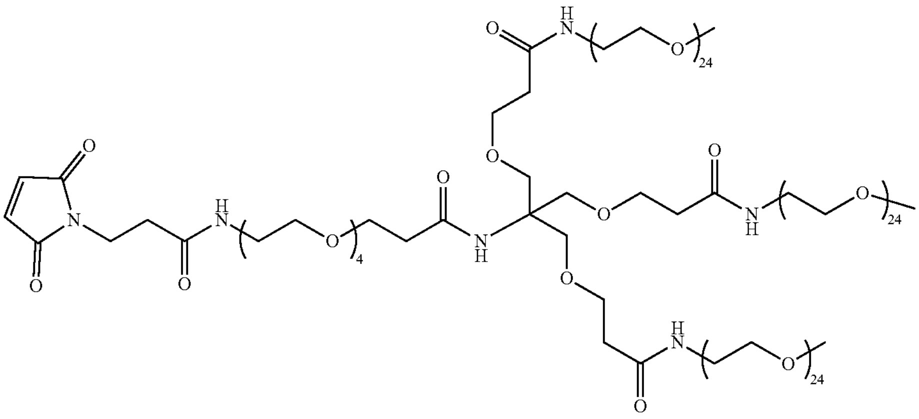

An example of such a peptide dendron comprising a branched PEG group is:

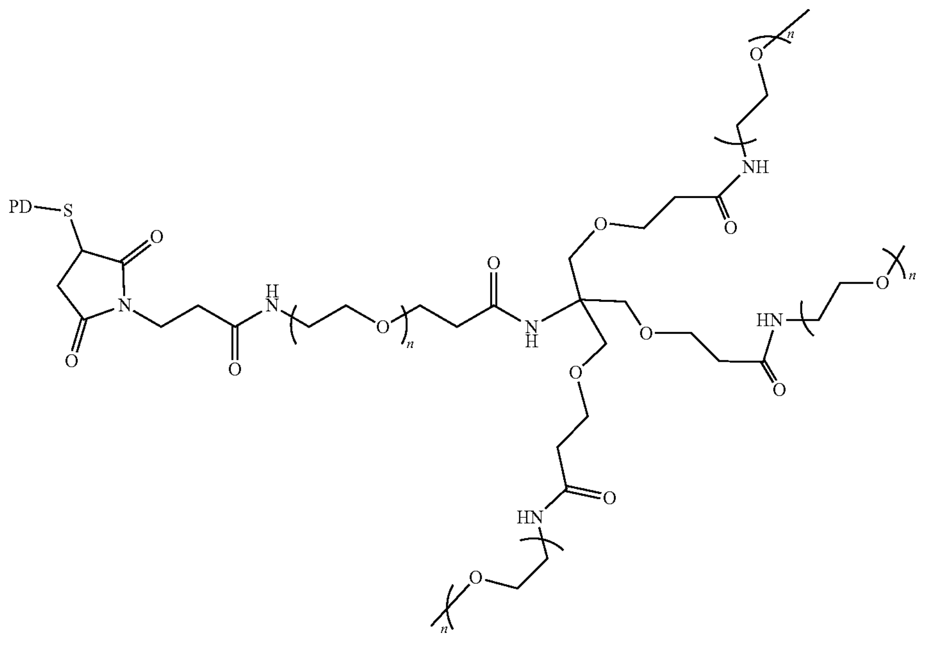

wherein n is the number of $-CH_2CH_2O-$ repeating subunits, and wherein $\Sigma_n$ (the sum of all the n groups combined) is 4-250.

In any embodiment where polyethylene glycol is mentioned, this may refer to a polymer with a molecular weight range between 0.5-30 kDa.

In any embodiment where polyethylene glycol is mentioned, this may refer to a polymer with a molecular weight range between 2-20 kDa.

In any embodiment where polyethylene glycol is mentioned, this may refer to a polymer with a molecular weight range between 4-11 kDa.

In any embodiment where polyethylene glycol is mentioned, this may refer to a polymer with a molecular weight range between 1-6 kDa.

In any embodiment where polyethylene glycol is mentioned, this may refer to a polymer with a molecular weight range of about 2 kDa.

In any embodiment where polyethylene glycol is mentioned, this may refer to a polymer with a molecular weight range of about 5 kDa.

In any embodiment where polyethylene glycol is mentioned, this may refer to a polymer with a molecular weight range of about 10 kDa.

In any embodiment where polyethylene glycol is mentioned, this may refer to a polymer comprising $-(OCH_2CH_2)_n-$ repeating subunits where $n>3$.

In any embodiment where polyethylene glycol is mentioned, this may refer to a polymer comprising $-(OCH_2CH_2)_n-$ repeating subunits where $n>10$.

In any embodiment where polyethylene glycol is mentioned, this may refer to a polymer comprising $-(OCH_2CH_2)_n-$ repeating subunits where $n>20$.

In any embodiment where polyethylene glycol is mentioned, this may refer to a polymer comprising $-(OCH_2CH_2)_n-$ repeating subunits where $n>30$.

In any embodiment where polyethylene glycol is mentioned, this may refer to a polymer comprising $-(OCH_2CH_2)_n-$ repeating subunits where $n>50$.

In any embodiment where polyethylene glycol is mentioned, this may refer to a polymer comprising $-(OCH_2CH_2)_n-$ repeating subunits where $n>100$.

In any embodiment where polyethylene glycol is mentioned, this may refer to a polymer comprising $-(OCH_2CH_2)_n-$ repeating subunits where $n>150$.

In any embodiment where polyethylene glycol is mentioned, this may refer to a polymer comprising $-(OCH_2CH_2)_n-$ repeating subunits where $n>200$.

In any embodiment where polyethylene glycol is mentioned, this may refer to a polymer comprising $-(OCH_2CH_2)_n-$ repeating subunits where $n>250$.

In any embodiment where polyethylene glycol is mentioned, this may refer to a polymer comprising $-(OCH_2CH_2)_n-$ repeating subunits where $n<300$.

In any embodiment where polyethylene glycol is mentioned, this may refer to a polymer comprising $-(OCH_2CH_2)_n-$ repeating subunits where $n<250$.

In any embodiment where polyethylene glycol is mentioned, this may refer to a polymer comprising $-(OCH_2CH_2)_n-$ repeating subunits where $n<200$.

In any embodiment where polyethylene glycol is mentioned, this may refer to a polymer comprising $-(OCH_2CH_2)_n-$ repeating subunits where $n<150$.

In any embodiment where polyethylene glycol is mentioned, this may refer to a polymer comprising $-(OCH_2CH_2)_n-$ repeating subunits where $n<100$.

In any embodiment where polyethylene glycol is mentioned, this may refer to a polymer comprising $-(OCH_2CH_2)_n-$ repeating subunits where n<50.

In any embodiment where polyethylene glycol is mentioned, this may refer to a polymer comprising $-(OCH_2CH_2)_n-$ repeating subunits where n<40.

In any embodiment where polyethylene glycol is mentioned, this may refer to a polymer comprising $-(OCH_2CH_2)_n-$ repeating subunits where n<30.

In any embodiment where polyethylene glycol is mentioned, this may refer to a polymer comprising $-(OCH_2CH_2)_n-$ repeating subunits where n<20.

In any embodiment where polyethylene glycol is mentioned, this may refer to a polymer comprising $-(OCH_2CH_2)_n-$ repeating subunits where n<10.

Targeting Group

In a further embodiment the peptide dendrons described herein may further comprise a targeting group. Targeting groups refer to targeting moieties that binds to a cell and/or facilitates cellular internalization. The targeting group may be attached to the PEG group, optionally via a linking group, of the peptide dendron as follows:

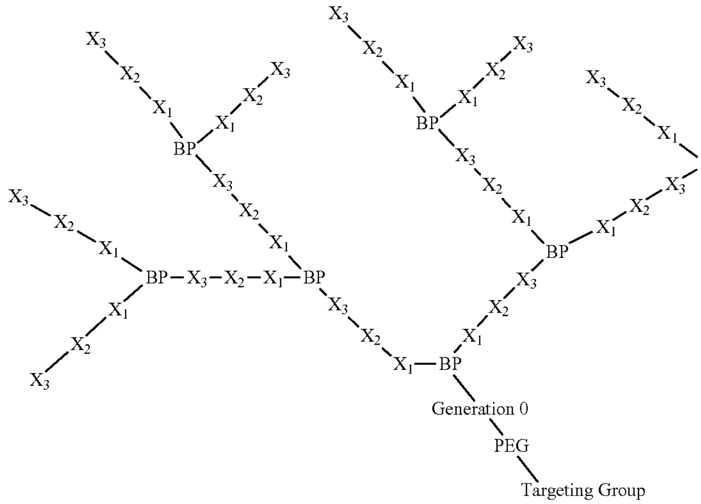

In any embodiment where a targeting group is mentioned, the targeting group may be selected from peptides, antibodies, sugars or small molecules.

Suitable targeting peptides that can be attached to the PEG group, optionally via a linking group, include:

Transferring receptor targeting peptides for example Ac-KGGGAWSIIDCSMNYCLYIEG (SEQ ID NO 3) (wherein bold "C" indicates cysteines are crosslinked via disulfide bonds) (e.g. Daas, Mohammad (2018). The Development of a Drug Delivery System Using Brain Endothelial Non-Antibody Binding Domains as Transport Carriers. Doctor of Philosophy (PhD) thesis The Open University.

Cyclic RGD peptides for example those targeting $a_3b_5$ integrins in tumors and inflamed vasculature, for example Cyclo(-Arg-Gly-Asp-D-Tyr-Lys) (SEQ ID NO 4):

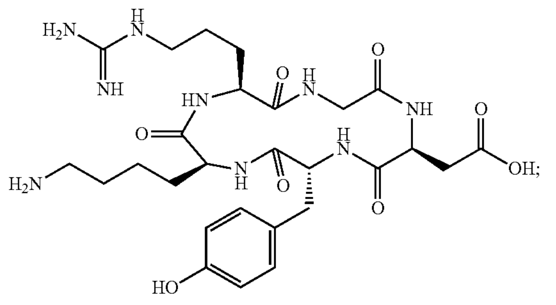 [SMILES: N=C(N)NCCC[C@@H]1NC(=O)[C@H](CCCCN)NC(=O)[C@@H](Cc2ccc(O)cc2)NC(=O)[C@H](CC(=O)O)NC(=O)CNC1=O]

and

Muscle targeting peptides for example ASSLNIA (SEQ ID NO 6) (T I Samoylova 1, B F Smith. Muscle Nerve. 1999 April; 22 (4): 460-6; doi: 10.1002/(sici) 1097-4598 (199904) 22: 4<460:: aid-mus6>3.0.co; 2-1).

Suitable targeting antibodies include:

T-cell targeting antibodies for example anti-CD3 Fab (Van Wauwe et al. J Immunol, 1980, 124 (6): 2708-2713); and Caveolae targeting antibodies for example Meca32 Monomeric FC (for example antibodies as described in Gabriela M. Marchetti, et al. Commun Biol. 2019; 2:92; Published online 2019 Mar. 7. doi: 10.1038/s42003-019-0337-2 and similar)

Suitable targeting sugars include those targeting the asialoglycoprotein receptor in the liver, for example GalNac and Tri-GalNac containing molecules for example:

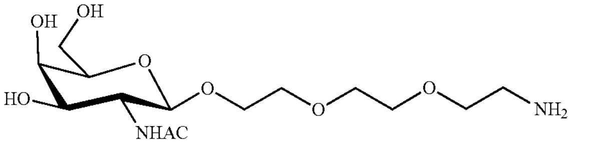

and

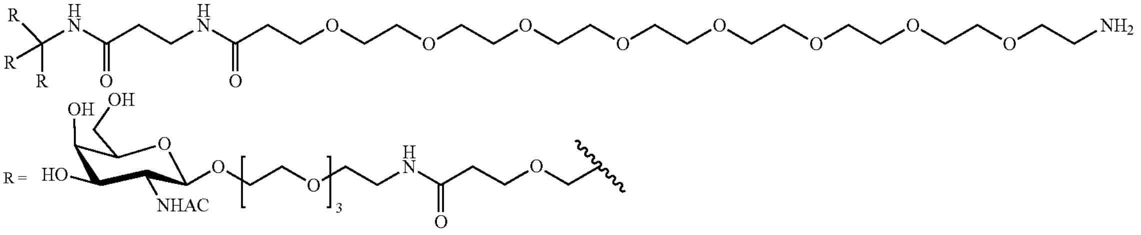

Suitable small molecule targeting agents include folate.

For some targeting groups an —SH group on the targeting group may be employed to attach to the PEG group, using similar methods to that described for attachment of a PEG group hereinabove. Typically this results in the targeting group being attached to the polyethylene glycol group via a linker group. An advantageous reagent is a bifunctional PEG reagent that may be conjugated to the peptide dendron and the targeting group via thiol chemistry. One such reagent is a PEG reagent where both ends of the molecule are functionalized with maleimidopropionate groups. A simplified version of the reaction employing a bi-functionalised polyethylene glycol group of this nature resulting in a linker group between both the PEG group and the peptide dendron and the PEG group and the targeting group may be illustrated as follows:

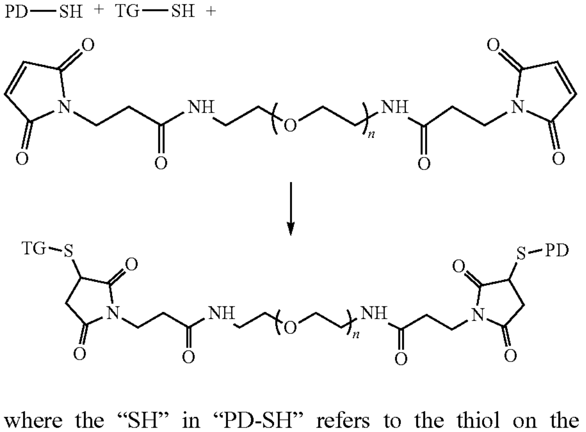

where the "SH" in "PD-SH" refers to the thiol on the cysteine side chain, "SH" in "TG-SH" refers to the reactive thiol in the targeting group, PD is the peptide dendron, TG is the targeting group, and "n" is the number of $-(OCH_2CH_2)_n-$ repeating subunits.

A peptide targeting group, or another targeting group with a reactive amine (e.g. an amine functionalised sugar) may be attached to the PEG group, using alternative activated PEG reagents. Typically this also results in the targeting group being attached to the polyethylene glycol group via a linker group. An advantageous reagent is a bifunctional PEG reagent that may be conjugated to the peptide dendron via thiol chemistry and the peptide targeting group via an amide bond. One such reagent is a PEG reagent where one end of the molecule is functionalized with maleimidopropionate group and the other with a tetrafluorophenyl (TFP) ester. A simplified version of the reaction employing a bi-functionalised polyethylene glycol group of this nature may be illustrated as follows:

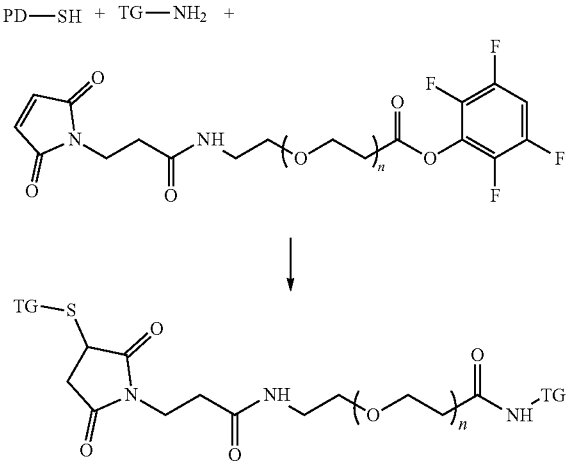

A Terminal Amino Group May Optionally be a Modified Amino Group

In one embodiment, a terminal amino group of a peptide dendron may be unmodified. An unmodified terminal amino group means it is an $-NH_2$ group.

In one embodiment, a terminal amino group of a peptide dendron may be a modified amino group.

Modifications are typically chemical modifications which include, but are not limited to, adding chemical groups, creating new bonds, and removing chemical groups. Modified amino groups are well known to those skilled in the art and include, but are not limited to, acetylation, desamino, N-lower alkyl, N-di lower alkyl, constrained alkyl (e.g., branched, cyclic, fused, adamantyl) and N-acyl modifications. Modified amino groups may also include, but are not limited to, internal amide bond involving the N-terminus (e.g. pyroGlu) protected amino groups or attaching a radiolabel, fluorescent tag or affinity tag (e.g. biotin). Modified amino groups may also include, but are not limited to, buffering groups (2-amino-6-{[6-(morpholin-4-yl)pyridine-3-carbonyl]amino}hexanoic acid; 2-amino-6-[(thiomorpholine-3-carbonyl)amino]hexanoic acid; and 2-amino-6-[2-(morpholin-4-yl)acetamido]hexanoic acid, and crosslinking groups (i.e. cylocopentadiene).

A suitable protecting group for an amino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. A particular modified amino group is acylamino. A particular modified amino group is acetylamino.

Lower alkyl is $C_{1-4}$alkyl, including t-butyl, butyl, propyl, isopropyl, ethyl and methyl.

A Terminal Carboxy Group May Optionally be a Modified Carboxy Group

In one embodiment a terminal carboxy group of a peptide dendron is unmodified. An unmodified terminal carboxy group means it is a —C(O) OH group.

In one embodiment a terminal carboxy group of a peptide dendron is a modified carboxy group.

Modifications are typically chemical modifications which include, but are not limited to, adding chemical groups, creating new bonds, and removing chemical groups. Modified carboxy group are well known to those skilled in the art and include, but are not limited to, amide, lower alkyl amide, constrained alkyl (e.g., branched, cyclic, fused, adamantyl), dialkyl amide, and lower alkyl ester modifications. Modified carboxy groups many also include, but are not limited to, protected carboxy groups or attaching a radiolabel, fluorescent tag or affinity tag (e.g. biotin), or cell-targeting ligand. A suitable protecting group for a carboxy group is, for example, an esterifying group, for example a methyl ethyl group, t-butyl group, or a benzyl group. A particular modified carboxy group is $—CO_2NH_2$. A particular modified carboxy group is C-terminal amidation. A particular modified carboxy group is a carboxamide group. A particular modified carboxy group is N—($C_{1-4}$alkyl) carbamoyl group.

Pharmaceutically Active Agents

The compositions and methods described herein are suitable for delivering pharmaceutically active agents. A pharmaceutically active agent is any substance able to exert a pharmacological effect on a human or animal body leading to a therapeutic outcome.

In any embodiment where a pharmaceutically active agent is mentioned, the pharmaceutically active agent may be selected from genetic material, chemically modified nucleic acids, oligonucleotides, therapeutic peptides, chemotherapy agents, proteins, protein conjugates, imaging agents, protein nucleic acids related to CRISPR technology, and natural virus components such as capsids, or enzymes.

In any embodiment where a pharmaceutically active agent is mentioned, the pharmaceutically active agent may be selected from genetic material.

In any embodiment where a pharmaceutically active agent is mentioned, the pharmaceutically active agent may be selected from a nucleic acid.

In any embodiment where a pharmaceutically active agent is mentioned, the pharmaceutically active agent may be selected from genetic material such as DNA or RNA.

In any embodiment where a pharmaceutically active agent is mentioned, the pharmaceutically active agent may be selected from genetic material such as DNA and RNA.

In any embodiment where a pharmaceutically active agent is mentioned, the pharmaceutically active agent may be selected from genetic material such as DNA and/or RNA.

In any embodiment where DNA is mentioned this may be plasmid, linear DNA, short, single- or double-stranded DNA, minimalized vectors such as mini-circles and mini-strings, folded DNA including hairpin and cruciform DNA, and viral derived DNA.

In any embodiment where RNA is mentioned this may be mRNA or siRNA.

In any embodiment where RNA is mentioned this may be mRNA, gRNA and/or siRNA.

In any embodiment where a pharmaceutically active agent is mentioned, the pharmaceutically active agent may be selected from DNA.

In any embodiment where a pharmaceutically active agent is mentioned, the pharmaceutically active agent may be selected from RNA.

In any embodiment where a pharmaceutically active agent is mentioned, the pharmaceutically active agent may be selected from DNA and mRNA.

In any embodiment where a pharmaceutically active agent is mentioned, the pharmaceutically active agent may be selected from mRNA and gRNA.

In any embodiment where a pharmaceutically active agent is mentioned, the pharmaceutically active agent may be selected from DNA and gRNA.

In any embodiment where a pharmaceutically active agent is mentioned, the pharmaceutically active agent may be selected from DNA and mRNA and gRNA.

In any embodiment where pharmaceutically active agent is mentioned, the pharmaceutically active agent may be selected from an oligonucleotide.

In any embodiment where oligonucleotide is mentioned this may be antisense oligonucleotides (ASO), RNA interference (RNAi), and aptamer RNAs.

In any embodiment where a pharmaceutically active agent is mentioned, the pharmaceutically active agent may be selected from chemically modified nucleic acids.

In any embodiment where a pharmaceutically active agent is mentioned, the pharmaceutically active agent may be selected from therapeutic peptides.

In any embodiment where a pharmaceutically active agent is mentioned, the pharmaceutically active agent may be selected from chemotherapy agents.

In any embodiment where a pharmaceutically active agent is mentioned, the pharmaceutically active agent may be selected from proteins.

In any embodiment where a pharmaceutically active agent is mentioned, the pharmaceutically active agent may be selected from protein conjugates.

In any embodiment where a pharmaceutically active agent is mentioned, the pharmaceutically active agent may be selected from imaging agents.

In any embodiment where a pharmaceutically active agent is mentioned, the pharmaceutically active agent may be selected from protein nucleic acids related to CRISPR technology.

In any embodiment where a pharmaceutically active agent is mentioned, the pharmaceutically active agent may be selected from DNA, gRNA and/or mRNA related to CRISPR technology.

In any embodiment where a pharmaceutically active agent is mentioned, the pharmaceutically active agent may be selected from natural virus components such as capsids, or enzymes.

In any embodiment where a pharmaceutically active agent is mentioned, the pharmaceutically active agent may be selected from nucleic acids (i.e. plasmids and mRNA) that encode therapeutic proteins such as monoclonal antibodies, for example, abciximab, adalimumab, alefacept, alemtuzumab, basiliximab, belimumab, bezlotoxumab, canakinumab, certolizumab pegol, cetuximab, daclizumab, denosumab, efalizumab, golimumab, inflectra, ipilimumab, ixekizumab, natalizumab, nivolumab, olaratumab, omalizumab, palivizumab, panitumumab, pembrolizumab, rituximab, tocilizumab, trastuzumab, secukinumab, and ustekinumab; enzymes, for example, agalsidase beta, imiglucerase, velaglucerase alfa, taliglucerase, alglucosidase alfa, alglucosidase alfa, laronidase, idursulfase intravenous, and galsulfase; growth factors; and cytokines, for example IL-2 and IFN-α.

In any embodiment where a pharmaceutically active agent is mentioned, the pharmaceutically active agent may be selected from nucleic acids (i.e. plasmids and mRNA) that encode therapeutic proteins such as monoclonal antibodies; enzymes; growth factors; and cytokines.

In any embodiment where a pharmaceutically active agent is mentioned, the pharmaceutically active agent may be selected from nucleic acids (i.e. plasmids and mRNA) that encode therapeutic proteins such as monoclonal antibodies; enzymes; growth factors; transcription factors; and cytokines.

In any embodiment where a pharmaceutically active agent is mentioned, the pharmaceutically active agent may be selected from nucleic acids (i.e. plasmids and mRNA) that encode monoclonal antibodies.

In any embodiment where a pharmaceutically active agent is mentioned, the pharmaceutically active agent may be selected from nucleic acids (i.e. plasmids and mRNA) that encode MEDI8852 and STK11.

In any embodiment where a pharmaceutically active agent is mentioned, the pharmaceutically active agent may be selected from nucleic acids (i.e. plasmids and mRNA) that encode monoclonal antibodies selected from abciximab, adalimumab, alefacept, alemtuzumab, basiliximab, belimumab, bezlotoxumab, canakinumab, certolizumab pegol, cetuximab, daclizumab, denosumab, efalizumab, golimumab, inflectra, ipilimumab, ixekizumab, natalizumab, nivolumab, olaratumab, omalizumab, palivizumab, panitumumab, pembrolizumab, rituximab, tocilizumab, trastuzumab, secukinumab, and ustekinumab.

In any embodiment where a pharmaceutically active agent is mentioned, the pharmaceutically active agent may be selected from nucleic acids (i.e. plasmids and mRNA) that encode enzymes.

In any embodiment where a pharmaceutically active agent is mentioned, the pharmaceutically active agent may be selected from nucleic acids (i.e. plasmids and mRNA) that encode enzymes selected from agalsidase beta, imiglucerase, velaglucerase alfa, taliglucerase, alglucosidase alfa, alglucosidase alfa, laronidase, idursulfase intravenous, and galsulfase.

In any embodiment where a pharmaceutically active agent is mentioned, the pharmaceutically active agent may be selected from nucleic acids (i.e. plasmids and mRNA) that encode growth factors.

In any embodiment where a pharmaceutically active agent is mentioned, the pharmaceutically active agent may be selected from nucleic acids (i.e. plasmids and mRNA) that encode transcription factors.

In any embodiment where a pharmaceutically active agent is mentioned, the pharmaceutically active agent may be selected from nucleic acids (i.e. plasmids and mRNA) that encode the transcription factor HNF-4α.

In any embodiment where a pharmaceutically active agent is mentioned, the pharmaceutically active agent may be selected from nucleic acids (i.e. plasmids and mRNA) that encode cytokines.

In any embodiment where a pharmaceutically active agent is mentioned, the pharmaceutically active agent may be selected from nucleic acids (i.e. plasmids and mRNA) that encode cytokines selected from IL-2 and IFN-α.

In any embodiment where a pharmaceutically active agent is mentioned, the pharmaceutically active agent may be selected from siRNA.

In any embodiment where a pharmaceutically active agent is mentioned, the pharmaceutically active agent may be selected from mRNA.

In any embodiment where a pharmaceutically active agent is mentioned, the pharmaceutically active agent may be selected from gRNA.

In any embodiment where a pharmaceutically active agent is mentioned, the pharmaceutically active agent may be selected from siRNA used to reduce protein expression in applications including regulation of oncogene, growth factor, and cytokine expression.

In any embodiment where a pharmaceutically active agent is selected from a nucleic acid, the ratio of peptide dendron basic amino acid residues:nucleic acid phosphate (N:P) is about 2:1.

In any embodiment where a pharmaceutically active agent is selected from a nucleic acid, the ratio of peptide dendron basic amino acid residues:nucleic acid phosphate (N:P) is about 4:1.

In any embodiment where a pharmaceutically active agent is selected from a nucleic acid, the ratio of peptide dendron basic amino acid residues:nucleic acid phosphate (N:P) is about 6:1.

In any embodiment where a pharmaceutically active agent is selected from DNA, the ratio of peptide dendron basic amino acid residues:DNA phosphate (N:P) is about 2:1.

In any embodiment where a pharmaceutically active agent is selected from DNA, the ratio of peptide dendron basic amino acid residues:DNA phosphate (N:P) is about 4:1.

In any embodiment where a pharmaceutically active agent is selected from DNA, the ratio of peptide dendron basic amino acid residues:DNA phosphate (N:P) is about 6:1.

In any embodiment where a pharmaceutically active agent is selected from RNA, the ratio of peptide dendron basic amino acid residues:RNA phosphate (N:P) is about 2:1.

In any embodiment where a pharmaceutically active agent is selected from RNA, the ratio of peptide dendron basic amino acid residues:RNA phosphate (N:P) is about 4:1.

In any embodiment where a pharmaceutically active agent is selected from RNA, the ratio of peptide dendron basic amino acid residues:RNA phosphate (N:P) is about 6:1.

In any embodiment where a pharmaceutically active agent is selected from RNA, the ratio of peptide dendron basic amino acid residues:DNA and RNA phosphate (N:P) is about 2:1.

In any embodiment where a pharmaceutically active agent is selected from RNA, the ratio of peptide dendron basic amino acid residues:DNA and RNA phosphate (N:P) is about 4:1.

In any embodiment where a pharmaceutically active agent is selected from RNA, the ratio of peptide dendron basic amino acid residues:DNA and RNA phosphate (N:P) is about 6:1.

Pharmaceutical Delivery System

In one embodiment there is provided a pharmaceutical delivery system which comprises a peptide dendron comprising one or more residues derived from a modified lysine as described herein. A pharmaceutical delivery system is a delivery system that may be employed to deliver a pharmaceutically active agent into a human or animal body, for example into a cell.

In one embodiment there is provided the use of a peptide dendron comprising one or more residues derived from a modified lysine as described herein in a pharmaceutical delivery system.

In one embodiment there is provided a peptide dendron comprising one or more residues derived from a modified lysine as described herein for use as a pharmaceutical delivery system.

In one embodiment there is provided a delivery system for a pharmaceutically active agent which comprises a peptide dendron comprising one or more residues derived from a modified lysine as described herein.

In one embodiment a pharmaceutical delivery system as described herein may comprise one or more different peptide dendrons, for example two different peptide dendrons. A mixture of peptide dendrons may be employed to incorporate targeting moieties, stabilize the nanoparticle, and/or synergistically combine different properties.

In one embodiment there is provided a pharmaceutical delivery system which comprises one or more peptide dendrons as described herein.

In any embodiment where "one or more peptide dendrons" is referred to, this may refer to one peptide dendron.

In any embodiment where "one or more peptide dendrons" is referred to, this may refer to two different peptide dendrons.

In any embodiment where "one or more peptide dendrons" is referred to, this may refer to more than one different peptide dendrons.

In one embodiment there is provided a delivery system for a pharmaceutically active agent which comprises one or more peptide dendrons as described herein.

In one embodiment a pharmaceutical delivery system as described herein may comprise a peptide dendron comprising a polyethylene glycol group, and a peptide dendron comprising both a polyethylene glycol group and a targeting group.

In one embodiment a pharmaceutical delivery system as described herein may comprise a ratio of peptide dendrons comprising a polyethylene glycol group:peptide dendrons comprising both a polyethylene glycol group and a targeting group of about 1:50.

In one embodiment a pharmaceutical delivery system as described herein may comprise a ratio of peptide dendrons comprising a polyethylene glycol group:peptide dendrons comprising both a polyethylene glycol group and a targeting group of more than 1:50.

In one embodiment a pharmaceutical delivery system as described herein may comprise a ratio of peptide dendrons comprising a polyethylene glycol group:peptide dendrons comprising both a polyethylene glycol group and a targeting group of less than 1:50.

In one embodiment a pharmaceutical delivery system as described herein may comprise a ratio of peptide dendrons comprising a polyethylene glycol group:peptide dendrons comprising both a polyethylene glycol group and a targeting group of about 1:20.

In one embodiment a pharmaceutical delivery system as described herein may comprise a ratio of peptide dendrons comprising a polyethylene glycol group:peptide dendrons comprising both a polyethylene glycol group and a targeting group of more than 1:20.

In one embodiment a pharmaceutical delivery system as described herein may comprise a ratio of peptide dendrons comprising a polyethylene glycol group:peptide dendrons comprising both a polyethylene glycol group and a targeting group of less than 1:20.

In one embodiment a pharmaceutical delivery system as described herein may comprise a ratio of peptide dendrons comprising a polyethylene glycol group:peptide dendrons comprising both a polyethylene glycol group and a targeting group of about 1:15.

In one embodiment a pharmaceutical delivery system as described herein may comprise a ratio of peptide dendrons comprising a polyethylene glycol group:peptide dendrons comprising both a polyethylene glycol group and a targeting group of more than 1:15.

In one embodiment a pharmaceutical delivery system as described herein may comprise a ratio of peptide dendrons comprising a polyethylene glycol group:peptide dendrons comprising both a polyethylene glycol group and a targeting group of less than 1:15.

In one embodiment a pharmaceutical delivery system as described herein may comprise a ratio of peptide dendrons comprising a polyethylene glycol group:peptide dendrons comprising both a polyethylene glycol group and a targeting group of about 1:10.

In one embodiment a pharmaceutical delivery system as described herein may comprise a ratio of peptide dendrons comprising a polyethylene glycol group:peptide dendrons comprising both a polyethylene glycol group and a targeting group of more than 1:10.

In one embodiment a pharmaceutical delivery system as described herein may comprise a ratio of peptide dendrons comprising a polyethylene glycol group:peptide dendrons comprising both a polyethylene glycol group and a targeting group of less than 1:10.

In one embodiment a pharmaceutical delivery system as described herein may comprise a ratio of peptide dendrons comprising a polyethylene glycol group:peptide dendrons comprising both a polyethylene glycol group and a targeting group of about 1:5.

In one embodiment a pharmaceutical delivery system as described herein may comprise a ratio of peptide dendrons comprising a polyethylene glycol group:peptide dendrons comprising both a polyethylene glycol group and a targeting group of more than 1:5.

In one embodiment a pharmaceutical delivery system as described herein may comprise a ratio of peptide dendrons comprising a polyethylene glycol group:peptide dendrons comprising both a polyethylene glycol group and a targeting group of less than 1:5.

In one embodiment a pharmaceutical delivery system as described herein may comprise a ratio of peptide dendrons comprising a polyethylene glycol group:peptide dendrons comprising both a polyethylene glycol group and a targeting group of about 2:4.

In one embodiment a pharmaceutical delivery system as described herein may comprise a ratio of peptide dendrons comprising a polyethylene glycol group:peptide dendrons comprising both a polyethylene glycol group and a targeting group of more than 2:4.

In one embodiment a pharmaceutical delivery system as described herein may comprise a ratio of peptide dendrons comprising a polyethylene glycol group:peptide dendrons comprising both a polyethylene glycol group and a targeting group of less than 2:4.

In one embodiment a pharmaceutical delivery system as described herein may comprise a ratio of peptide dendrons comprising a polyethylene glycol group:peptide dendrons comprising both a polyethylene glycol group and a targeting group of about 1:1.

In one embodiment a pharmaceutical delivery system as described herein may comprise a ratio of peptide dendrons comprising a polyethylene glycol group:peptide dendrons comprising both a polyethylene glycol group and a targeting group of about 4:2.

In one embodiment a pharmaceutical delivery system as described herein may comprise a ratio of peptide dendrons comprising a polyethylene glycol group:peptide dendrons comprising both a polyethylene glycol group and a targeting group of more than 4:2.

In one embodiment a pharmaceutical delivery system as described herein may comprise a ratio of peptide dendrons comprising a polyethylene glycol group:peptide dendrons comprising both a polyethylene glycol group and a targeting group of less than 4:2.

In one embodiment a pharmaceutical delivery system as described herein may comprise a ratio of peptide dendrons comprising a polyethylene glycol group:peptide dendrons comprising both a polyethylene glycol group and a targeting group of about 5:1.

In one embodiment a pharmaceutical delivery system as described herein may comprise a ratio of peptide dendrons comprising a polyethylene glycol group:peptide dendrons comprising both a polyethylene glycol group and a targeting group of more than 5:1.

In one embodiment a pharmaceutical delivery system as described herein may comprise a ratio of peptide dendrons comprising a polyethylene glycol group:peptide dendrons comprising both a polyethylene glycol group and a targeting group of less than 5:1.

In one embodiment a pharmaceutical delivery system as described herein may comprise a ratio of peptide dendrons comprising a polyethylene glycol group:peptide dendrons comprising both a polyethylene glycol group and a targeting group of about 10:1.

In one embodiment a pharmaceutical delivery system as described herein may comprise a ratio of peptide dendrons comprising a polyethylene glycol group:peptide dendrons comprising both a polyethylene glycol group and a targeting group of more than 10:1.

In one embodiment a pharmaceutical delivery system as described herein may comprise a ratio of peptide dendrons comprising a polyethylene glycol group:peptide dendrons comprising both a polyethylene glycol group and a targeting group of less than 10:1.

In one embodiment a pharmaceutical delivery system as described herein may comprise a ratio of peptide dendrons comprising a polyethylene glycol group:peptide dendrons comprising both a polyethylene glycol group and a targeting group of about 15:1.

In one embodiment a pharmaceutical delivery system as described herein may comprise a ratio of peptide dendrons comprising a polyethylene glycol group:peptide dendrons comprising both a polyethylene glycol group and a targeting group of more than 15:1.

In one embodiment a pharmaceutical delivery system as described herein may comprise a ratio of peptide dendrons comprising a polyethylene glycol group:peptide dendrons comprising both a polyethylene glycol group and a targeting group of less than 15:1.

In one embodiment a pharmaceutical delivery system as described herein may comprise a ratio of peptide dendrons comprising a polyethylene glycol group:peptide dendrons comprising both a polyethylene glycol group and a targeting group of about 20:1.

In one embodiment a pharmaceutical delivery system as described herein may comprise a ratio of peptide dendrons comprising a polyethylene glycol group:peptide dendrons comprising both a polyethylene glycol group and a targeting group of more than 20:1.

In one embodiment a pharmaceutical delivery system as described herein may comprise a ratio of peptide dendrons comprising a polyethylene glycol group:peptide dendrons comprising both a polyethylene glycol group and a targeting group of less than 20:1.

In one embodiment a pharmaceutical delivery system as described herein may comprise a ratio of peptide dendrons comprising a polyethylene glycol group:peptide dendrons comprising both a polyethylene glycol group and a targeting group of about 50:1.

In one embodiment a pharmaceutical delivery system as described herein may comprise a ratio of peptide dendrons comprising a polyethylene glycol group:peptide dendrons comprising both a polyethylene glycol group and a targeting group of more than 50:1.

In one embodiment a pharmaceutical delivery system as described herein may comprise a ratio of peptide dendrons comprising a polyethylene glycol group:peptide dendrons comprising both a polyethylene glycol group and a targeting group of less than 50:1.

Peptide dendrons as described herein and a pharmaceutically active agent may be combined while gently mixing in a physiologically isotonic buffer (e.g. 5% trehalose or sucrose, 20 mM HEPES, or phosphate buffered saline (PBS) to form nanoparticles. These formulations may be delivered immediately, stored at 4° C., or lyophilized for long term storage.

Peptide dendrons as described herein may be prepared in a form suitable for oral administration, for example as a tablet or capsule, for parenteral injection (including intravenous, subcutaneous, intradermal, intramuscular, intravascular or infusion), for topical administration as an ointment or cream or for rectal administration as a suppository. In particular, peptide dendrons as described herein may be prepared in a form suitable for injection e.g. by intravenous, subcutaneous, intradermal, or intramuscular injection.

Further Excipients

In one embodiment further excipients may be added to the formulations and compositions comprising one or more peptide dendrons and pharmaceutically active agents described herein. These may enhance nanoparticle stability and enhance nucleic acid packaging, resulting in improvements in cellular delivery and transfection.

In one embodiment there is provided a formulation comprising one or more peptide dendrons, as described herein, and a lipid.

In one embodiment there is provided a formulation comprising one or more peptide dendrons, as described herein, and a lipid selected from 1:1 (w/w) N-[1-(2,3-dioleyloxy) propyl]-n,n,n-trimethylammonium chloride (DOTMA) and dioleoyl phophotidylethanolamine (DOPE).

In one embodiment there is provided a formulation comprising one or more peptide dendrons, as described herein, and a lipid selected from a mixture of N-[1-(2,3-dioleyloxy)

propyl]-n,n,n-trimethylammonium chloride (DOTMA) and dioleoyl phophotidylethanolamine (DOPE), (6Z,9Z,28Z,31Z)-heptatriacont-6,9,28,31-tetraene-19-yl 4-(dimethyl-amino) butanoate (MC3), distearoylphosphatidylcholine (DSPC), dimyristoyl glycerol (DMG), and heptadecan-9-yl 8-((2-hydroxyethyl) (6-oxo-6-(undecyloxy) hexyl)amino) octanoate (SM-102) or cholesterol.

Uses

Peptide dendrons as described herein may be used to deliver a pharmaceutically active agent suitable to treat a broad range of ailments including metabolic disorders, immunological disorders, hormonal disorders, cancer, hematological disorders, genetic disorders, infectious disease, cardiac disease, bone disorders, respiratory disorders, neurological disorders, adjunct therapy, eye disorders, malabsorption disorders. Therapeutic application may include: systemic expression of proteins (i.e. antibodies for virus treatment) or targeted delivery (i.e. metastatic tumours, in vivo CAR-T).

In one embodiment there is provided a pharmaceutical delivery system which comprises one or more peptide dendrons as described herein for use in therapy.

In one embodiment there is provided a delivery system for a pharmaceutically active agent which comprises one or more peptide dendrons as described herein for use in therapy.

In one embodiment there is provided a peptide dendron for use in delivering a pharmaceutically active agent to a cell.

In one embodiment there is provided a pharmaceutical delivery system which comprises one or more peptide dendrons as described herein for use in the treatment of metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders.

In one embodiment there is provided a delivery system for a pharmaceutically active agent which comprises one or more peptide dendrons as described herein for use in the treatment of metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders.

In one embodiment there is provided a delivery system for a pharmaceutically active agent which comprises one or more peptide dendrons as described herein for use in gene therapy.

As used herein, the terms "treatment" and "treat" refer to reversing, alleviating, delaying the onset of, or inhibiting the progress of a disease or disorder, or one or more symptoms thereof, as described herein. In some embodiments, treatment may be conducted after one or more symptoms have developed. In other embodiments, treatment may be conducted in the absence of symptoms. For example, treatment may be conducted to a susceptible individual prior to the onset of symptoms (e.g. in light of a history of symptoms and/or in light of genetic or other susceptibility factors). Treatment may also be continued after symptoms have resolved, for example to present or delay their recurrence.

Pharmaceutical Compositions

In one embodiment there is provided a pharmaceutical composition which comprises one or more peptide dendrons as described herein.

In any embodiment where a pharmaceutical composition comprises one or more peptide dendrons the pharmaceutical composition may comprise one peptide dendron.

In any embodiment where a pharmaceutical composition comprises "one or more peptide dendrons" the pharmaceutical composition may comprise more than one different peptide dendrons.

In any embodiment where a pharmaceutical composition comprises "one or more peptide dendrons" the pharmaceutical composition may comprise two different peptide dendrons.

In any embodiment where a pharmaceutical composition comprises "one or more peptide dendrons" the pharmaceutical composition may comprise at least two different peptide dendrons.

In one embodiment there is provided a pharmaceutical composition which comprises one or more peptide dendrons as described herein and a pharmaceutically active agent.

In one embodiment there is provided a pharmaceutical composition which comprises one or more peptide dendrons as described herein.

In one embodiment there is provided a pharmaceutical composition which comprises two or more different peptide dendrons.

In one embodiment there is provided a composition comprising a pharmaceutically active agent and one or more peptide dendrons as described herein.

In one embodiment a pharmaceutical composition as described herein may comprise a peptide dendron comprising a polyethylene glycol group, and a peptide dendron comprising both a polyethylene glycol group and a targeting group.

In one embodiment a pharmaceutical composition as described herein may comprise a ratio of peptide dendrons comprising a polyethylene glycol group:peptide dendrons comprising both a polyethylene glycol group and a targeting group of about 1:50.

In one embodiment a pharmaceutical composition as described herein may comprise a ratio of peptide dendrons comprising a polyethylene glycol group:peptide dendrons comprising both a polyethylene glycol group and a targeting group of more than 1:50.

In one embodiment a pharmaceutical composition as described herein may comprise a ratio of peptide dendrons comprising a polyethylene glycol group:peptide dendrons comprising both a polyethylene glycol group and a targeting group of less than 1:50.

In one embodiment a pharmaceutical composition as described herein may comprise a ratio of peptide dendrons comprising a polyethylene glycol group:peptide dendrons comprising both a polyethylene glycol group and a targeting group of about 1:20.

In one embodiment a pharmaceutical composition as described herein may comprise a ratio of peptide dendrons comprising a polyethylene glycol group:peptide dendrons comprising both a polyethylene glycol group and a targeting group of more than 1:20.

In one embodiment a pharmaceutical composition as described herein may comprise a ratio of peptide dendrons comprising a polyethylene glycol group:peptide dendrons comprising both a polyethylene glycol group and a targeting group of less than 1:20.

In one embodiment a pharmaceutical composition as described herein may comprise a ratio of peptide dendrons comprising a polyethylene glycol group:peptide dendrons comprising both a polyethylene glycol group and a targeting group of about 1:15.

In one embodiment a pharmaceutical composition as described herein may comprise a ratio of peptide dendrons comprising a polyethylene glycol group:peptide dendrons comprising both a polyethylene glycol group and a targeting group of more than 1:15.

In one embodiment a pharmaceutical composition as described herein may comprise a ratio of peptide dendrons comprising a polyethylene glycol group:peptide dendrons comprising both a polyethylene glycol group and a targeting group of less than 1:15.

In one embodiment a pharmaceutical composition as described herein may comprise a ratio of peptide dendrons comprising a polyethylene glycol group:peptide dendrons comprising both a polyethylene glycol group and a targeting group of about 1:10.

In one embodiment a pharmaceutical composition as described herein may comprise a ratio of peptide dendrons comprising a polyethylene glycol group:peptide dendrons comprising both a polyethylene glycol group and a targeting group of more than 1:10.

In one embodiment a pharmaceutical composition as described herein may comprise a ratio of peptide dendrons comprising a polyethylene glycol group:peptide dendrons comprising both a polyethylene glycol group and a targeting group of less than 1:10.

In one embodiment a pharmaceutical composition as described herein may comprise a ratio of peptide dendrons comprising a polyethylene glycol group:peptide dendrons comprising both a polyethylene glycol group and a targeting group of about 1:5.

In one embodiment a pharmaceutical composition as described herein may comprise a ratio of peptide dendrons comprising a polyethylene glycol group:peptide dendrons comprising both a polyethylene glycol group and a targeting group of more than 1:5.

In one embodiment a pharmaceutical composition as described herein may comprise a ratio of peptide dendrons comprising a polyethylene glycol group:peptide dendrons comprising both a polyethylene glycol group and a targeting group of less than 1:5.

In one embodiment a pharmaceutical composition as described herein may comprise a ratio of peptide dendrons comprising a polyethylene glycol group:peptide dendrons comprising both a polyethylene glycol group and a targeting group of about 2:4.

In one embodiment a pharmaceutical composition as described herein may comprise a ratio of peptide dendrons comprising a polyethylene glycol group:peptide dendrons comprising both a polyethylene glycol group and a targeting group of more than 2:4.

In one embodiment a pharmaceutical composition as described herein may comprise a ratio of peptide dendrons comprising a polyethylene glycol group:peptide dendrons comprising both a polyethylene glycol group and a targeting group of less than 2:4.

In one embodiment a pharmaceutical composition as described herein may comprise a ratio of peptide dendrons comprising a polyethylene glycol group:peptide dendrons comprising both a polyethylene glycol group and a targeting group of about 1:1.

In one embodiment a pharmaceutical composition as described herein may comprise a ratio of peptide dendrons comprising a polyethylene glycol group:peptide dendrons comprising both a polyethylene glycol group and a targeting group of about 4:2.

In one embodiment a pharmaceutical composition as described herein may comprise a ratio of peptide dendrons comprising a polyethylene glycol group:peptide dendrons comprising both a polyethylene glycol group and a targeting group of more than 4:2.

In one embodiment a pharmaceutical composition as described herein may comprise a ratio of peptide dendrons comprising a polyethylene glycol group:peptide dendrons comprising both a polyethylene glycol group and a targeting group of less than 4:2.

In one embodiment a pharmaceutical composition as described herein may comprise a ratio of peptide dendrons comprising a polyethylene glycol group:peptide dendrons comprising both a polyethylene glycol group and a targeting group of about 5:1.

In one embodiment a pharmaceutical composition as described herein may comprise a ratio of peptide dendrons comprising a polyethylene glycol group:peptide dendrons comprising both a polyethylene glycol group and a targeting group of more than 5:1.

In one embodiment a pharmaceutical composition as described herein may comprise a ratio of peptide dendrons comprising a polyethylene glycol group:peptide dendrons comprising both a polyethylene glycol group and a targeting group of less than 5:1.

In one embodiment a pharmaceutical composition as described herein may comprise a ratio of peptide dendrons comprising a polyethylene glycol group:peptide dendrons comprising both a polyethylene glycol group and a targeting group of about 10:1.

In one embodiment a pharmaceutical composition as described herein may comprise a ratio of peptide dendrons comprising a polyethylene glycol group:peptide dendrons comprising both a polyethylene glycol group and a targeting group of more than 10:1.

In one embodiment a pharmaceutical composition as described herein may comprise a ratio of peptide dendrons comprising a polyethylene glycol group:peptide dendrons comprising both a polyethylene glycol group and a targeting group of less than 10:1.

In one embodiment a pharmaceutical composition as described herein may comprise a ratio of peptide dendrons comprising a polyethylene glycol group:peptide dendrons comprising both a polyethylene glycol group and a targeting group of about 15:1.

In one embodiment a pharmaceutical composition as described herein may comprise a ratio of peptide dendrons comprising a polyethylene glycol group:peptide dendrons comprising both a polyethylene glycol group and a targeting group of more than 15:1.

In one embodiment a pharmaceutical composition as described herein may comprise a ratio of peptide dendrons comprising a polyethylene glycol group:peptide dendrons comprising both a polyethylene glycol group and a targeting group of less than 15:1.

In one embodiment a pharmaceutical composition as described herein may comprise a ratio of peptide dendrons comprising a polyethylene glycol group:peptide dendrons comprising both a polyethylene glycol group and a targeting group of about 20:1.

In one embodiment a pharmaceutical composition as described herein may comprise a ratio of peptide dendrons comprising a polyethylene glycol group:peptide dendrons comprising both a polyethylene glycol group and a targeting group of more than 20:1.

In one embodiment a pharmaceutical composition as described herein may comprise a ratio of peptide dendrons comprising a polyethylene glycol group:peptide dendrons comprising both a polyethylene glycol group and a targeting group of less than 20:1.

In one embodiment a pharmaceutical composition as described herein may comprise a ratio of peptide dendrons comprising a polyethylene glycol group:peptide dendrons comprising both a polyethylene glycol group and a targeting group of about 50:1.

In one embodiment a pharmaceutical composition as described herein may comprise a ratio of peptide dendrons comprising a polyethylene glycol group:peptide dendrons comprising both a polyethylene glycol group and a targeting group of more than 50:1.

In one embodiment a pharmaceutical composition as described herein may comprise a ratio of peptide dendrons comprising a polyethylene glycol group:peptide dendrons comprising both a polyethylene glycol group and a targeting group of less than 50:1.

In one embodiment there is provided a pharmaceutical composition comprising one or more peptide dendrons as described herein for use in therapy.

In one embodiment there is provided a pharmaceutical composition comprising one or more peptide dendrons as described herein and a pharmaceutically active agent for use in therapy.

In one embodiment there is provided a pharmaceutical composition which comprises one or more peptide dendrons as described herein for use in the treatment of metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders.

In one embodiment there is provided a pharmaceutical composition which comprises one or more peptide dendrons as described herein and a pharmaceutically active agent for use in the treatment of metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders.

In one embodiment there is provided a pharmaceutical composition which comprises one or more peptide dendrons as described herein and a pharmaceutically active agent for use in gene therapy.

In one embodiment there is provided a pharmaceutical composition which comprises one or more peptide dendrons as described herein for use in gene therapy.

Methods of Treatment

In one embodiment there is provided a method of treating metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders which comprises administering to said animal an effective amount of a pharmaceutical composition comprising one or more peptide dendrons as described herein.

In one embodiment there is provided a method of treating metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders which comprises administering to said animal an effective amount of a pharmaceutical composition comprising one or more peptide dendrons as described herein and a pharmaceutically active agent.

In one embodiment there is provided a method of gene therapy which comprises administering one or more peptide dendrons as described herein.

In one embodiment there is provided a method of gene therapy which comprises administering one or more peptide dendrons as described herein and a pharmaceutically active agent.

Use of Pharmaceutical Compositions

In one embodiment there is provided the use of a pharmaceutical composition which comprises one or more peptide dendrons as described herein in the manufacture of a medicament for the treatment of metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders.

In one embodiment there is provided the use of a pharmaceutical composition which comprises one or more peptide dendrons as described herein and a pharmaceutically active agent in the manufacture of a medicament for the treatment of metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders.

In one embodiment there is provided the use of a pharmaceutical composition which comprises one or more peptide dendrons as described herein in gene therapy.

In one embodiment there is provided the use of a pharmaceutical composition which comprises one or more peptide dendrons as described herein and a pharmaceutically active agent in gene therapy.

Kits

In one embodiment there is provided a kit comprising:

a) one or more peptide dendrons as described herein in a first unit;
b) a pharmaceutically active agent in a second unit; and
c) container means for containing said first and second units.

In one embodiment there is provided a kit comprising:

a) one or more peptide dendrons as described herein in a first unit;
b) a pharmaceutically active agent in a second unit; and
c) container means for containing said first and second units.
d) instructions for use.

BRIEF DESCRIPTION OF THE FIGURES

In FIG. 3C, two different NP formulations PD3(MN) and PD3(TM) were screened in various cell lines (H1299, C2C12, HEK393, and HEPG2) to identify the top performers for different applications. These results show that the MN modification was superior in lung (H1299; human non-small cell lung carcinoma cell line derived from the lymph) and muscle cells (C2C12; mouse myoblasts). Alternatively, the TM modification performed best in cell lines derived from filtration organs including the kidney (HEK393; Human embryonic kidney cells) and liver (HEPG2; human hepatoma cell line).

FIG. 5A shows the results with anti-Flu mAb MEDI8852 and FIG. 5B shows the results with tumor suppressor serine/threonine kinase 11 (STK11). MEDI8852 was quantified via indirect ELISA and expression levels was collected in triplicate and presented as the mean+/−standard deviation. Mass spectrometry was used as additional confirmation of expression. STK11 was quantified using western blots. The goal of the NPs is to express therapeutic proteins using the host's cells. These results shows the NPs have the capacity to express a diverse range of therapeutics including mAbs (i.e. MEDI8852 (Anti-flu mAb)) and enzymes (i.e. Tumor inhibitor serine/threonine kinase 11 (STK11)) in vivo in the cell lines of interest for the therapeutics mode of action.

EXAMPLES

Abbreviations Used Herein

Figure 1:
FIG. 1: A representative schematic representation of the synthesis of peptide dendrons (PD) as described in Example 2.

NP: Nanoparticle;

PD: Peptide Dendron;

PDID: Peptide Dendron Intercellular Delivery

Amino acid "CIT": Citrulline.

The following abbreviations are used herein for the modified Lysines:

LYS(MN) or K(MN)

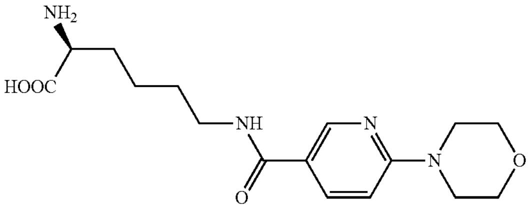

LYS(TM) or K(TM)

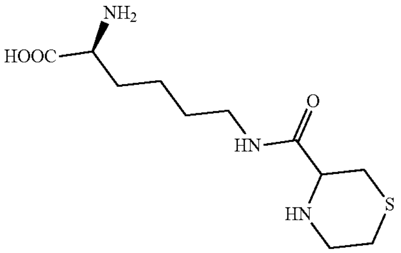

LYS(M) or K(M)

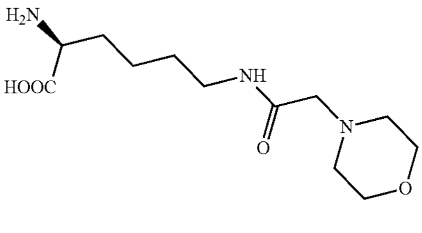

The following polymers and ligands were incorporated into the peptide dendrons:

TABLE 1

Summary of Targeting Moieties incorporated into the PD.

| No | Name | Structure | Point of attachment to PEG containing group |
|---|---|---|---|
| 1 | MeO PEG | m-dPEG ®$_{36}$-MAL; Quanta BioDesign, Plain City Ohio | N/A |
| 2 | Mal-PEG | Bis-Mal-PEG$_{19}$ (BroadPharm, San Diego, CA) | N/A |
| 3 | TfR | Ac-KGGGAWSIID**C**SMNY**C**LYIEG (SEQ ID NO 3, wherein bold "**C**" indicates cysteines are crosslinked via disulfide bonds) | Lysine ε-amine |
| 4 | cRGD | Cyclo(-Arg-Gly-Asp-D-Tyr-Lys) (SEQ ID NO 4) | Lysine ε-amine |
| 5 | Anti-CD3 | Van Wauwe et al. J Immunol, 1980, 124(6): 2708-2713 | cyclopentadiene |
| 6 | Meca32 | Modified from Gabriela M. Marchetti, et al. Commun Biol. 2019; 2: 92; Published online 2019 Mar 7. doi: 10.1038/s42003-019-0337-2 | cyclopentadiene |
| 7 | GalNac | N-Acetylgalactosamine Ligand: β-GalNAc-PEG3-Amine (Sussex Research, Ontario Canada) | Amine |
| 8 | Tri-GalNac | 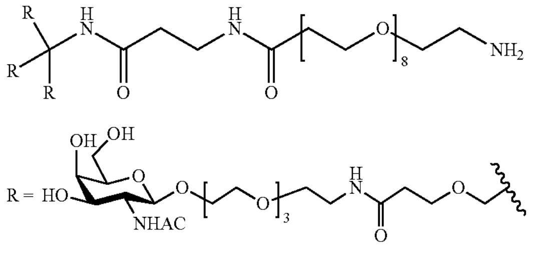 (Sussex Research, Ontario Canada) | Amine |

Example 1

Preparation of Modified Lysines

Method 1: Synthesis of 1-{[(morpholin-4-yl)acetyl]oxy}pyrrolidine-2,5-dione

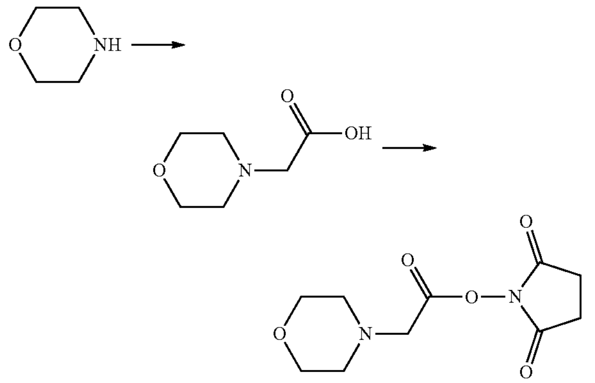

(Morpholin-4-yl) acetic acid (1 g, 6.89 mmol) was dissolved in dichloromethane (DCM) (25 mL) and N-hydroxysuccinimide (NHS) (872 mg, 7.58 mmol) and N-ethyl-N'-(3-dimethylaminopropyl) carbodiimide hydrochloride (EDC·HCl) (1.60 g, 8.35 mmol) were added. The reaction was stirred at room temperature for 1 h before filtering through a 2"x3" pad of silica gel. The pad was washed with DCM (3x25 mL) and the filtrate and washings were combined and concentrated to give 1-{[(morpholin-4-yl) acetyl]oxy}pyrrolidine-2,5-dione (1.3 g, 78%) as white solid. 1H NMR (300 MHz, $CDCl_3$) δ 3.75 (d, J=3.6 Hz, 4H), 3.57 (s, 2H), 2.85 (s, 4H), 2.67 (d, J=4.2 Hz, 4H); MS (ESI) calc.: 242.09, obs.: 243.3 (M+1).

Method 2: Synthesis of 1-{[6-(morpholin-4-yl)pyridine-3-carbonyl]oxy}pyrrolidine-2,5-dione

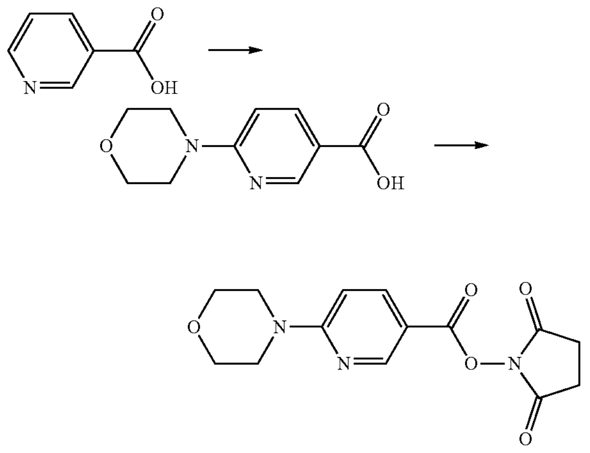

6-(Morpholin-4-yl)pyridine-3-carboxylic acid (350 mg, 1.68 mmol) was dissolved in DCM (25 mL) at room temperature with stirring. NHS (213 mg, 1.85 mmol) was added followed by EDC·HCl (418 mg, 2.18 mmol). The reaction mixture was stirred at room temperature for 1 h and then filtered through a 2"x3" pad of silica gel. The pad was washed with DCM (3x25 mL) and ethyl acetate (25 mL). The filtrate and washings were combined and concentrated to give 1-{[6-(morpholin-4-yl)pyridine-3-carbonyl]oxy}pyrrolidine-2,5-dione (325 mg, 63%) as a white solid. 1H NMR (300 MHz, $CDCl_3$) δ 8.89 (s, 1H), 8.07 (dd, J=9.3 Hz, 1.5 Hz, 1H), 6.60 (d, J=9.3 Hz, 1H), 3.80 (d, J=4.2 Hz, 4H) 3.72 (d, J=4.2 Hz, 4H), 2.89 (s, 4H). MS (ESI) calc.: 305.1, obs.: 306.3 (M+1).

Method 3: Synthesis of tert-butyl 3-{[(2,5-dioxopyrrolidin-1-yl)oxy]carbonyl}thiomorpholine-4-carboxylate

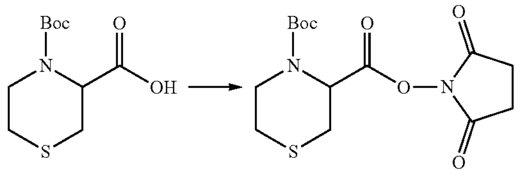 [SMILES: CC(C)(C)OC(=O)N1CCSCC1C(=O)O ; CC(C)(C)OC(=O)N1CCSCC1C(=O)ON1C(=O)CCC1=O]

4-(tert-Butoxycarbonyl)thiomorpholine-3-carboxylic acid (1 g, 4.04 mmol) was dissolved in DCM (25 mL) at room temperature with stirring. NHS (511 mg, 4.44 mmol) was added followed by addition of EDC·HCl (1.01 g, 5.25 mmol). The reaction mixture was stirred at room temperature for 1 h and then filtered through a 2"x3" pad of silica gel. The pad was washed with DCM (3x25 mL) and the filtrate and washings were combined and concentrated to give tert-butyl 3-{[(2,5-dioxopyrrolidin-1-yl)oxy]carbonyl}thiomorpholine-4-carboxylate (1.3 g, 93.4%) as a white solid. 1H NMR (300 MHZ, $CDCl_3$) d 5.38 (br s, 1H), 4.43-4.22 (m, 1H), 3.46-3.21 (m, 1H), 3.19-3.10 (m, 1H), 3.06-2.97 (m, 1H), 2.85 (s, 4H), 2.81-2.62 (m, 1H), 2.61-2.42 (m, 1H), 1.47 (s, 9H). MS (ESI) calc.: 345.4 (M+1).

Method 4: Synthesis of N2-(((9H-fluoren-9-yl)methoxy)carbonyl)-N6-(6-morpholinonicotinoyl)-L-lysine

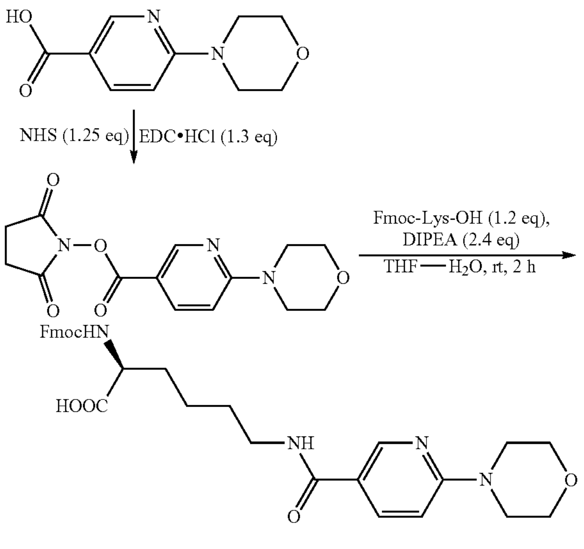

Fluorenylmethyloxycarbonyl chloride L-lysine (Fmoc-Lys-OH) (15.3 g, 41.53 mmol, 1.2 eq) was dissolved in THF-water (1:1, 800 mL) under mechanical stirring at room temperature. A solution of the above prepared ester (Method 2) in DCM was added in one portion followed by DIPEA (10.73 g, 82.99 mmol, 2.4 eq). The reaction was stirred further at room temperature until consumption of the starting material (TLC, 2 h), then ethyl acetate (EtOAc) (250 mL) was added. The mixture was acidified with HCl (1M, 200 mL), poured into a separatory funnel, and the layers separated. The aqueous layer was extracted with EtOAc (2x250 mL). The organic layers were combined, washed with brine (200 mL), dried over anhydrous $Na_2SO_4$, filtered, and concentrated under vacuum. The crude product was obtained as light brown coloured oily residue which was dissolved in THF, adsorbed on silica gel and purified by flash chromatography over a column (7"x3") of silica gel. The column was washed with 50% ethyl acetate in hexanes and 100% ethyl acetate to elute the product under vacuum suction. The fractions containing the required product were combined and concentrated under vacuum to provide N2-(((9H-fluoren-9-yl)methoxy)carbonyl)-N6-(6-morpholinonicotinoyl)-L-lysine (12.6 g, 65%) as off-white coloured solid. 1H NMR (500 MHZ, $CDCl_3$) δ 9.26 (br s, 1H), 8.62 (d, J=1.5 Hz, 1H), 7.93 (dd, J=2.5, 9 Hz, 1H), 7.71 (d, J=7.5 Hz, 2H), 7.53 (dd, J=4.5, 7.5 Hz, 2H), 7.35 (t, J=7.5 Hz, 2H), 7.23 (q, J=6.5 Hz, 2H), 6.59 (t, J=5 Hz, 1H), 6.48 (d, J=9 Hz, 1H), 5.99 (d, J=8 Hz, 1H), 4.41 (dd, J=7.5, 12.5 Hz, 1H), 4.31 (dd, J=12, 18 Hz, 2H), 4.15 (d, J=7 Hz, 1H), 3.71 (t, =4.5 Hz, 4H), 3.56-3.32 (m, 6H), 1.98-1.87 (m, 1H), 1.86-1.75 (m, 1H), 1.71-1.57 (m, 2H), 1.56-1.39 (m, 2H) ppm; 13C NMR (125 MHz, $CDCl_3$) δ 175.2, 166.6, 159.9, 156.6, 146.9, 144.1, 143.9, 141.4, 137.7, 127.9, 127.3, 125.3, 120.1, 119.5, 106.3, 67.2, 66.6, 53.8, 47.3, 45.3, 39.5, 32.0, 28.9, 22.4 ppm; MS (ESI) Exact mass cald. for $C_{31}H_{34}N_4O_6$ [M+H]+: 559.26, found: 559.35.

Method 5: Synthesis of (2S)-2-amino-6-{[6-(morpholin-4-yl)pyridine-3-carbonyl]amino}hexanoic acid (N6-(6-morpholinonicotinoyl)-L-lysine) (LYS (MN))

Procedure 1

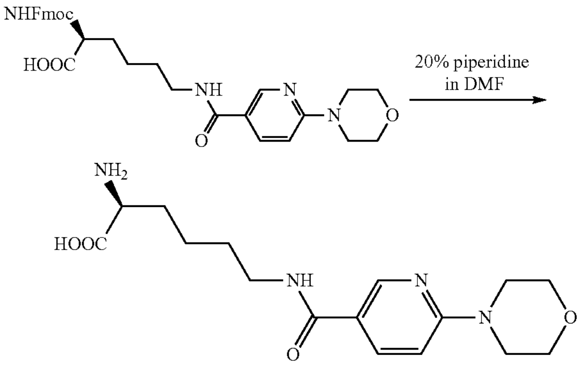

The Fmoc protecting group of N2-(((9H-fluoren-9-yl)methoxy)carbonyl)-N6-(6-morpholinonicotinoyl)-L-lysine (Method 4) may be removed by standard procedures known in the art for example using 20% piperidine in DMF.

Procedure 2

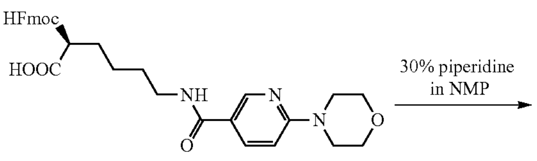

-continued

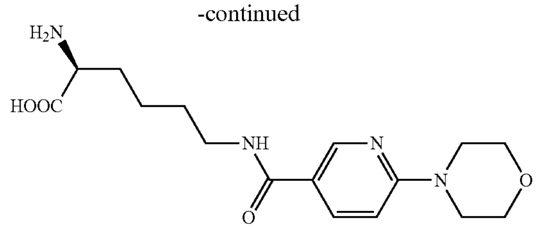

The modified lysine was dissolved in 700 óL of NMP (15 mg, 26.87 ómol. 300 óL piperidine was subsequently added to the solution (Piperidine:NMP=7:3; 1 mL) while stirring. The reaction was stirred at room temperature for 30 minutes. The modified lysine was subsequently precipitated and washed 3 times in cold diethyl ether (10 mL) using centrifugation (4000 g, 10 minutes, 4° C.). 1H NMR (500 MHZ, $CDCl_3$) was used to confirm Fmoc removal 1H NMR (500 MHZ, CDl3) δ 11.89 (s, 1H), 8.85 (dd, 1H), 7.89 (dd, 1H), 7.34 (dd, 1H), 3.52-3.71 (m, 8H), 3.35 (t, 1H), 2.72-2.61 (t, 2H), 2.01-1.57 (m, 6H) ppm. MS (ESI) Exact mass cald. [M+H2O]+: 352.55, found: 352.04.

Method 6: Synthesis of N2-(((9H-fluoren-9-yl)methoxy)carbonyl)-N6-(4-(tert-butoxycarbonyl)thiomorpholine-3-carbonyl)-L-lysine

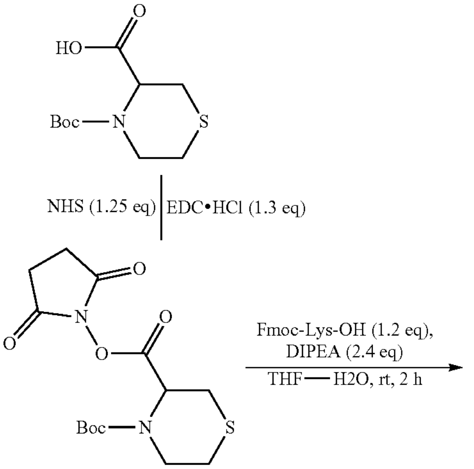

-continued

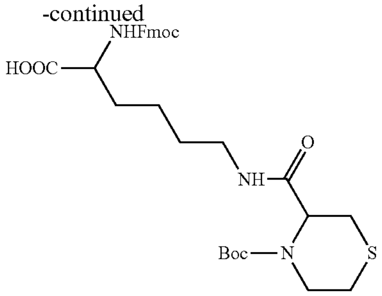

Fmoc-L-Lys-OH (8.94 g, 24.26 mmol, 1.2 eq) was dissolved in THF-water (1:1, 800 mL) under mechanical stirring at room temperature. A solution of the above prepared activated ester (Method 3) in DCM was added in one portion followed by DIPEA (6.27 g, 48.53 mmol, 2.4 eq). The reaction was stirred further at room temperature until consumption of the starting material (TLC, 2 h), then EtOAc (250 mL) was added. The mixture was acidified with HCl (1 M, 200 mL), poured into a separatory funnel, and the layers separated. The aqueous layer was extracted with EtOAc (2×250 mL). The organic layers were combined, washed with brine (200 mL), dried over anhydrous Na2SO4, filtered, and concentrated under vacuum. The crude product was obtained as light yellow coloured oily residue which was dissolved in DCM, adsorbed on silica gel and purified by flash chromatography over a column (7"×3") of silica gel. The column was washed with 50%-70% ethyl acetate in hexanes to elute the product under vacuum suction. The fractions containing the required product were combined and concentrated under vacuum to provide N2-(((9H-fluoren-9-yl)methoxy)carbonyl)-N6-(4-(tert-butoxycarbonyl)thiomorpholine-3-carbonyl)-L-lysine (9.1 g, 75%) as off-white coloured solid. 1H NMR (500 MHz, $CDCl_3$) δ 7.75 (d, J=7.5 Hz, 2H), 7.63-7.51 (m, 2H), 7.38 (t, J=7.5 Hz, 2H), 7.29 (t, J=7.5 Hz, 2H), 5.71 (dd, J=7.5, 23 Hz, 1H), 4.97 (br s, 1H), 4.57-4.23 (m, 4H), 4.20 (t, J=7 Hz, 1H), 3.51-3.18 (m, 3H), 3.17-2.96 (br s, 1H), 2.77 (d, J=12.5 Hz, 1H), 2.70-2.58 (m, 1H), 2.38 (d, J=12.5 Hz, 1H), 1.98-1.86 (m, 1H), 1.85-1.73 (m, 1H), 1.66-1.53 (m, 2H), 1.46 (br s, 12H) ppm; 13C NMR (125 MHz, $CDCl_3$) δ 175.0, 156.4, 155.8, 143.9, 141.4, 127.9, 127.3, 125.3, 120.1, 67.3, 60.6, 53.8, 47.3, 39.2, 31.5, 29.1, 28.5, 26.7, 22.3 ppm; MS (ESI) Exact mass cald. for $C_{31}$H39N307S [M+Na]+: 620.24, found: 620.35.

Method 7: Synthesis (2S)-2-amino-6-[(thiomorpholine-3-carbonyl)amino]hexanoic acid (N6-(thiomorpholine-3-carbonyl)-L-lysine) (LYS™)

Procedure 1

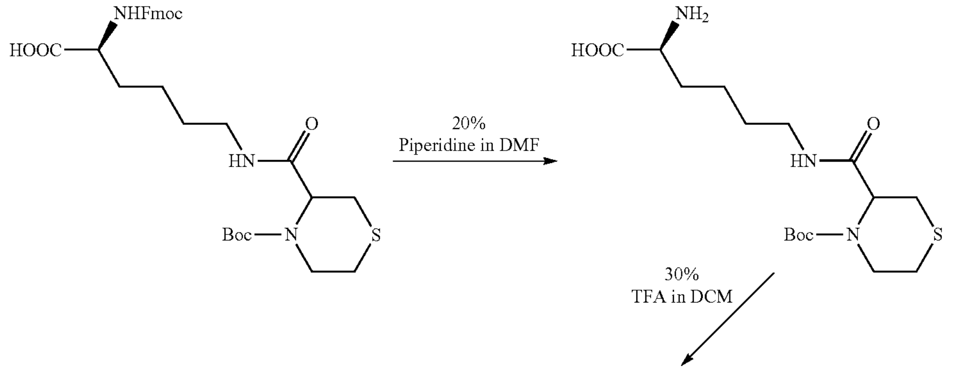

-continued

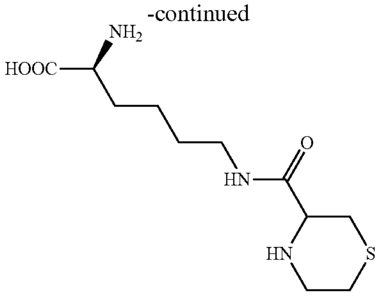

The Fmoc protecting group of N2-(((9H-fluoren-9-yl)methoxy)carbonyl)-N6-(4-(tert-butoxycarbonyl)thiomorpholine-3-carbonyl)-L-lysine (Method 6) may be removed by standard procedures known in the art for example using 20% piperidine in DMF. Similarly, the Boc protecting group may be removed by standard procedures known in the art for example using 30% TFA in DCM.

Procedure 2

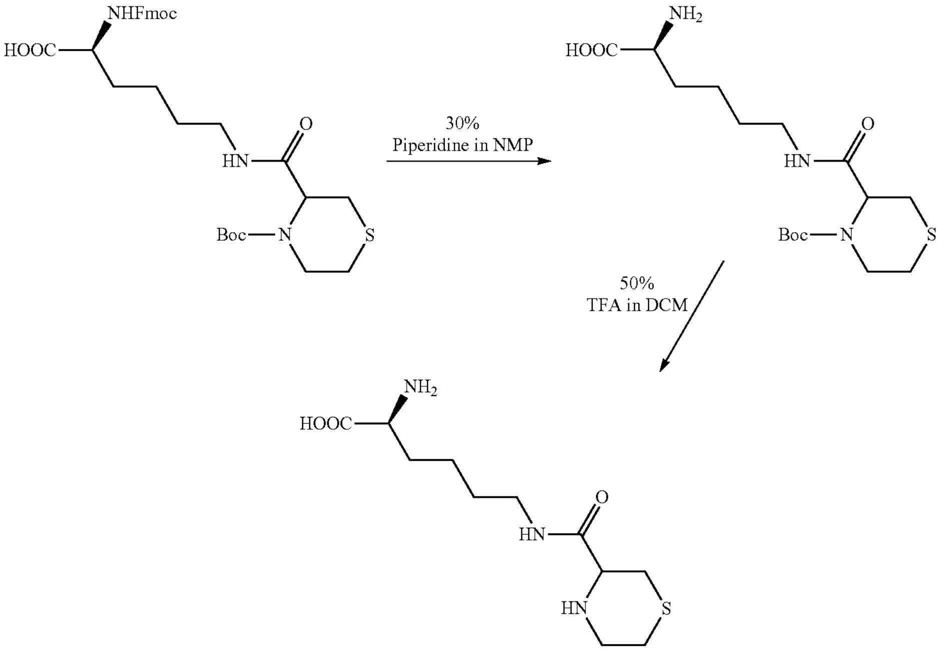

The modified lysine was dissolved in 700 ÓL of NMP (15 mg, 25.12 ómol. 300 óL piperidine was subsequently added to the solution (Piperidine:NMP=7:3; 1 mL) while stirring. The reaction was stirred at room temperature for 30 minutes to remove the Fmoc protectant group. The modified lysine was subsequently precipitated and washed 3 times in cold diethyl ether (10 ml) using centrifugation (4000 g, 10 minutes, 4° C.). After air drying overnight, the product was dissolved in 50% TFA:DCM (1 mL) and stirred at room temperature for 15 minutes. The TFA:DCM solution was removed using a rotary evaporator and the precipitated and washed 2 times in cold ethyl ether Fmoc removal was confirmed using $^1$H NMR: δ 11.56-12.04 (1H, br), 7.34 (s, 1H), 3.65-3.76 (dd, 2H), 3.42 (t, J=7.3 Hz, 1H), 3.01-3.15 (m, 2H), 2.70-2.89 (m, 2H), 2.55-2.61 (t, J=5.6 Hz, 2H), 2.06-2.18 (m, 2H), 1.74-1.85 (m, 2H), 1.58-1.64 (q, 2H) 1.05 (1H, s) ppm and MS (ESI) Exact mass cald. [M+H2O]+: 279.22, found: 279.62.

Method 8: Synthesis of N2 (1-{[(morpholin-4-yl)acetyl]oxy}pyrrolidine-2,5-dione)-L-lysine

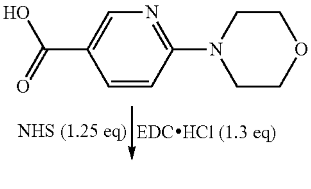

-continued

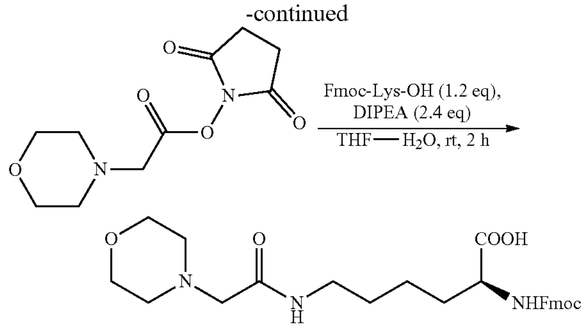

The following procedure could be employed to generate N2 (1-{[(morpholin-4-yl) acetyl]oxy}pyrrolidine-2,5-dione)-L-lysine, Fmoc-L-Lys-OH 1.2 eq) may be dissolved in THF-water (1:1, 800 mL) under mechanical stirring at room temperature. A solution of the above prepared activated ester in DCM may be added in one portion followed by DIPEA (2.4 eq). The reaction may be stirred further at room temperature until consumption of the starting material (TLC, 2 h), then EtOAc (250 mL) may be added. The mixture may be acidified with HCl (1 M, 200 mL), poured into a separatory funnel, and the layers separated. The aqueous layer many be extracted with EtOAc (2×250 mL). The organic layers may be combined, washed with brine (200 mL), dried over anhydrous $Na_2SO_4$, filtered, and concentrated under vacuum. The crude product may be dissolved in DCM, adsorbed on silica gel and purified by flash chromatography over a column (7"×3") of silica gel. The column may be washed with 50%-70% ethyl acetate in hexanes to elute the product under vacuum suction. The fractions containing the required product may be combined and concentrated under vacuum to provide N2-(N2 (1-{[(morpholin-4-yl) acetyl]oxy}pyrrolidine-2,5-dione)-L-lysine.

Method 9: Synthesis of (2S)-2-amino-6-[2-(morpholin-4-yl)acetamido]hexanoic acid (N6-(2-morpholinoacetyl)-L-lysine) (LYS(M))

Procedure 1

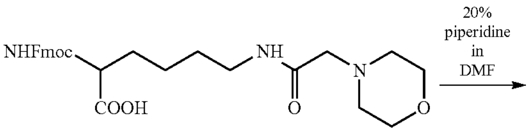

-continued

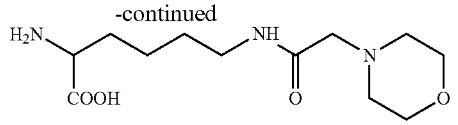

The Fmoc protecting group of N2 (1-{[(morpholin-4-yl) acetyl]oxy}pyrrolidine-2,5-dione)-L-lysine (Method 8) may be removed by standard procedures known in the art for example using 20% piperidine in DMF.

Procedure 2

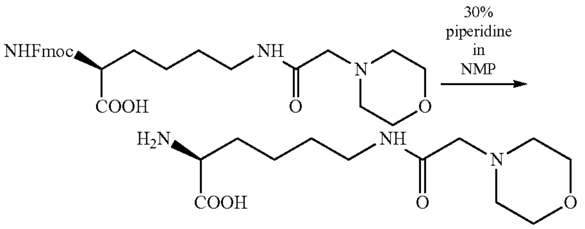

The modified lysine was dissolved in 700 μl of NMP (15 mg, 25.02 μmol. 300 μL piperidine was subsequently added to the solution (Piperidine:NMP=7:3; 1 mL) while stirring. The reaction was stirred at room temperature for 30 minutes. The modified lysine was subsequently precipitated and washed 3 times in cold diethyl ether (10 mL) using centrifugation (4000 g, 10 minutes, 4° C.). Fmoc removal was confirmed using was confirmed using H-NMR: 1H NMR (500 MHZ, CDl3) δ 12.01 (br s, 1H), 3.62-3.74 (m, 4H), 3.40 (t, 1H), 3.29 (s, 2H), 3.10 (t, 1H), 2.59-2.70 (m, 4H), 1.88-2.01 (m, 2H), 1.58-1.65 (m, 2H), and 1.46-1.56 (q, 2H) and MS (ESI) Exact mass cald. [M+H2O]+: 273.17, found: 273.33.

Example 2

Synthesis of Peptide Dendrons with Modified Lysines

A series of peptide dendrons were synthesized (Table 2). The modified lysines were either directly incorporated during peptide synthesis using the modified lysines synthesised in Methods 5, 7 and 9 above (those are marked "*" in the table) or they were subsequently incorporated through modification of lysine side chains (ε-amines) utilising N-hydroxysuccinimide chemistry and the compounds synthesised in of Method 1-3 above in solution post-resin cleavage. PD1-PD3 and PD3(His) were synthesised for comparison and contain unmodified lysines (PD 1-3) or histidine in place of lysine (PD3(His).

TABLE 2

| Peptide Dendron | Sequence | WIPO Standard ST.26 Sequence Fragments in accompanying listing (Sequence ID) (X = non standard amino acid) |
|---|---|---|
| PD1 | ({LEU}{ARG}$_8${***LYS***}{LEU}{ARG}$_4${***LYS***}{LEU}{ARG})$_2${***LYS***}{GLY}{VAL}{CIT}{GLY}{GLY}{SER}{CYS} | LRKLRKLRKGVXGGSC (SEQ ID NO 7)<br>LRKLRKLR (SEQ ID NO 8)<br>LRKLR (SEQ ID NO 9) |
| PD2 | ({ARG}{LEU}{LYS})$_8$({***LYS***}{ARG}{LEU}{LYS})$_4$({***LYS***}{ARG}{LEU}{LYS})$_2${***LYS***}{GLY}{VAL}{CIT}{GLY}{GLY}{SER}{CYS} | RLKKRLKKRLKKGVXGGSC (SEQ ID NO 10)<br>RLKKRLKKRLK (SEQ ID NO 11)<br>RLKKRLK (SEQ ID NO 12) |
| PD3 | ({LYS}{LEU}{ARG})$_8$({***LYS***}{LYS}{LEU}{ARG})$_4$({***LYS***}{LYS}{LEU}{ARG})$_2${***LYS***}{GLY}{VAL}{CIT}{GLY}{GLY}{SER}{CYS} | KLRKKLRKKLRKGVXGGSC (SEQ ID NO 13)<br>KLRKKLRKKLR (SEQ ID NO 14)<br>KLRKKLR (SEQ ID NO 15) |

TABLE 2-continued

| Peptide Dendron | Sequence | WIPO Standard ST.26 Sequence Fragments in accompanying listing (Sequence ID) (X = non standard amino acid) |
|---|---|---|
| PD3(His) | ({HIS}{LEU}{ARG})$_8$({***LYS***}{HIS}{LEU}{ARG})$_4$ ({***LYS***}{HIS}{LEU}{ARG})$_2${***LYS***}{GLY}{VAL} {CIT}{GLY}{GLY}{SER}{CYS} | HLRKHLRKHLRKGVXGGSC (SEQ ID NO 16)<br>HLRKHLRKHLR (SEQ ID NO 17)<br>HLRKHLR (SEQ ID NO 18) |
| PD1(M) | ({LEU}{LYS(M)})$_8$({***LYS***}{LEU}{LYS(M)})$_4$ ({***LYS***}{LEU}{LYS(M)})$_2${***LYS***}{GLY}{VAL}{CIT} {GLY}{GLY}{SER}{CYS} | LXKLXKLXKGVXGGSC (SEQ ID NO 19)<br>LXKLXKLX (SEQ ID NO 20) |
| PD1(MN) | ({LEU}{LYS(MN)})$_8$({***LYS***}{LEU}{LYS(MN)})$_4$ ({***LYS***}{LEU}{LYS(MN)})$_2${***LYS***}{GLY}{VAL} {CIT}{GLY}{GLY}{SER}{CYS} | LXKLXKLXKGVXGGSC (SEQ ID NO 21)<br>LXKLXKLX (SEQ ID NO 22) |
| PD1(TM) | ({LEU}{LYS(TM)})$_8$({***LYS***}{LEU}{LYS(TM)})$_4$ ({***LYS***}{LEU}{LYS(TM)})$_2${***LYS***}{GLY}{VAL}{CIT} {GLY}{GLY}{SER}{CYS} | LXKLXKLXKGVXGGSC (SEQ ID NO 23)<br>LXKLXKLX (SEQ ID NO 24) |
| PD2(M) | ({ARG}{LEU}{LYS(M)})$_8${***LYS***}{ARG}{LEU} {LYS(M)})$_4$({***LYS***}{ARG}{LEU}{LYS(M)})$_2${***LYS***} {GLY}{VAL}{CIT}{GLY}{GLY}{SER}{CYS} | RLXKRLXKRLXKGVXGGSC (SEQ ID NO 25)<br>RLXKRLXKRLX (SEQ ID NO 26)<br>RLXKRLX (SEQ ID NO 27) |
| PD2(MN) | ({ARG}{LEU}{LYS(MN)})$_8$({***LYS***}{ARG}{LEU} {LYS(MN)})$_4$({***LYS***}{ARG}{LEU}{LYS(MN)})$_2$ {***LYS***}{GLY}{VAL}{CIT}{GLY}{GLY}{SER}{CYS} | RLXKRLXKRLXKGVXGGSC (SEQ ID NO 28)<br>RLXKRLXKRLX (SEQ ID NO 29)<br>RLXKRLX (SEQ ID NO 30) |
| PD2(TM) | ({ARG}{LEU}{LYS(TM)})$_8$({***LYS***}{ARG}{LEU} {LYS(TM)})$_4$({***LYS***}{ARG}{LEU}{LYS(TM)})$_2$ {***LYS***}{GLY}{VAL}{CIT}{GLY}{GLY}{SER}{CYS} | RLXKRLXKRLXKGVXGGSC (SEQ ID NO 31)<br>RLXKRLXKRLX (SEQ ID NO 32)<br>RLXKRLX (SEQ ID NO 33) |
| PD3(M) | ({LYS(M)}{LEU}{ARG})$_8$({***LYS***}{LYS(M)}{LEU} {ARG})$_4$({***LYS***}{LYS(M)}{LEU}{ARG})$_2${***LYS***} {GLY}{VAL}{CIT}{GLY}{GLY}{SER}{CYS} | XLRKXLRKXLRKGVXGGSC (SEQ ID NO 34)<br>XLRKXLRKXLR (SEQ ID NO 35)<br>XLRKXLR (SEQ ID NO 36) |
| PD3(MN) | ({LYS(MN)}{LEU}{ARG})$_8$({***LYS***}{LYS(MN)} {LEU}{ARG})$_4$({***LYS***}{LYS(MN)}{LEU}{ARG})$_2$ {***LYS***}{GLY}{VAL}{CIT}{GLY}{GLY}{SER}{CYS} | XLRKXLRKXLRKGVXGGSC (SEQ ID NO 37)<br>XLRKXLRKXLR (SEQ ID NO 38)<br>XLRKXLR (SEQ ID NO 39) |
| PD3(TM) | ({LYS(TM)}{LEU}{ARG})$_8$({***LYS***}{LYS(TM)}{LEU} {ARG})$_4$({***LYS***}{LYS(TM)}{LEU}{ARG})$_2$ {***LYS***}{GLY}{VAL}{CIT}{GLY}{GLY}{SER}{CYS} | XLRKXLRKXLRKGVXGGSC (SEQ ID NO 40)<br>XLRKXLRKXLR (SEQ ID NO 41)<br>XLRKXLR (SEQ ID NO 42) |
| PD3(MN)* | ({LYS(MN)}{LEU}{ARG})$_8$({***LYS***}{LYS(MN)} {LEU}{ARG})$_4$({***LYS***}{LYS(MN)}{LEU}{ARG})$_2$ {***LYS***}{GLY}{VAL}{CIT}{GLY}{GLY}{SER}{CYS} | XLRKXLRKXLRKGVXGGSC (SEQ ID NO 43)<br>XLRKXLRKXLR (SEQ ID NO 44)<br>XLRKXLR (SEQ ID NO 45) |
| PD3(TM)* | ({LYS(TM)}{LEU}{ARG})$_8$({***LYS***}{LYS(TM)}{LEU} {ARG})$_4$({***LYS***}{LYS(TM)}{LEU}{ARG})$_2${***LYS***} {GLY}{VAL}{CIT}{GLY}{GLY}{SER}{CYS} | XLRKXLRKXLRKGVXGGSC (SEQ ID NO 46)<br>XLRKXLRKXLR (SEQ ID NO 47)<br>XLRKXLR (SEQ ID NO 48) |

Summary of peptide dendrons where the bolded, italicized {*LYS*} is a branch point.
*indicates peptides were synthesized directly with modified lysines.

Procedure a) Peptide Dendron Synthesis Via Direct Incorporation of Modified Lysines or Histidine Peptide dendrons were synthesized using standard solid phase peptide synthesis by fragment condensation on a rink amide resin. Each fragment was synthesized on 2-chlorotrityl resin (highly acid labile resin) with Fmoc chemistry and removed from the resin with trifluoroethanol to maintain all protective groups on the side-chains and N-terminal. The peptide dendrons were then built up using the fragments and Nα, Nε-di-Fmoc-L-lysine as branch points and subsequently cleaved from the resin with trifluoroacetic acid (TFA) resulting in C-terminal amidation. The assemble is shown schematically in FIG. 1 illustrated with peptide dendrons with a PD3 base sequence e.g. PD3(M), PD3 (MN), and PD3(TM). All protective groups were removed during the cleavage step. The crude peptide was purified via high pressure liquid chromatography (HPLC) with a water: acetonitrile gradient. Purity and mass were confirmed via HPLC and electron spray ionization (ESI) mass spectrometry. A deconvolution tool was used to interpret the ESI mass spectra which contained the same species in the form of different charge states. Multiply-charged species were calculated into its singly charged form and grouped together according to the m/z value and peak width and presented in atomic mass units (amu). PD1: MW 4540.1 [4540.2 amu]. PD2: MW 7097.1 [7097.5 amu]. PD3: MW 7097.1 [7097.5 amu]. PD3(His): MW 7223.1 [7223.1 amu]. PD3(MN)*: MW 9760.0 [9759.9 amu]. PD3(TM)*: MW 8905.5 [8905.5 amu].

Procedure b) Peptide Dendron Synthesis Via Modification of Peptide Lysine ε-Amines after Cleavage of Dendron Intermediates from Resin 2 μmole of the peptide dendron (PD1, PD2, or PD3) was suspended in freshly prepared 0.1 M sodium bicarbonate pH 8.0. The mixture was sonicated for 10 minutes. 40 mM NHS-functionalized intermediates (Methods 1-3) were prepared in DMAC and added drop-wise to the peptide solution (0.5 mM) while stirring. The NHS-functionalized intermediates were added in 1.5 molar-excess to the lysines per peptide to ensure 100% conversion of the lysine ε-amides.

The reaction was stirred at room temperature for 0.5 hours, and non-reacted intermediate was subsequently removed through ultracentrifugation (MWCO 3.0 kDa). Electrospray ionization mass spectrometry was used to confirm modification. A deconvolution tool was used to interpret the ESI mass spectra which contained the same species in the form of different charge states. Multiply-charged species were calculated into its singly charged form and grouped together according to the m/z value and peak width and presented in atomic mass units (amu). PD2 (M): MW 9904.9 [9904.9 amu]. PD2 (MN): MW 9759.9 [9808.1 amu (MW+formic acid)]. PD2 (TM): MW 8905.5 [8905.5 amu]. PD3(M): MW 9904.8 [9905.0 amu]. PD3(MN): MW 9759.9 [9808.1 amu (MW+formic acid)]. PD3(TM): MW 8905.5 [8905.6 amu].

Example 3

Incorporation of Targeting Moieties or Polyethylene Glycol (PEG) on to the Peptide Dendrons a) Preparation of Methoxy-PEG and Mal-PEG Peptide Dendrons Methoxy-PEG (n=36) functionalized with a maleimide (m-dPEG®$_{36}$-MAL; Quanta BioDesign, Plain City Ohio) and bis-maleimide PEG (n=19) (Bis-Mal-PEG$_{19}$ (BroadPharm, San Diego, CA)) (Compounds #1 and #2 from Table 1) were prepared as a 1.25 and 5 mM solution respectively in 20 mM sodium citrate buffer, pH 5.5. Equivolume peptide dendron solution (prepared as per Example 2, 1 mM) in the same buffer was mixed with the PEG solutions at 1.25- and 5-fold molar excess respectively. The reaction was stirred at room temperature for 2 hours and confirmed via mass spectrometry. Excess PEG was removed via dialysis in PBS and water or in 20 mM sodium citrate pH 5.5 for Mal-PEG-PD conjugates. Electrospray ionization mass spectrometry was used to confirm modification. MeO-PEG (36)-PD2 (MN) MW 11528.2 (11528.2 amu), MeO-PEG (36)-PD3 (TM): MW 10673.9 (10674.1 amu), MeO-PEG (36)-PD2 (MN): MW 11528.2 (11529.2 amu), MeO-PEG (36)-PD3 (TM): MW 10674.2 (10673.9 amu). Mal-PEG (19)-PD1: MW 8296.4 (8297.2 amu), Mal-PEG (19)-PD2 (MN): MW 10959.3 (10960.3 amu), Mal-PEG (19)-PD3(MN): MW 10959.3 (10960.3 amu), and Mal-PEG (19)-PD2 (MN): MW 10959.3 (10960.3 amu).

b) Preparation of Targeted PEG-Peptide Dendron Conjugates

Targeting peptides (Compounds (#3-#6 from Table 1) were prepared using standard solid phase peptide synthesis using Fmoc chemistry. N-terminal acetylation was performed with 10% acetic anhydride in DMF before cleavage from resin. TFP-PEG (n=36)-Maleimide (Quanta BioDesign, Plain City Ohio) (5 mM) and acylated peptides (7.5 mM) were dissolved in freshly prepared 0.1 M sodium bicarbonate buffer pH 8.0 and the peptide solution was added to the PEG solution in 1.25 molar excess. The reaction was stirred at room temperature for 30 minutes before the pH was lowered 5.5 and mass spectrometry was used to confirm the conjugation. The buffer was exchanged using a Vivaspin column MWCO 3.5 kDa (Sigma Aldrich, St. Louis, MO) to 20 mM sodium citrate buffer, pH 5.5. The purified product was subsequently added to peptide dendron (prepared as in Example 2) in 2-fold excess in 20 mM sodium citrate buffer, pH 5.5 at room temperature for 2 h. Electrospray ionization mass spectrometry was used to confirm modification. A deconvolution tool was used to interpret the ESI mass spectra which contained the same species in the form of different charge states. Multiply-charged species were calculated into its singly charged form and grouped together according to the m/z value and peak width and presented in atomic mass units (amu). TfR-PEG-PD3(MN)*: 13855.0 MW (13856.7 amu). cRGD-PEG-PD3 (MN)*: 12188.5 MW (12188.2 amu). TfR-PEG-PD3(TM)*: MW 13855.0 MW (13856.7 amu). cRGD-PEG-PD3(TM)*: 12188.5 MW (12188.6 amu).

c) Preparation of Sugar-PEG-Mal Conjugates

N,N-Diisopropylethylamine (DIPEA) (0.0860 mmol) was added at room temperature to a solution of amine-functionalized mono or tri acetylgalactosamine (GalNAc) (Compounds #7 and 8 from Table 1; Sussex Research, Ontario Canada) (0.01620 mmol) and MAL-dPEG®36-TFP ester (Quanta BioDesign, Plain City Ohio) (0.020261 mmol) in N,N-dimethylformamide (6 mmol). The reaction was stirred at room temperature for 1 h and conjugation was confirmed via HPLC-MS. The product was subsequent purified using reverse phase HPLC. The purified product was subsequently added to peptide dendron (prepared as in Example 2) in 2-fold excess in 20 mM sodium citrate buffer, pH 5.5 at room temperature for 2 h. Electrospray ionization mass spectrometry was used to confirm modification. A deconvolution tool (Agilent Mass Hunter Quantitative Analysis) was used to interpret the ESI mass spectra which contained the same species in the form of different charge states. Multiply-charged species were calculated into its singly charged form and grouped together according to the m/z value and peak width and presented in atomic mass units (amu). GalNAc-PD3(TM)*MW 11708.6 (fragmented: 11506.6) [11506.6 amu]. Tri GalNAc-PD3(TM)*: MW 12679.1 (fragmented: 12071.2) [11507.0 amu].

Example 4

Peptide Dendron/DNA Nanoparticle (NP) Self-Assembly into Monodisperse Nanoparticles The cationic peptide dendrons (PDs) self-assemble with anionic nucleic acids into nanoparticles. NPs were determined to be between spherical and 50-75 nm in diameter using standard nanoparticle techniques that included transmission electron microscopy and dynamic light scattering.

a) NP Preparation

Equivolume DNA (40 μg/ml; Gwiz Luciferase plasmid (6732 bp) (Genlantis, San Diego CA)) and peptide dendron (prepared as in Example 2) solutions were prepared in 20 mM HEPES, pH 7.0. Peptide solutions were made at concentrations corresponding to peptide dendron arginine:DNA phosphate (N:P) of 2:1. DNA solutions were added dropwise to peptide solutions while gently vortexing to ensure homogenous particles. DNA/peptide nanoparticles (NPs) were allowed to complex at room temperature for 30 minutes. The final concentration of DNA in the NP solution was 20 μg/mL.

b) Dynamic Light Scattering

Dynamic light scattering data was collected using a Zetasizer ZS (Malvern), Green Laser and ZEN2112 Quartz cuvette. The hydrodynamic diameter and polydispersity index (PDI) was derived using cumulant fit analysis. All data points represent the mean of three or more individually prepared samples as shown in Table 3.

c) Transmission Electron Microscopy (TEM)

Samples were applied to glow-discharged 400 mesh formva-coated copper grids, negatively stained with 1% uranyl acetate, air-dried and examined in a transmission electron microscope (Tecnai T12, Thermo Fisher Scientific) at an operating voltage of 80 kV. Digital images were acquired using an AMT bottom mount CCD camera and AMT600 software. Morphology was determined as shown in Table 3.

TABLE 3

Characterization of the Peptide Dendrimer DNA Nanoparticles (NPs).

| Formulation | Diameter (nm) | Morphology |
|---|---|---|
| PD1 NP | 61.2 +/− 5.4 | Sphere |
| PD2 NP | 69.2 +/− 7.1 | Sphere |
| PD2(M) NP | 91.0 +/− 4.3 | Sphere |
| PD2(MN) NP | 65.3 +/− 6.9 | Sphere |
| PD2(TM) NP | 78.7 +/− 8.2 | Sphere |
| PD3 NP | 65.8 +/− 8.9 | Sphere |
| PD3(M) NP | 90.1 +/− 6.5 | Sphere |
| PD3(MN) NP | 62.0 +/− 5.4 | Sphere |
| PD3(TM) NP | 61.4 +/− 7.4 | Sphere |
| PD3(His) NP | 75.1 +/− 5.9 | Sphere |

All measurements were derived from the intensity correlation function using cumulant fit analysis. Measurements were collected in triplicate and presented as the mean +/− standard deviation.

Example 5

Peptide Dendron/RNA Nanoparticle (NP) Self-Assembly into Monodisperse Nanoparticles The cationic peptide dendrons (PDs) self-assemble with anionic nucleic acids into nanoparticles. NPs were determined to be about 50 nm in diameter using standard nanoparticle techniques that included dynamic light scattering.

a) NP Preparation

Equivolume RNA (40 μg/mL) and peptide solutions (prepared as in Example 2) were prepared in 20 mM HEPES, pH 7.0. Specifically, cleancap mRNA encoding mcherry (Trilink, San Diego, CA) and siRNA targeting CTNNB1 (Dharmacon/Horizon Discovery, Lafayette, CO) were prepared. Peptide solutions were made at concentrations corresponding to peptide dendron arginine:mRNA phosphate (N:P) ratio of 4:1. RNA solutions were added drop-wise to peptide solutions while gently vortexing to ensure homogenous particles. RNA/peptide nanoparticles or NPs were allowed to complex at room temperature for 30 minutes. The final concentration of RNA in the NP solution was 20 μg/mL. As an optional step Lipofectin® (DOTMA:DOPE (% w/w)=1) (Thermo Fischer Scientific, Waltham, MA) was added to the formulation. Lipofectin® was diluted in 20 mM HPES, pH 7.0 corresponding to a w/w % between 1 and 4 with RNA. The Lipofectin® solution was added to the peptide dendron solution immediately before the addition of the RNA solution as previously described. Nanoparticles containing Lipofectin® are marked "Lipid".

b) Dynamic Light Scattering

Dynamic light scattering data was collected using a Zetasizer ZS (Malvern), Green Laser and ZEN2112 Quartz cuvette. The hydrodynamic diameter and polydispersity index (PDI) was derived using cumulant fit analysis. All data points represent the mean of three or more individually prepared samples. The results are shown in Table 4.

TABLE 4

The hydrodynamic diameter of RNA NPs prepared with PD3(MN) with and without lipid.

| | Hydrodynamic Diameter (nm) | |
|---|---|---|
| Formulation | mRNA | siRNA |
| PD2 NP | 55.8 +/− 6.1 | 50.5 +/− 4.8 |
| PD2(M) NP | 73.1 +/− 5.2 | 59.1 +/− 3.1 |
| PD2(MN) NP | 60.1 +/− 4.8 | 54.7 +/− 5.0 |
| PD2(TM) NP | 53.4 +/− 5.4 | 54.6 +/− 5.2 |
| PD3 NP | 58.3 +/− 2.7 | 57.2 +/− 3.1 |
| PD3(M) NP | 71.2 +/− 3.9 | 66.2 +/− 5.9 |
| PD3(MN) NP | 63.1 +/− 5.2 | 60.2 +/− 4.5 |
| PD3(TM) NP | 52.3 +/− 3.7 | 63.0 +/− 3.9 |
| PEG-PD2 NP | 77.5 +/− 8.9 | 56.9 +/− 9.1 |
| PEG-PD2(M) NP | 85.2 +/− 5.4 | 65.0 +/− 5.8 |
| PEG-PD2(MN) NP | 67.2 +/− 6.9 | 60.1 +/− 3.3 |
| PEG-PD2(TM) NP | 71.2 +/− 5.8 | 65.4 +/− 5.6 |
| PEG-PD3 NP | 80.0 +/− 4.9 | 76.6 +/− 2.8 |
| PEG-PD3(M) NP | 82.8 +/− 6.0 | 73.7 +/− 5.4 |
| PEG-PD3(MN) NP | 61.0 +/− 5.7 | 51.2 +/− 7.9 |
| PD2 NP, Lipid | 50.9 +/− 3.2 | 45.0 +/− 4.5 |
| PD2(M) NP, Lipid | 61.0 +/− 5.6 | 59.2 +/− 2.1 |
| PD2(MN) NP, Lipid | 55.5 +/− 4.5 | 42.5 +/− 3.9 |
| PD2(TM) NP, Lipid | 53.8 +/− 5.9 | 40.6 +/− 4.7 |
| PD3 NP, Lipid | 61.1 +/− 3.0 | 43.9 +/− 8.4 |
| PD3(M) NP, Lipid | 60.1 +/− 3.5 | 56.0 +/− 9.9 |
| PD3(MN) NP, Lipid | 50.1 +/− 5.0 | 41.8 +/− 6.0 |
| PD3(TM) NP, Lipid | 54 +/− 4.5 | 42.3 +/− 6.4 |

All measurements were derived from the intensity correlation function using cumulant fit analysis. Measurements were collected in triplicate and presented as the mean +/− standard deviation.

Example 6

Generation of Targeted NP Nanoparticles a) Preparation of Nanoparticles Comprising a Mixture of Methoxy-PEG Peptide Dendrons and Targeted PEG-Peptide Dendron Conjugates and DNA or RNA Peptide solutions were prepared with different ratios of peptide dendron (prepared as Example 2) or methoxy-PEG dendrons (prepared as Example 3a) and targeted PEG peptide conjugates (prepared as Example 3b) in 20 mM HEPES pH 7.0. DNA (gwiz luciferase) (Genlantis, San Diego, CA) or RNA (clean cap mcherry) (Trilink, San Diego, CA) solutions (40 μg/mL) in the same buffer were added dropwise to the PD mixtures while vortexing so the final ratio of peptide dendron arginine:nucleic acid phosphate (N:P) of 4:1 (DNA) and 6:1 (RNA). Nucleic acid/peptide nanoparticles were allowed to complex at room temperature for 30 minutes. The final concentration of nucleic acid in the nanoparticle solution was 20 g/mL. As an optional step, Lipofectin® (DOTMA:DOPE (% w/w)=1) (Thermo Fischer Scientific, Waltham, MA) was added to the formulation. Lipofectin® was diluted in 20 mM HPES, pH 7.0 corresponding to a w/w % between 1 and 4 with RNA. The Lipofectin® solution was added to the peptide dendron solution immediately before the addition of the RNA solution as previously described.

b) Preparation of Nanoparticles Comprising a Mixture of Methoxy-PEG Peptide Dendrons and Targeted PEG-Antibody Conjugates and DNA or RNA For antibody-based targeting ligands, mal-PEG PD nanoparticles were prepared and then conjugated to antibodies (Compounds #5 and #6 of Table 1 modified as per the below). Peptide solutions were prepared with different ratios of methoxy-PEG dendrons (Example 3a) and mal-PEG dendrons (Example 3a) in 20 mM HEPES pH 7.0. DNA (gwiz luciferase) (Genlantis, San Diego, CA) or RNA (clean cap mcherry) (Trilink, San Diego, CA) solutions (40 µg/mL) in the same buffer were added dropwise to the PD mixtures while vortexing to give a ratio of peptide dendron arginine: nucleic acid phosphate (N:P) of 4:1 (DNA) and 6:1 (RNA). Nucleic acid/peptide nanoparticles were allowed to complex at room temperature for 30 minutes. The final concentration of nucleic acid in the nanoparticle solution was 20 µg/mL.

c) Dynamic Light Scattering

Dynamic light scattering data was collected using a Zetasizer ZS (Malvern), Green Laser and ZEN2112 Quartz cuvette. The hydrodynamic diameter and polydispersity index (PDI) was derived using cumulant fit analysis. All data points represent the mean of three or more individually prepared samples.

TABLE 5

Dynamic Light Scattering of Targeted DNA NPs.

| Targeted PEG-peptide | Molar % ratio targeted MeO-PEG-peptide dendron conjugates:MeO-PEG-PD3(MN) | | | | |
|---|---|---|---|---|---|
| dendron conjugate | 0 | 12.5 | 25 | 50 | 100 |
| PD3(MN)-Tfr | 75.1 +/− 5.0 | 83.2 +/− 5.6 | 83.0 +/− 7.3 | 85.8 +/− 9.1 | 85.4 +/− 9.0 |
| PD3(MN)-cRGD | 78.3 +/− 4.3 | 81.2 +/− 7.3 | 78.2 +/− 5.1 | 81.8 +/− 6.0 | 84.9 +/− 7.9 |
| PD3(MN)-Anti-CD3 | 79.1 +/− 6.7 | 85.3 +/− 9.8 | 101.9 +/− 8.9 | 105.2 +/− 4.2 | 105.6 +/− 3.3 |
| PD3(MN)-MECA32 | 79.1 +/− 6.7 | 91.0 +/− 8.7 | 102.1 +/− 7.6 | 105.8 +/− 7.1 | 110.1 +/− 5.9 |

All measurements were derived from the intensity correlation function using cumulant fit analysis. Measurements were collected in triplicate and presented as the mean +/− standard deviation.

TABLE 6

Dynamic Light Scattering Diameter of Targeted siRNA NPs.

| | Molar % ratio cRGD—PEG—PD3(MN): MeO—PEG—PD3(MN) | | | | |
|---|---|---|---|---|---|
| Non Targeted NP | 0 | 12.5 | 33.3 | 66.6 | 100 |
| PD3(MN) | 57.2 nm | 56.9 nm | 60.2 nm | 63.1 nm | 66.8 nm |
| PD3(MN), Lipid | 50.5 nm | 59.3 nm | 55.4 nm | 61.2 nm | 60.4 nm |
| PEG-PD3(MN) | 59.1 nm | 61.2 nm | 60.3 nm | 65.3 nm | 66.9 nm |
| PEG-PD3(MN), Lipid | 54.7 nm | 56.2 nm | 60.1 nm | 61.9 nm | 64.9 nm |

All data was collected in triplicate and presented as the mean with standard deviation. intensity correlation function using cumulant fit analysis Fabs and/or halfmers (one light chain and one heavy chain) were engineered with a non-natural amino acid substitution within the heavy chain:

(Nnaa CP1)

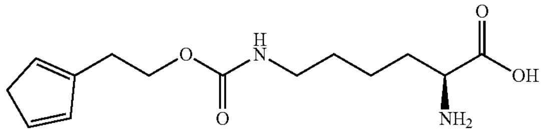

The non-natural amino acid contains a cyclopentadiene (Nnaa CP1) within its side chain that can serve as a reactive handle for a Diels-Alder reaction. Nnaa CP1 was genetically encoded into the antibody sequence using Chinese hamster ovary (CHO) cells expressing the *Methanosarcina mazei* pyrrolysine tRNA synthetase/tRNA (PyIRS)/tRNA (Pyl) pair that delivers the Nnaa CP1 in response to an amber stop (TAG) codon. (Amant et al. Angew Chem, 2019, 58 (25): 8489-93).

The engineered antibody-based targeting moieties were added to the nucleic acid/peptide nanoparticle solution in 1.25 molar excess to the maleimide at room temperature for 2 h. as described in Example 6. The mixture was subsequently quenched through the addition of N-acetyl cysteine (10-fold molar excess). Excess antibody was removed using ultracentrifugation (MWCO 100 kDa) and the reaction was confirmed using A260/A280 ratios and dynamic light scattering.

Example 7

Figure 2A:
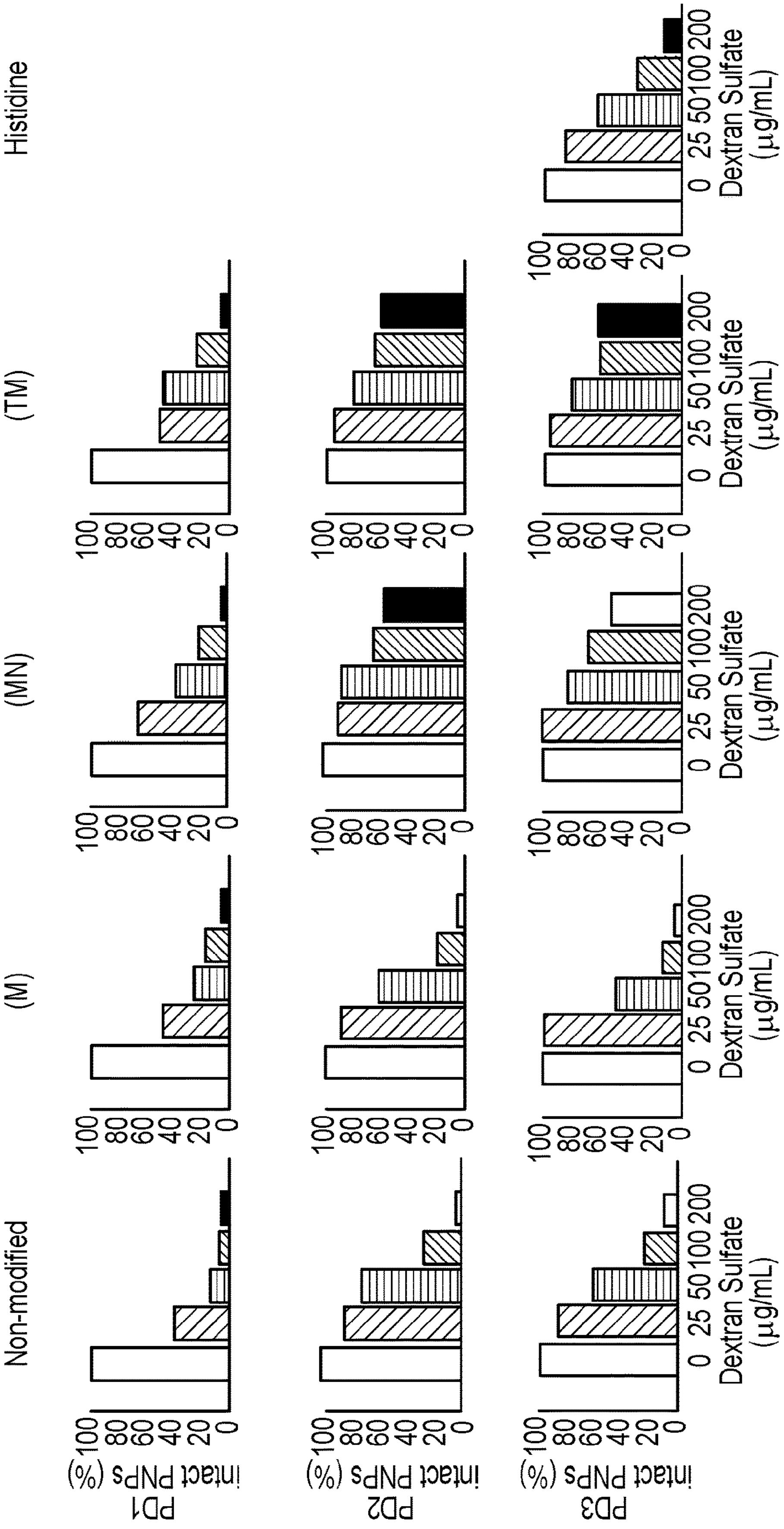
FIG. 2A and FIG. 2B: The results of the peptide nanoparticle (PNP) stability against anionic dissociation (A) and cathepsin B degradability (B) as described in Example 7. Nanoparticle stability is vital for efficient delivery of intact nucleic acid into target cells; however, the nucleic acid must be released upon cellular uptake to perform its function. To this end, the PDs have been designed to enzymatically degrade upon cellular uptake. Materials with stimuli-responsive release were determined to have enhanced efficacy and lower toxicity. The results show the PD3(MN) and PD3 (TM) nanoparticles were significantly more resistant to anionic dissociation compared to nanoparticles formulated with PD1, non-modified (NM) PDs, and PD3(His) which readily released DNA at dextran sulphate concentrations exceeding 50 μg/mL. Moreover, PD3(M), PD3(MN), and PD3(TM) readily released DNA in response to cathepsin-B activity relative to non-modified PD3 and all PD2 formulations.

NPs Generated Stable Nanoparticles with Stimuli-Response DNA Release a) Anionic Stability Assay Dextran sulfate (DS) solutions were prepared in 20 mM HEPES and added to NP solutions (prepared as in Example 4) so the final DS concentration was between 100 mg/ml to 1000 mg/ml and DNA concentration was 10 µg/mL. After a 15-minute decomplexation period, 15 µl of each formulation was added to a 2% E-gel with ethidium bromide and run for 10 minutes. pDNA release was calculated using ImageJ (NIH, Bethesda, Maryland) and the results shown in FIG. 2A where the percent of intact nanoparticles Is plotted as a function of DS concentration.

b) Enzymatic DNA Release

Figure 2B:
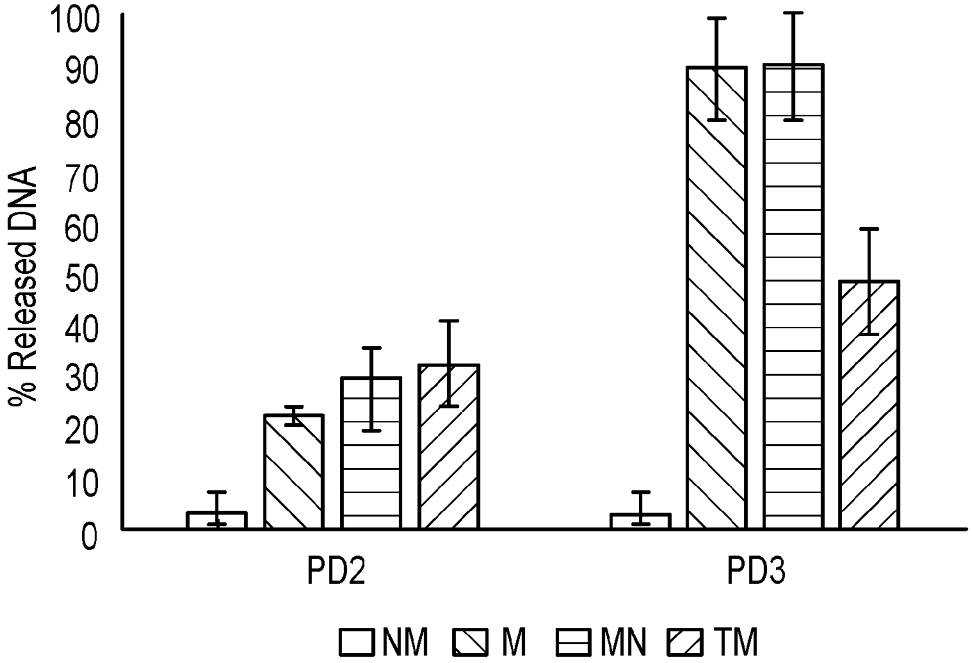

NPs prepared as in Example 4 but in 8 mM L-Cysteine HCl buffer pH 6 at a final DNA concentration of 0.1 µg/µl. Cathepsin-B stock solution (60 units/mL) was subsequently added. Cat-B NP solutions were incubated at 37° C. for up to 4 hours. Aliquots were removed at the appropriate time points and analysed via agarose gel electrophoresis to visualize released DNA. DNA dilutions were prepared at different concentrations as a control and likewise added to the same agarose gel for subsequent quantification using bio-rad intensity software analysis and the results shown in FIG. 2B.

TABLE 7

| Programmed Enzymatic Release of pDNA. | | | | | |
|---|---|---|---|---|---|
| | DNA Release (%) | | | | |
| Modification | Not Modified | M | MN | TM | Histidine |
| PD1 | 0 | 0 | 0 | 0 | — |
| PD2 | 0 | 26 | 0 | 22 | — |
| PD3 | 0 | 83 | 98 | 11 | 5.2 |

The table summarizes the % pDNA release after 1 h of cathepsin-B treatment with different NP formulations.

Example 8

Figure 3A:
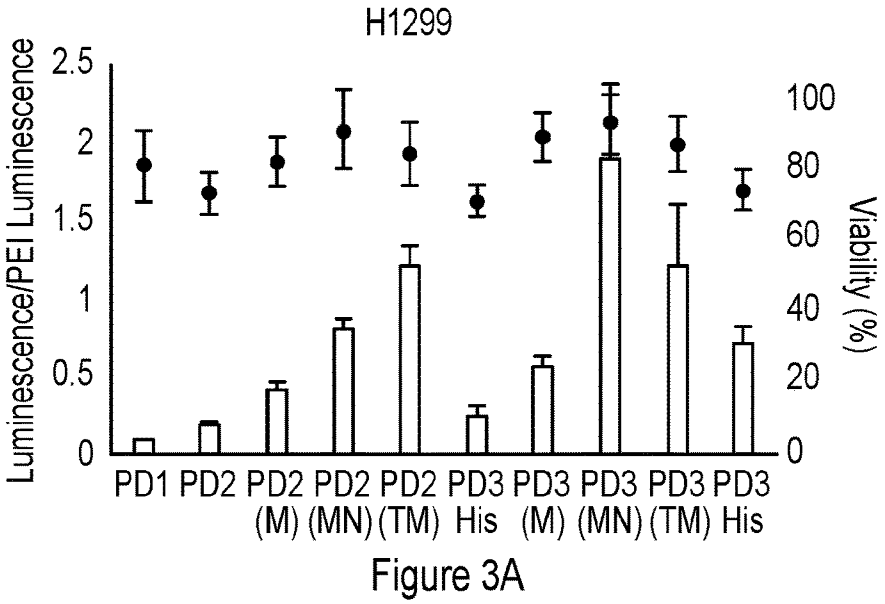
FIG. 3A, FIG. 3B, and FIG. 3C: The results obtained from the in vitro transfection screening as described in Example 8. Different cell lines were assessed as shown in FIG. 3A) human non-small lung cancer cell lines H1299 and FIG. 3B) mouse myotubes cell line C2C12. Luminescence was collected in quadruplicate and presented as the mean +/−standard deviation.
Figure 3B:
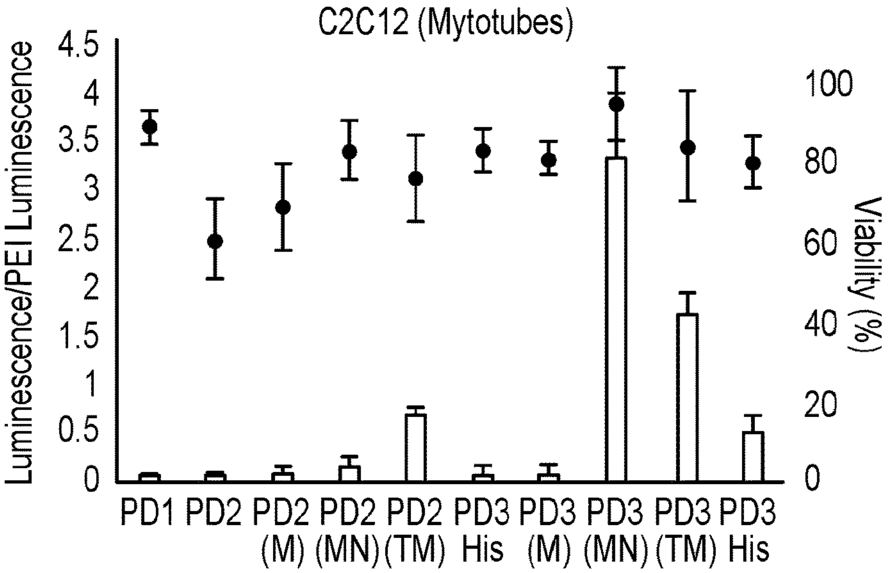
Figure 3C:
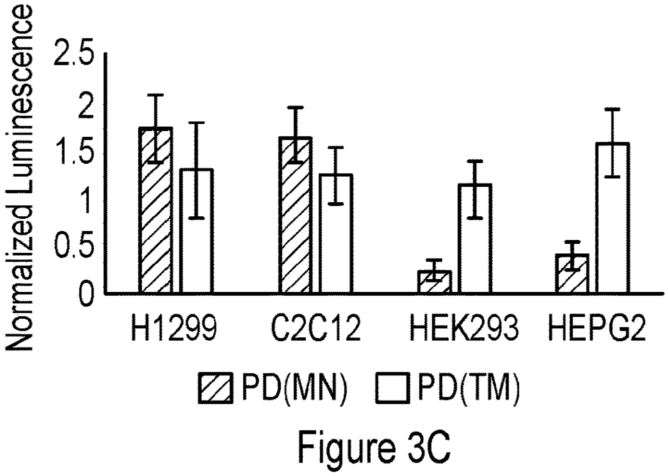

NPs Demonstrate Cell Specificity in In Vitro Transfections a) In Vitro Transfections H1299, $C_2C12$, HEK393, and HEPG2 cell lines were seeded in 96-well plates targeting an 80% confluency within 24 hours. C2C12 were subsequently incubated for 7-days in Dulbecco's Modified Eagle Medium (DMEM) supplemented with 2% horse serum to differentiate from myoblasts to myotubes. After a 24-hour recovery period, NPs (prepared as in Example 2) were added to the cells at 0.2 μg per well in OPTI-MEM (1:10 dilution). After a 16-hour period, the NP supplemented media was removed and fresh culture media was added. GFP was imaged using the Incucyte (EssenBio) and luciferase/viability quantified using the standard protocol for the ONE-Glo™+Tox Luciferase Reporter (Promega). The results are shown in FIGS. 3A, 3B, and 3C.

Example 9

Intramuscular DNA NPs In Vivo Transfections a) Intramuscular Delivery

Figure 4:
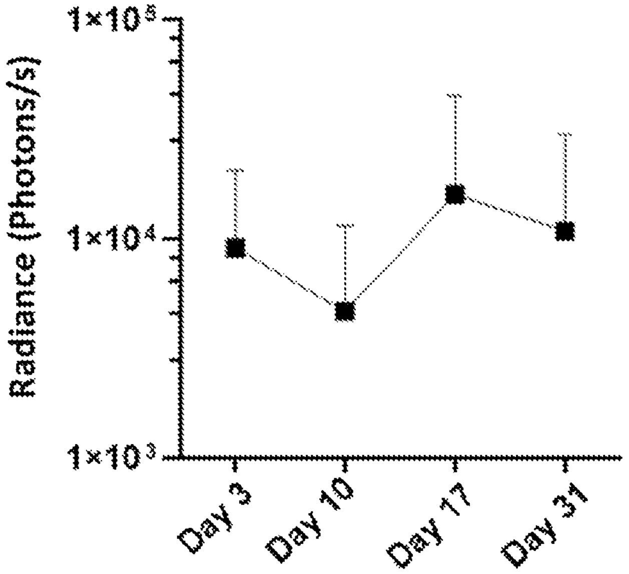
FIG. 4: The results obtained from the luciferase mRNA mouse expression experiment described in Example 9. DNA NPs translation in vivo translation was tested in mouse intramuscular expression studies. Reporter protein luciferase was expressed to allow for live-tracking of expression. Expression was observed and determined to be consistent for the monitoring period of 1-month. Expression was assessed weekly using IVIS and luminescence was collected in quadruplicate and presented as the mean+/−standard deviation. The results show MeO-PEG-PD (MN) efficiently delivers DNA via IM injection in vivo resulting is stable expression for a month.

BALB/C mice were treated with 5 μg of pDNA (Gwiz Luciferase) (Genlantis, San Diego, CA) complexed with MeO-PEG-PD (MN) (prepared as in Example 5) per limb. Expression was assessed weekly using IVIS (Perkin Elmer). Luminescence was collected in quadruplicate and presented as the mean+/−standard deviation. The results are shown in FIG. 4.

Example 10

DNA NPs Therapeutic Expression a) Preparation of MEDI8852 and STK11 Encoded PD Nanoparticles Nanoparticles were prepared as described in Example 4 with PD3(MN) and plasmids that encode therapeutics MEDI8852 and STK11. For MED8852 expression, NPs were also prepared with TfR-PEG-PD3 (MN) and MeO-PD3(MN) (peptide dendron arginine:nucleic acid phosphate N:P 4:1) where 25% of the peptide was TfR-PEG-PD3 (MN). Equivolume DNA (40 μg/mL; MEDI8852 plasmid (prepared in a similar manner to Minimal CMV Expression plasmid from Sigma-Aldrich, St. Louis, MO) or STK11 (Origene, Rockville MD) Plasmid) and peptide dendron solutions were prepared in 20 mM HEPES, pH 7.0. Peptide dendron solutions were made at concentrations corresponding to peptide dendron arginine:nucleic acid phosphate (N:P) of 4:1. DNA solutions were added drop-wise to peptide solutions while gently vortexing to ensure homogenous particles. DNA/peptide nanoparticles were allowed to complex at room temperature for 30 minutes. The final concentration of DNA in the NP solution was 20 μg/mL. As a control, MEDI8852 plasmid was also prepared with lipofectamine-2000 (ThermoFisher, Waltham, MA) using the manufacture's protocol.

b) In Vitro Transfection Studies with Therapeutic Encoded Nanoparticles

Figure 5A:
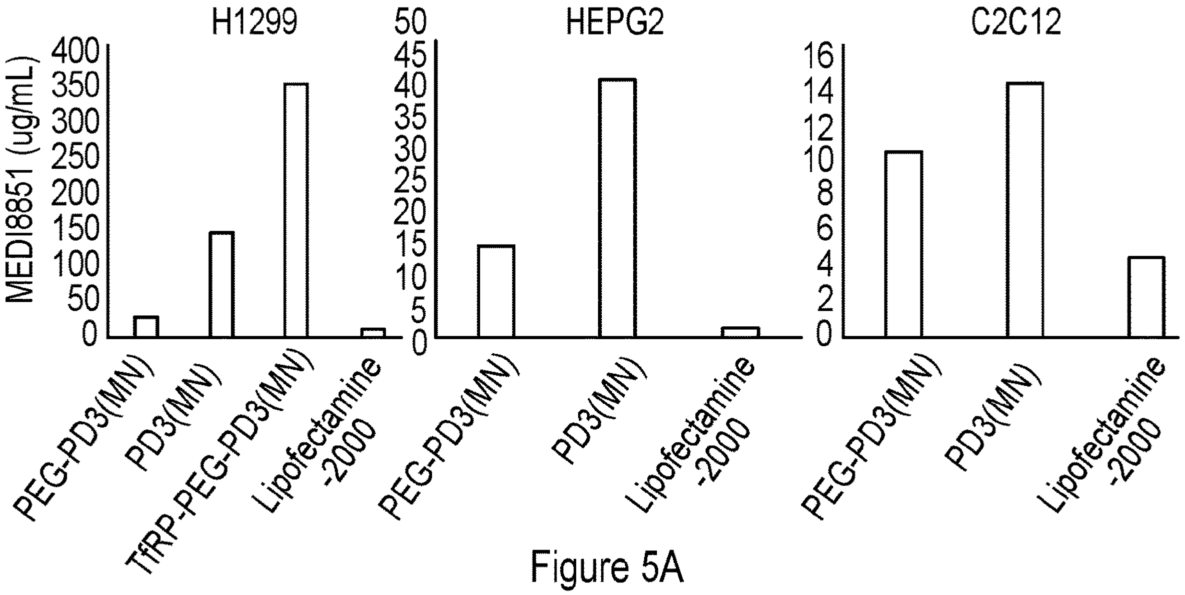
FIG. 5A and FIG. 5B. The results obtained from the therapeutic expression experiment described in Example 10.
Figure 5B:
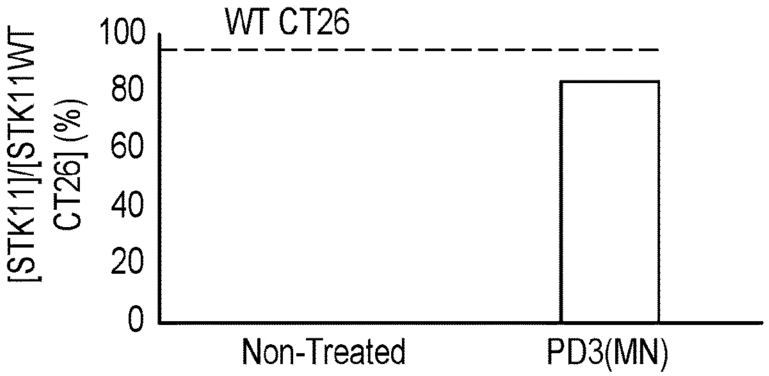

H1299 (6,600 cells/well), HEPG2 (50,000 cell/well) and C2C12 (12,000 cells/well cells) were seeded in 96-well plates in RPMI media or in DMEM supplemented with 10% fetal bovine serum (FBS) and 1% penicillin-streptomycin (P/S) respectively. After a 24 h-recovery period, cells were washed twice with 100 μL of PBS and once with culture media. Nanoparticles were then added to the cells at 0.2 μg (H1299) or 0.5 μg (HEPG2 and C2C12) per well in culture media. After a 16-hour period, the nanoparticle supplemented media was removed, and fresh culture media was added. MEDI8852 expression was quantified using an ELISA as described below (c) and STK11 expression was detected with a Western Blot as described below (d). The results are shown in FIGS. 5A and 5B respectively.

c) Medi8852 ELISA

NUNC™ MaxiSorp™ 96-well microplates were coated with 100 μL/well of anti-MEDI8852 antibody (Ali, S et al. Antimicrob Agents Chemother. 2018 November; 62 (11): e00694-18.) at 1 μg/mL in bicarbonate buffer. Plates were incubated overnight at 4° C., then washed three times with 300 μL PBS-T (phosphate buffered saline (PBS)+0.1% Tween 20) the following morning. All standards, quality control samples, and test samples were diluted 1:250 in 0.5% bovine serum albumin (BSA) in PBS+0.1% Tween 20. 100 μL of diluted sample was loaded into each well and incubated for 2 hours. Following incubation, plates were washed three times with 300 μL PBS-T. The secondary antibody, biotinylated anti-MEDI8852 (Ali, S et al. Antimicrob Agents Chemother. 2018 November; 62 (11): e00694-18.) was diluted to 2 μg/mL in PBS-T and 100 μl was added to each well and incubated at 37° C. for 1 hour. The plate was then washed four times with PBS-T and 100 μL of the streptavidin-HRP complex (Jackson Immuno Research Laboratories, Inc., code 016-030-084) at a dilution of 1:40 was added. The plate was washed four times with PBS-T and 100 μL room temperature-equilibrated SureBlue TMB Substrate (Thermo Fischer Scientific) was added to all wells. After 15 minutes in the dark, 100 μL of TMB Stop Solution (Thermo Fischer Scientific) was used to quench the reaction. Optical densities (ODs) of each well were read at 450 nm using BMG Labtech PHERAstar FSX microplate reader. The results are shown in FIG. 5A.

e) STK11 Western Blot

Cells were lysed using RIPA lysis buffer (Teknova cat. No. R3792) supplemented with Protease and Phosphatase Inhibitor (Pierce #78442) post transfection and spun down at 12,000×g for 5 mins. The supernatant was collected and quantified using a BCA assay (Thermo prod #23227). 10 μg of extracted protein per sample was then resolved using SDS-polyacrylamide electrophoresis with a 200 mA current for 90 mins, then transferred to PVDF membranes via the iBlot system. Membranes were subsequently blocked with TBS-T (20 mM Tris-HCl, pH 7.6) supplemented with 5% BSA. Rabbit anti-STK11 (Cell Signaling cat. no D60C5) and anti-GAPDH (Cell Signalling cat. no 14C10) primary antibodies were hybridized overnight at a 1:10,000 dilution. The membranes were washed for 30 mins then hybridized to HRP-conjugated goat anti-rabbit IgG for 30 mins. Following incubation, membranes were washed to eliminate any unspecific binding and incubated with the Pierce SuperSignal West Pico chemiluminescent reagents (Pierce cat. no.

34579). Bands were detected using the Image Quant LAS 4000. The results are shown in FIG. 5B.

Example 11

Targeted DNA NP Transfections In Vitro a) In Vitro Transfections

Figure 6A:
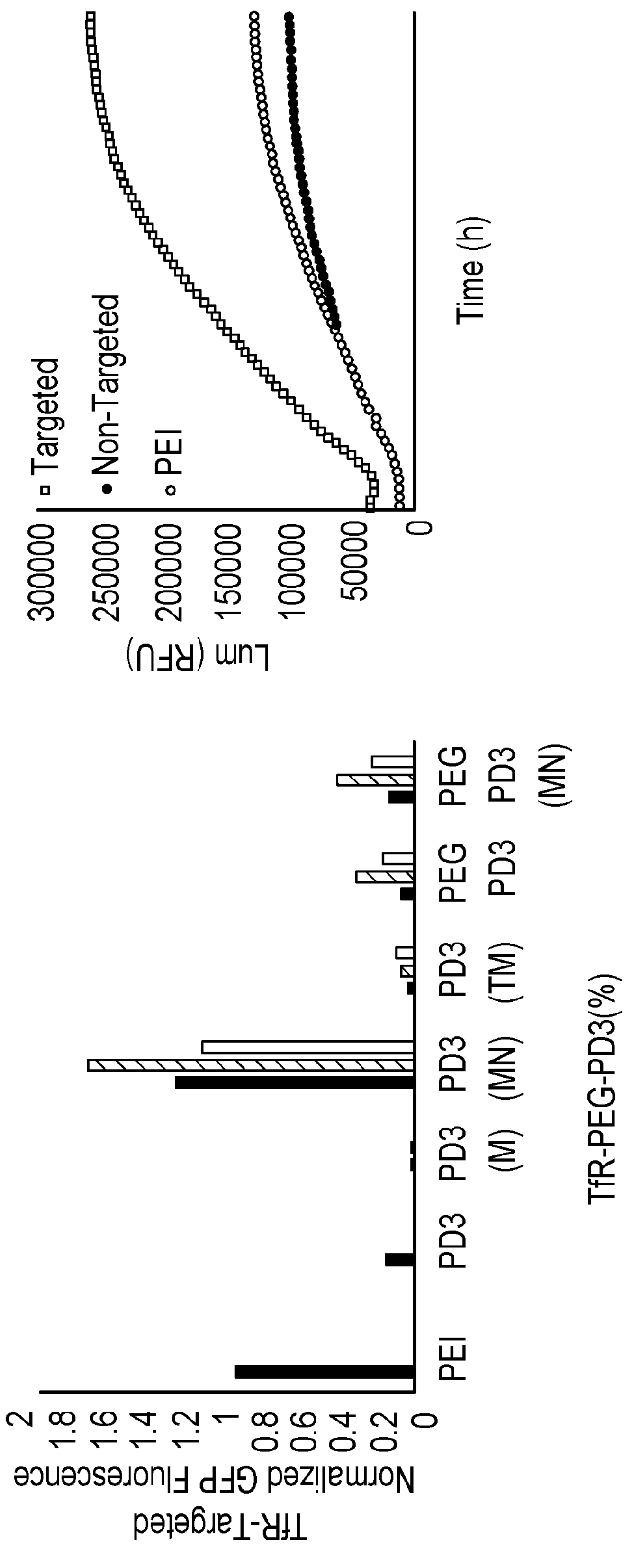
FIG. 6A, FIG. 6B and FIG. 6C. The results obtained from targeted DNA NP transfections in vitro as described in Example 11. Targeted PD Nanoparticles were tested in various cell lines and determined to boost transfection. In H1299, TfR (FIG. 6A) and cRGD (FIG. 6B) enhanced overall expression levels (delivering GFP, fluorescence) and kinetics (delivering Gwiz Luciferase; luminescence) relative to commercial transfection control polyethyleneimine (PEI). Similar improvements in transfection were observed in C2C12 and CT26 relative to non-targeted NPs (FIG. 6C). Targeted DNA delivery can be used to increase transfection efficiency and/or achieve cell-specific expression. The PD platform was purposefully designed with a flexible targeting strategy which has allowed for the incorporation of a range of targeting ligands both peptide and antibody-based (as shown in Example 3 and 5) that has significantly boosted transfection. Moreover, through PEGylation and targeting highly specific expression has been achieved. These results shows targeting can be used to enhance expression in multiple, very different cell lines.
Figures 6B, 6C:
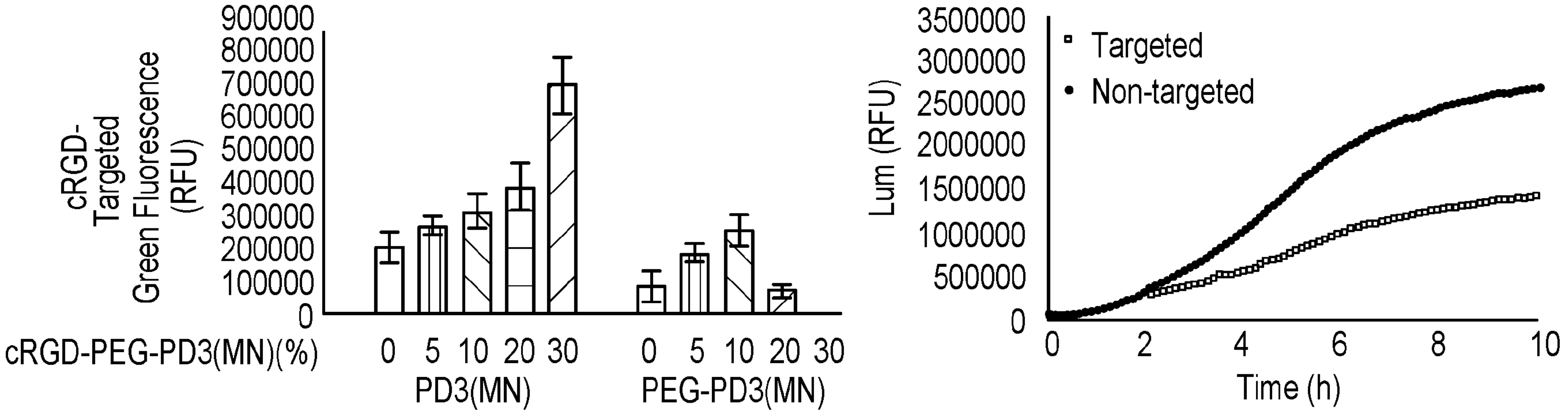

H1299 (6,600 cells/well), CT26 (10,000 cell/well) and C2C12 (12,000 cells/well cells) were seeded in 96-well plates in RPMI media or in DMEM supplemented with 10% fetal bovine serum (FBS) and 1% penicillin-streptomycin (P/S) respectively. Before transfection H1299 and CT26 cells were allowed a recovery period of 24 h while C2C12 myoblasts were differentiated into myotubes through incubation DMEM supplemented with 2% horse serum for a minimum of 7 days. Subsequently, cells were washed twice with 100 μL of PBS and once with culture media. Targeted and non-targeted nanoparticles were prepared with Gwiz Luciferase plasmid (Genlantis, San Diego CA) as described in Example 6. TfR- and cRGD targeted NPs were prepared with a mixture of MeO-PEG-PD (MN):TfR-PEG-PD (MN) or cRGD-PEG-PD (MN) (materials prepared in Example 3 a) and b)) where with 0, 10, and 50% TfR-PEG-PD (MN) and 0, 5, 10, 20, and 30% cRGD-PEG-PD (MN) was employed. NPs were added to the cells at 0.2 μg per well in culture media (1:10 dilution). After a 16-hour period, the nanoparticle supplemented media was removed, and fresh culture media was added. GFP expression was imaged using the Incucyte (Essen BioScience, Ann Arbor, MI) and luciferase/viability quantified using the standard protocol for the ONE-Glo™+Tox Luciferase Reporter (Promega, Madison, WI) and PHERAstarFSX instrument (BMG Lab Tech, Cary, NC). The results are shown in FIGS. 6A-C.

Example 12 a) Nanoparticle Preparation

PV1-targeted MECA32 was engineered and expressed as a halfmer (one light chain and one heavy chain) with a non-natural amino acid substitution within the heavy chain as described in Example 6. NPs were prepared with PD3 (MN) PEG conjugates (prepared as in Example 6) and Gwiz Luciferase plasmid (Genlantis, San Diego CA) in 5% trehalose buffer with a peptide dendron arginine:nucleic acid phosphate (N:P) ratio of 4:1 (75% MeO-PEG-PD3(MN): 25% Mal-PEG-PD3(MN)) using the protocol described in Example 6. CP1-MECA32 (Gabriela M. Marchetti, et al. Commun Biol. 2019; 2:92; Published online 2019 Mar. 7. doi: 10.1038/s42003-019-0337-2) was added in 1.25-fold molar excess based on the moles of maleimide and incubated overnight at room temperature. The reaction was quenched through the addition of N-acetyl cysteine (10-fold molar excess) and excess antibody was removed using ultracentrifugation (MWCO 100 kDa).

b) Lung Targeted Delivery in Mice

Figure 7:
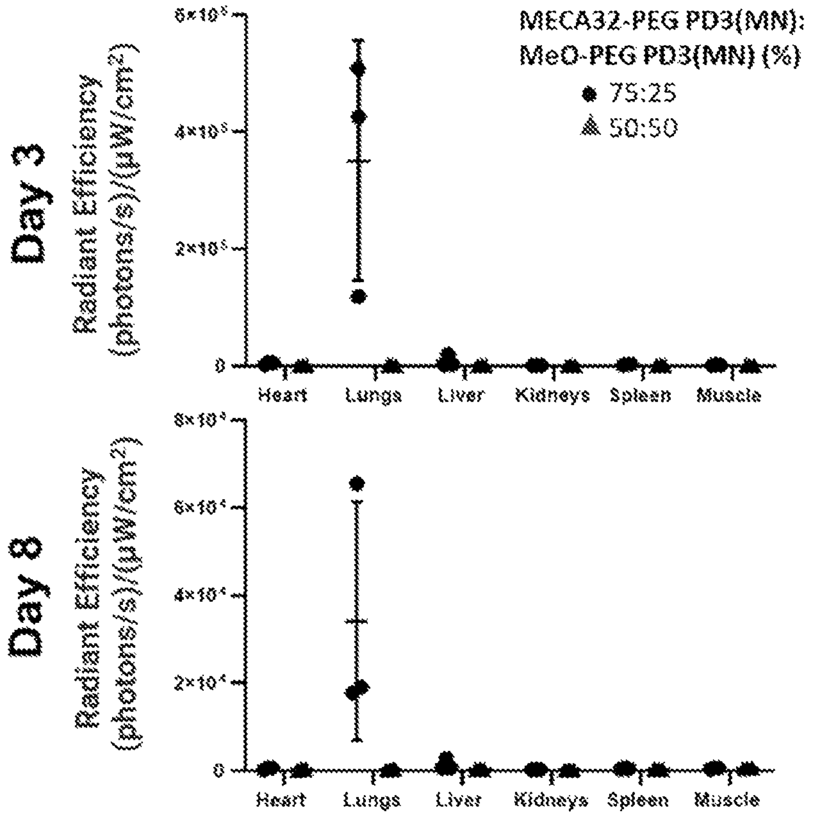
FIG. 7: The results obtained from the lung-targeted NPs in vivo experiment as described in Example 12. PV1 targeted nanoparticles were administered IV in to BALB/C mice and expression of luciferase was monitored via IVIS for 8 days. Ex vivo imaging on day 3 and day 8 demonstrated nanoparticles with the optimized ligand density only had significant expression within the targeted lungs. Cell-specific delivery greatly broadens the potential applications of nucleic acid-based therapies. These results show antibody based targeting moieties can be used to generate targeted PD NPs, and PV1 targeting can be used to target the lungs. In this example, PV1-targeted NPs were demonstrated to achieve highly specific expression within a mouse lung for a minimum of 8-days.

BALB/C mice were treated intravenously with 20 μg of Gwiz luciferase pDNA complexed with PD (MN). 10% of the pDNA was labelled with Cy-5 (12 labels/plasmid). Expression and biodistribution was assessed on day 1, 3 and 8 using IVIS (Perkin Elmer). Each treatment was conducted in quadruplicate and quantitively data is presented as the mean+/−standard deviation. The results are shown in FIG. 7.

Example 13 mRNA NP Transfection In Vitro a) DNA & mRNA NP Preparation

A peptide dendron solution was prepared PD3(MN) (prepared as in Example 4 and 5) in 20 mM HEPES pH 7.0. DNA (Origene, Rockville MD) or mRNA (Trilink, San Diego, CA) encoding mCherry were diluted in in the same buffer (40 μg/mL) and added dropwise to the PD mixtures while vortexing so the final ratio of peptide dendron arginine:nucleic acid phosphate (N:P) was 2:1 (DNA) or 4:1 (mRNA). Nucleic acid/peptide nanoparticles were allowed to complex at room temperature for 15 minutes. The final concentration of nucleic acid in the nanoparticle solution was 20 μg/mL. NP were characterized using DLS as described in Example 4 (DNA) and 5 (mRNA).

b) In Vitro Transfections

Figure 8:
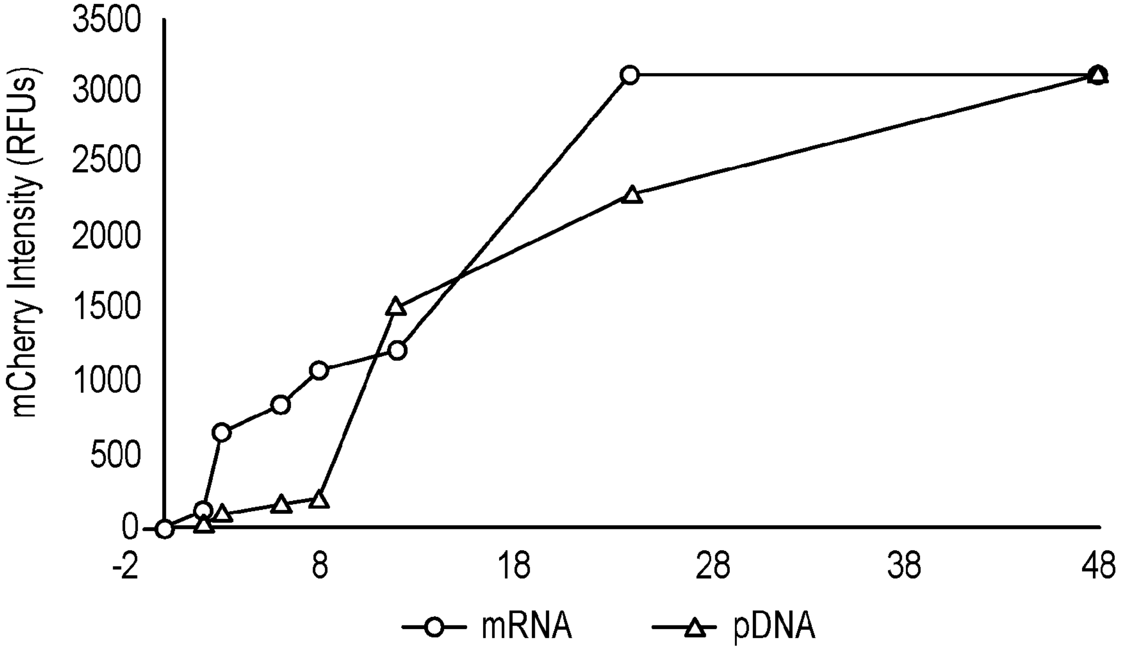
FIG. 8: The results obtained from the transfection of H1299 Cells with pDNA versus mRNA PD3(MN) Nanoparticles as described in Example 13. H1299 cells were treated with nanoparticles prepared with mRNA or pDNA. Transfection kinetics was monitored live using an Incucyte to fluorescently image the cells and the instrument software was used to quantify total red fluorescence intensity as a measure of transfection. mRNA does not require complicated nuclear localization for successful transgene expression and has been demonstrated to promote faster expression kinetics than when DNA is delivered. Our NPs were demonstrated to successfully package and delivery mRNA and expectedly achieve faster expression kinetics then when DNA was delivered. These results shows mRNA expression is significantly faster, however by 48 hours, similar levels of expression is achieved as when pDNA is delivered.

H1299 were seeded in 96-well plates targeting an 80% confluency within 24 hours. After a 24-hour recovery period, the NPs were added to the cells at 0.2 μg per well in culture media (1:10 dilution). After a 4-hour period, the NP supplemented media was removed, and fresh culture media was added. mCherry was imaged using the Incucyte (EssenBio). The results are shown in FIG. 8.

Example 14 pDNA and mRNA Transfection In Vivo

Intramuscular Delivery

Figure 9:
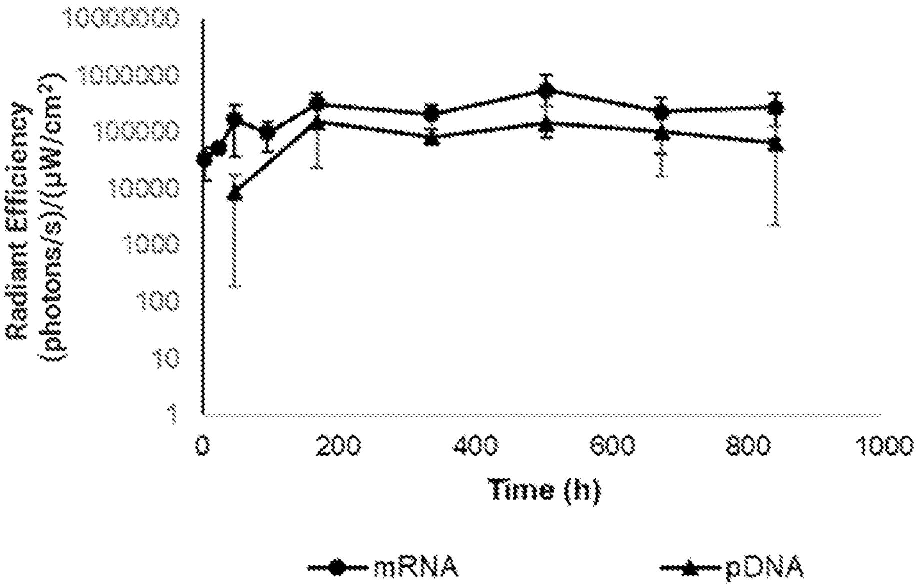
FIG. 9: The results obtained from the luciferase mouse expression experiment described in Example 14. CD mice were treated with pDNA or mRNA complexed with MeO PEG-PD3(MN) intramuscularly. Expression was assessed using IVIS. Luminescence was collected in quadruplicate and presented as the mean+/−standard deviation. These results shows both mRNA and pDNA can be delivered intramuscularly in vivo using the PD platform where mRNA NPs have faster expression kinetics.

NPs were prepared with MeO PEG-PD3(MN) as described in Examples 4 & 5. BALB/C mice were treated with 5 μg of complexed cleancap mRNA (Trilink, San Diego CA) or Gwiz DNA (Genlantis, San Diego CA) encoding luciferase per limb. Expression was assessed weekly using IVIS (Perkin Elmer). Luminescence was collected in quadruplicate and presented as the mean+/−standard deviation. The results are shown in FIG. 9.

Example 15 mRNA Therapeutic Expression In Vivo

Intravenous Delivery

Figure 10:
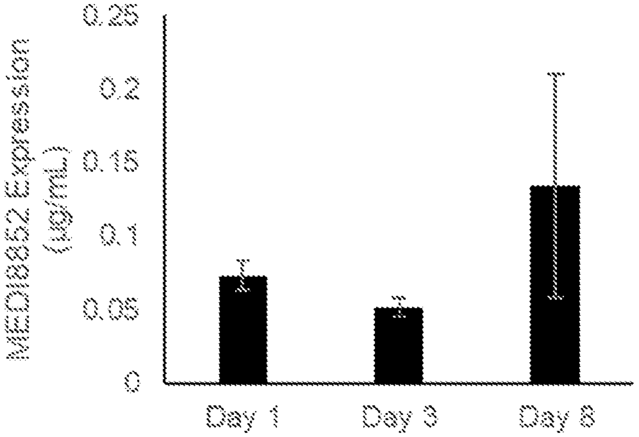
FIG. 10: The results obtained from the anti-Flu mAb MEDI8852 expression in mice experiment as described in Example 15. BALB/c mice treated with mRNA NPs via IV injection and MEDI8852 expression was quantified via ELISA. These results shows significant levels of mAb was detected over an 8 day period and confirm the capacity of PD to express therapeutic proteins in vivo.

NP were prepared with MeO-PD3(MN) and mRNA encoding MEDI8852 as described in Example 5. BALB/C mice were administered the NP intravenously through a trail vein injection (20 μg per mouse). Expression was assessed weekly using IVIS (Perkin Elmer). Luminescence was collected in quadruplicate and presented as the mean+/−standard deviation. The results are shown in FIG. 10.

Example 16 mRNA Targeted Transfection of Primary T-Cells

T-Cell Targeted NP Preparation and Characterization

In Vitro Transfections

Figure 11:
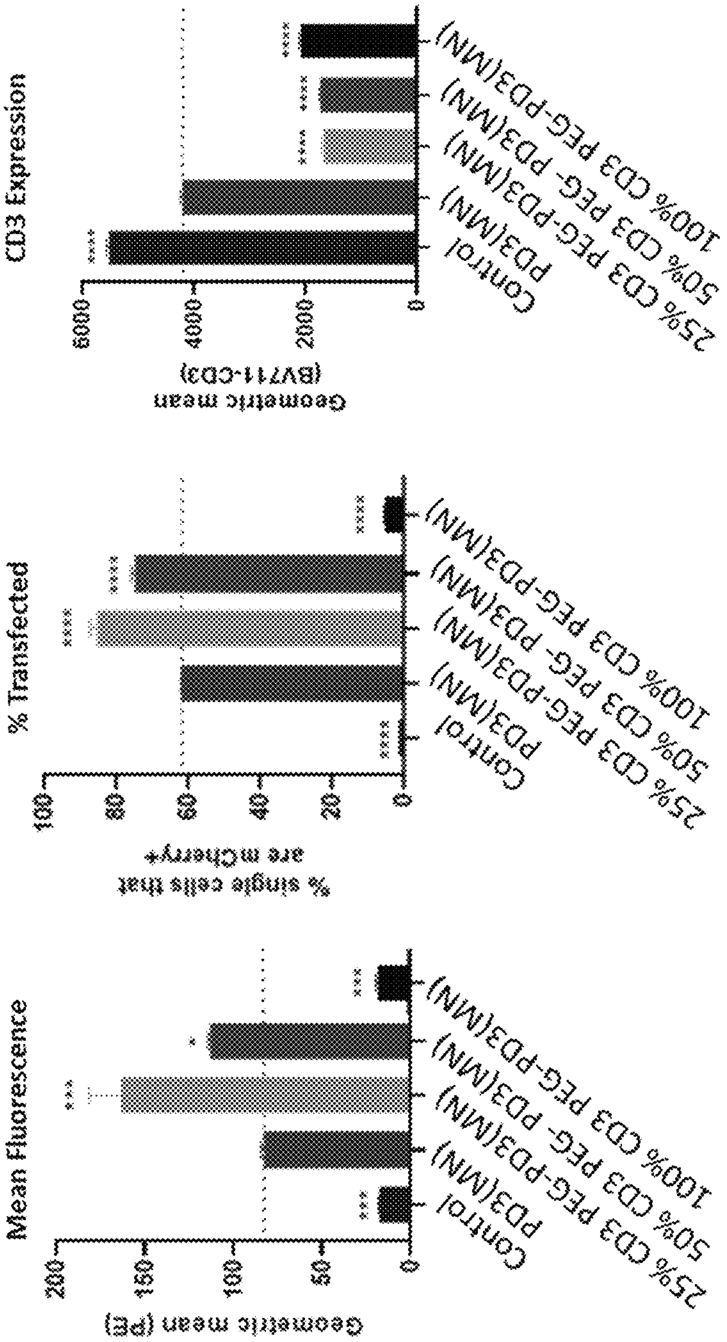
FIG. 11: The results obtained from the transfection of non-activated primary T-cells with mCherry mRNA/PD3 (MN) NPs with different displays of anti-CD3 targeted fab as described in Example 16. These results shows non-targeted NPs have the capacity to transfect T-cells; however CD3-targeting significantly enhances delivery when the targeting fab is displayed at low (25%) to moderate (50%) levels.

Fresh primary T-cells (similar to those obtainable from Cellero, Lowell, MA, but fresh not frozen) were seeded in 24-well plates (3e6/well) in RPMI1640 media (Sigma). After a 24-hour recovery period, NPs were then added to the cells at 100 UM per well in OPTI-MEM. The NPs were prepared as described in Example 6 with cleancap mRNA encoding mcherry (Trilink, San Diego, CA) and a mixture of PD3(MN) and Mal-PEG-PD3(MN). NPs were prepared with 0, 25, 50, and 100% Mal-PEG-PD3(MN) and subsequently conjugated with anti-CD3 fab as described in Example 6. After a 4-hour period, the NP supplemented media was removed and fresh culture media was added. RFP was imaged using the Incucyte (EssenBio) and quantified using flow cytometry. The results are shown in FIG. 11 where A) presents the average mcherry intensity, B) the percent of cells transfected and C) surface expression of CD3.

Example 17 siRNA Transfections In Vitro Study a) Cell Culture

Colo205 and SW480 cell lines were obtained from ATTC (Manassas, Virginia). Cultures were maintained in Roswell Park Memorial Institute (RPMI) growth medium (Gibco) supplemented with 10% fetal bovine serum (FBS) at 37° C. and 5% CO2. Colo205 and SW480 CTNNB1 shRNA cell lines were generated via lentiviral transduction of doxycycline-inducible human CTNNB1 shRNA (Dharmacon/Horizon Discovery, Lafayette, CO).

b) TopFlash CTNNB1 Reporter Assay and Western Blot

Figure 12:
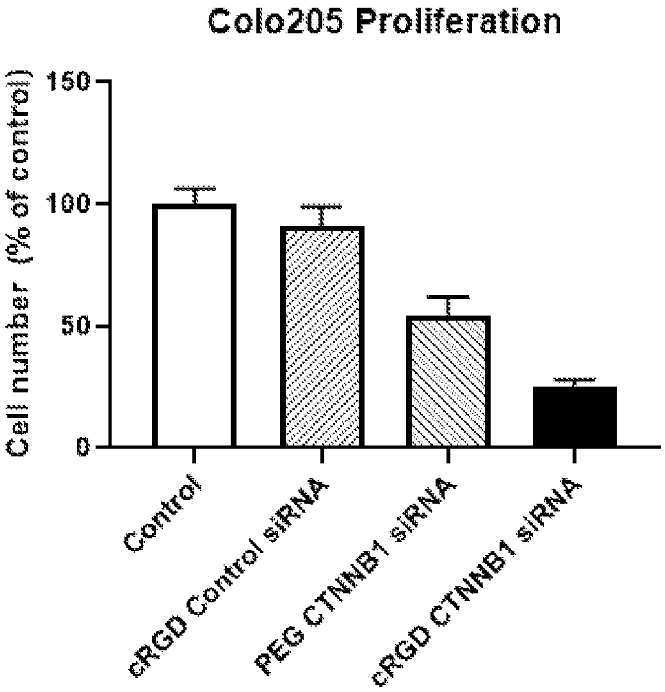
FIG. 12: The results obtained from the CTNNB1 silencing was monitored via a reporter assay and western blot as described in Example 17. The capacity of NPs to delivery siRNA was demonstrated in colon cancer cell line SW480 targeting oncogene CTNNB1. PD3(MN) and PD3(TM) with 1% (w/w) DOPE:DOTMA=1:1 were demonstrated to effectively silence CTNNB1 over a minimum of 5 days via western blot. These results shows PD NPs can deliver siRNA to target cells efficiently.
Figure 13A:
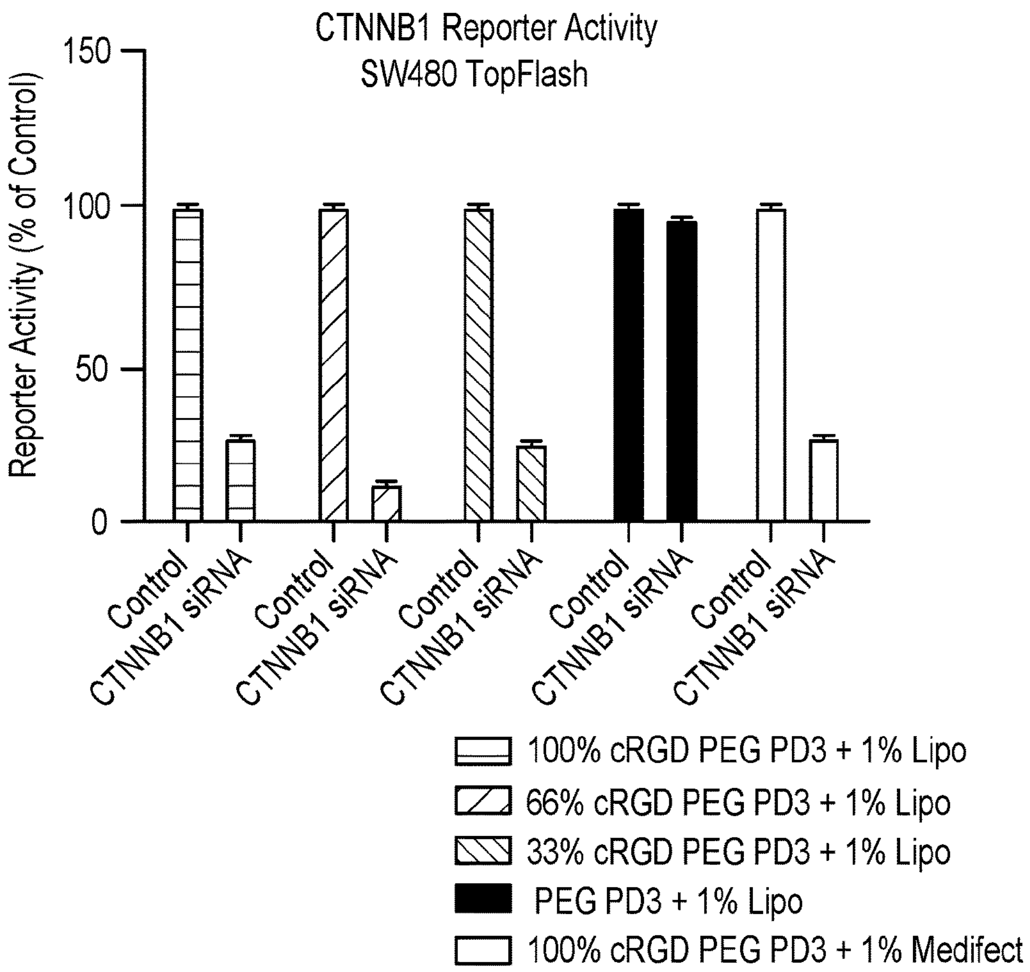
FIG. 13A, FIG. 13B and FIG. 13C: The results obtained from silencing of Catenin-B with PD3(MN) NPs with different displays of targeting peptide cRGD as described in Example 18. CTNNB1 Reporter Activity SW480 TopFlash (FIG. 13A), CTNNB1 Protein Levels SW480 (FIG. 13B) and Colo205 Proliferation (FIG. 13C). For many applications, localized delivery is required. To determine whether "on/off" delivery could be achieved with the NP platform, PEGylated NPs were prepared with different amounts of cRGD display and used to transfect colon cancer cell lines SW480 and Colo205. PEGylation was determined to stop or decrease silencing, while the instalment of cRGD on the NP reinstated NP activity. These results shows PEGylation can be used to decreased non-specific cellular uptake and targeting can be used to restore NP activity.
Figure 13B:
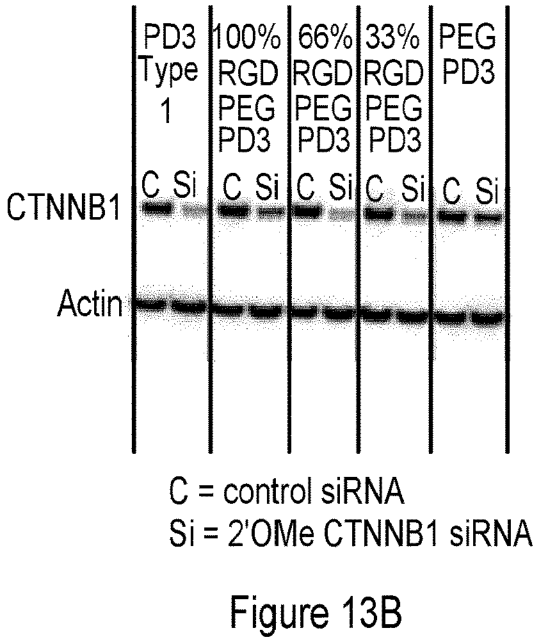

SW480 tumor cells (ATCC, Manassas, VA) were stably transduced with the TCF1 TopFlash luciferase reporter (EMD Millipore, Burlington, MA). SW480 TopFlash cells were seeded at a density of 2.0×105 cells per well in 6 well dishes and treated with cholesterol-conjugated siRNA (Accell siRNA) or siRNA NPs as described above for 48-72 hours. Nanoparticles were prepared as described in Example 5 with mixtures of PD3(MN) or MeO-PEG-PD (MN) and cRGD-PEG-PD (MN) with 0, 33, 66 or 100% cRGD-targeting. Cells were lysed and processed using BrightGlo reagent (Promega, Madison WI), transferred to a 96 well plate, and luciferase reporter activity was measured using an Envision X (Perkin Elmer, Waltham MA). The TopFlash results for PD3(MN): cRGD-PEG-PD3(MN) are shown in FIG. 12. The TopFlash results for MeO-PEG-PD3(MN): cRGD-PEG-PD3(MN) are shown in FIG. 13A. Cell lysate was also assessed 5 days post for CTNNB1 expression using standard Western blot protocols as shown in FIG. 13B.

c) CTNNB1 Western Blot and Cell Proliferation Assay

Figure 13C:
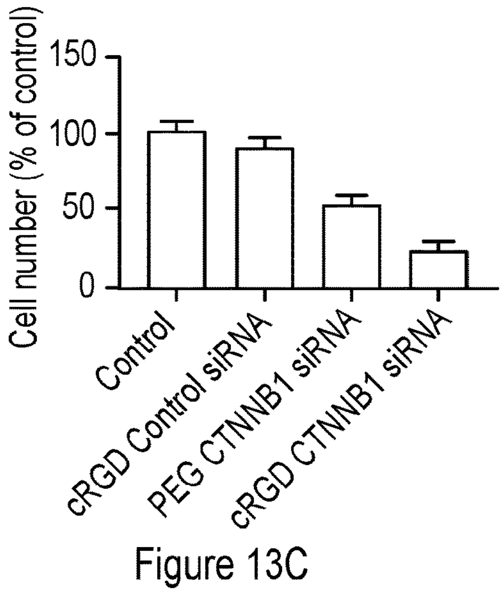

Colo205 cells were plated at a density of 2.0×105 cells per well in 6 well plates. As a control, cholesterol conjugated siRNAs were used to treat the cells. Specifically, 500 nM of Accell control non-targeted siRNA and Accell CTNNB1 siRNA were added to cells in 1 ml per well of Accell transfection medium purchased from Dharmacon/Horizon Discovery {Peje}ixxi0GS). Cholesterol conjugation promotes siRNA delivery at high concentrations. 2 ml of RPMI+10% FBS was added per well 48 hours after transfection. For experiments in which Colo205 cells were treated with CTNNB1 siRNA encapsulating NPs, cells were seeded at a density of 2.0×105 cells per well in 6 well plates. Nanoparticles were prepared as described in Example 5 with mixtures of MeO-PEG-PD (MN) and cRGD-PEG-PD (MN) with 0 or 66% cRGD-PD and 1% (w/w siRNA) lipofectin. Growth medium was replaced with 900 μl of optimal-minimal essential media (OPTIMEM) and 100 μl of NP formulation was added per well (100 μM of mRNA per well). 2 ml of RPMI+10% FBS was added per well 16 hours post transfection. For the cell proliferation assay, cells were harvested and counted 72 to 96 hours post transfection using a ViCell XR cell counter as shown in FIG. 13C.

Example 18

Figure 14:
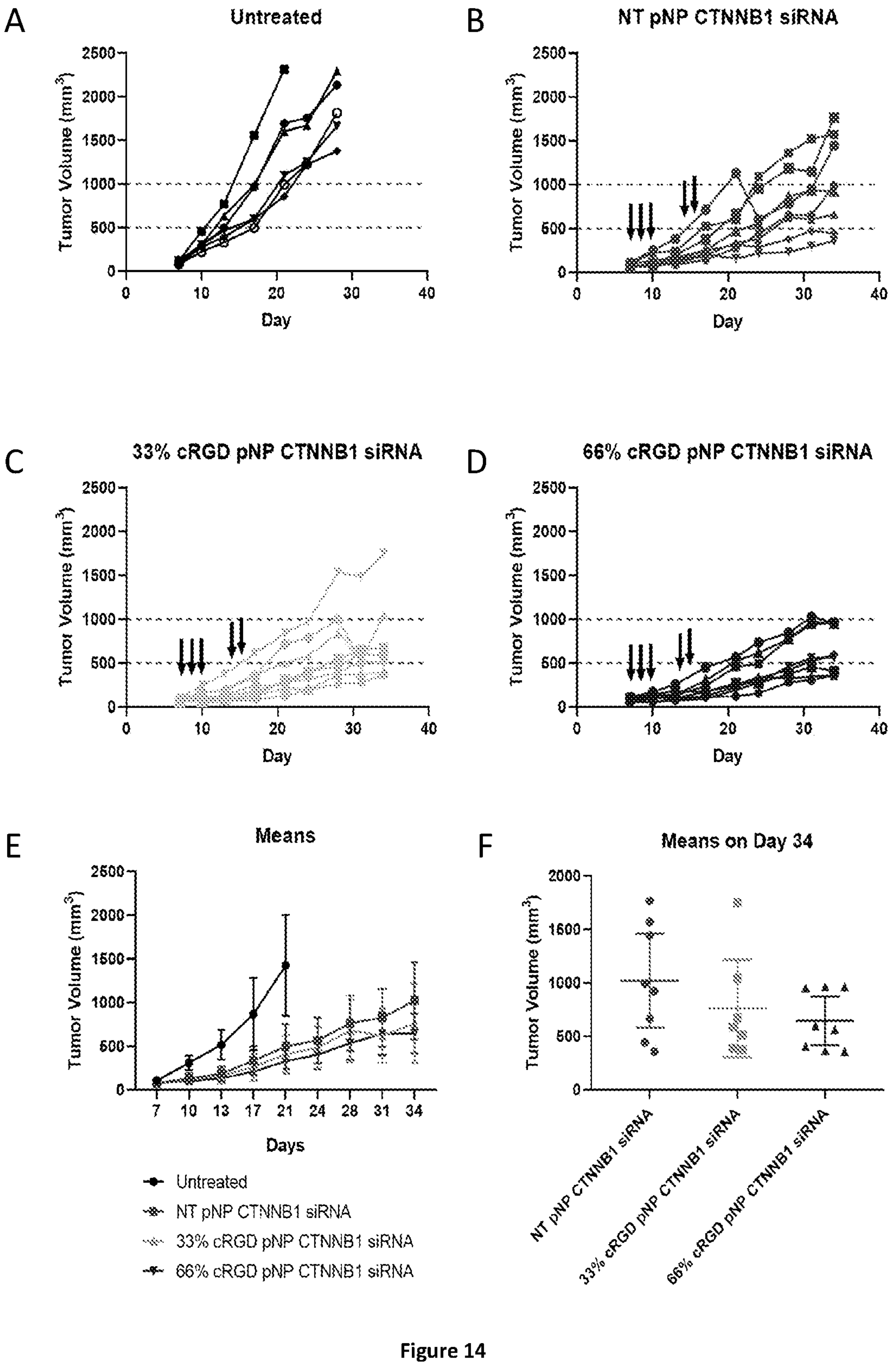
FIG. 14: The results obtained from the tumor volume in mouse metastatic colon cancer model as described in Example 18. Mice with established colon cancer cell line Colo205 tumors were intravenously administered NPs with various degrees of cRGD targeting on day 8, 9, 15, and 16 (indicated by black arrows). Groups included non-treated (A), mice administer non-targeted NPs (B), and mice administered targeted nanoparticles with moderate (C) to high cRGD (D) display where each data set represents one mouse. The means over time (E) and the final day of the study (F) were also determined. In vivo translation of the targeted siRNA NP was assessed in a mouse model. High levels of cRGD display were determined to slow tumor growth significantly compared to non-targeted NPs. These results shows cRGD targeted NPs can achieve enhanced siRNA delivery and highlights the importance of targeting ligand density.

Targeted siRNA Transfections In Vivo Study a) In Vivo Tumor Growth Inhibition Assays Seven-week-old female nude mice were injected with 5.0×106 Colo205 cells subcutaneously in 200 μl of PBS. When the average tumor volume reached approximately 100 $mm^3$, mice were randomized into treatment groups and received intravenous NP (0, 33, and 66% cRGD PD (MN): PEG-PD(MN) prepared as in Example 6) injections three days in a row, followed by two days in a row of injections a week later. Tumor measurements and mouse body weights were recorded two or three times per week for the duration of the experiment. Mice were euthanized when tumors reached a size of 2000 $mm^3$ or exhibited ulceration encompassing more than 50% of the tumor surface. The results are shown in FIG. 14.

Example 19

Hybrid RNA/DNA Peptide Dendron Nanoparticle (NP) Self-Assembly a) NP Preparation Cleancap mRNA encoding mCherry (Trilink, San Diego, CA) and gWiz™ DNA encoding GFP (Aldevron, Fargo, ND) were prepared in 1:1 mass ratios in 20 mM HEPES, pH 7.0 for a final concentration of 40 μg/mL. A solution of PD3(MN) (prepared as in Example 2) was prepared in 20 mM HEPES, pH 7.0 at concentrations corresponding to a final peptide dendron arginine:nucleic acid phosphate (N:P) ratio of 4:1. Nucleic acid solutions were added to PD3(MN) solutions at a 1:1 volume ratio and mixed thoroughly by pipetting. NPs were allowed to complex at room temperature for 30 minutes. The final concentration of nucleic acid in the NP solution was 20 μg/ml (10 μg/ml mRNA and μg/mL DNA). Control NPs were prepared with DNA and mRNA alone at a final nucleic concentration of 20 μg/mL.

b) Dynamic Light Scattering

Dynamic light scattering (DLS) data was collected using a Zetasizer ZS (Malvern), Green Laser and ZEN2112 Quartz cuvette. The hydrodynamic diameter and polydispersity index (PDI) was derived using cumulant fit analysis. All data points represent the mean of three or more individually prepared samples. The results are shown in Table 8.

TABLE 8

The hydrodynamic diameter of NPs prepared with PD3(MN) and DNA, mRNA, or 1:1 ratio of DNA and mRNA as described in Example 19.

| Genetic Material | Hydrodynamic Diameter (nm) | Polydispersity Index |
|---|---|---|
| DNA NP | 56 ± 2 | 0.177 ± 0.005 |
| mRNA NP | 33 ± 2 | 0.190 ± 0.008 |
| DNA mRNA NP | 49 ± 2 | 0.187 ± 0.003 |

Figure 15:
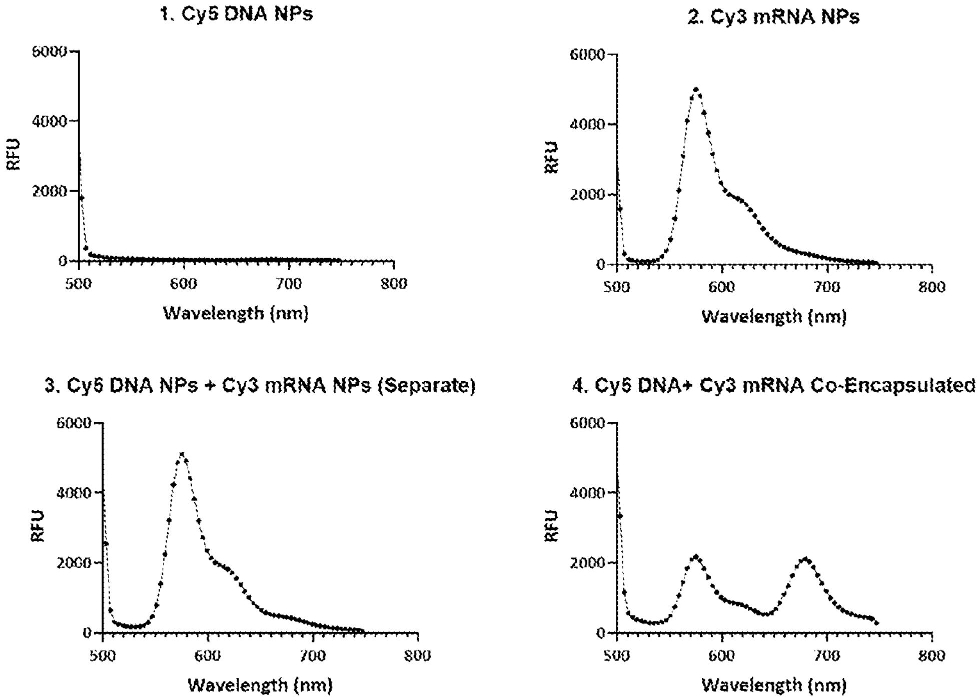
FIG. 15: The fluorescence spectra for NPs formulated with fluorescently labelled DNA (Cy5) and mRNA (Cy5) as described in Example 19. NPs with Cy5 labelled DNA (Graph 1) is not excited by the blue LED, so no fluorescence is detected at its emission wavelength (650-700 nm). NPs with Cy3 labelled mRNA (Graph 2) is excited and fluoresces at its emission peak around 550-600. Similarly, NPs prepared with Cy5 labelled DNA combined with NPs with Cy3 labelled mRNA (Graph 3) fluoresce at the Cy3 emission peak. Importantly, NPs prepared with a 1:1 mixture of Cy5 labelled DNA and Cy3 labelled mRNA (Graph 4) show an increase in emission at the Cy5 emission around 560-700 nm with a corresponding decrease in fluorescence intensity at the Cy3 emission peak around 550-600 nm. This indicates that the DNA and mRNA in sample 4 are in close proximity (<5 nm), enabling fluorescence resonance energy transfer (FRET) from the Cy3 fluorophore on the mRNA to excite the Cy5 fluorophore on the labelled DNA. This is evidence of co-encapsulation of the mRNA and DNA in peptide dendron NPs.

All measurements were collected in triplicate and presented as the mean +/− standard deviation.

c) Evaluation of Co-Encapsulation by Fluorescence Resonance Energy Transfer (FRET)

gWiz™ DNA encoding GFP (Aldevron, Fargo, ND) was labelled with Cy5, and Cleancap mRNA encoding mCherry (Trilink, San Diego, CA) was labelled with Cy3 using Label IT® Nucleic Acid Labelling Kits (Mirus Bio, Madison, WI). The following nanoparticles were formulated with PD3 (MN) as described above at a final nucleic acid concentration of 20 μg/mL:

1. Cy5 DNA+unlabelled DNA (1:1) co-encapsulated NPs
2. Cy3 mRNA+unlabelled mRNA (1:1) co-encapsulated NPs
3. Cy5 DNA NPs+Cy3 mRNA NPs (1:1) separately encapsulated.
4. Cy5 DNA+Cy3 mRNA (1:1) co-encapsulated NPs NPs were allowed to complex for 10 minutes prior to fluorescence analysis. The NPs in 3 listed above were formulated separately, allowed to complex for 10 minutes, then combined at a 1:1 ratio immediately prior to fluorescence analysis. Fluorescence analysis was performed using the NanoDrop™ 3300 Fluorospectrometer (ThermoFisher Scientific, Waltham, MA). 2 μl of NP sample was loaded onto the pedestal, and the sample was exciting using a blue LED. The fluorescence emission (relative fluorescence units, RFU) was measured between 450 and 750 nm wavelength. The fluorescence spectra of these NP samples are shown in FIG. 15.

d) Expression of mRNA and DNA in H1299 Cells

Figure 16:
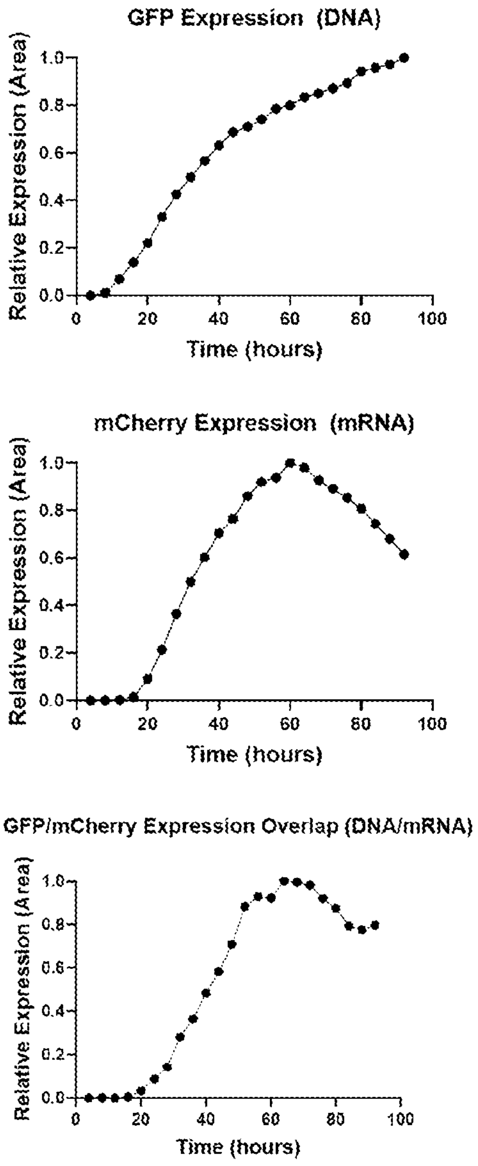
FIG. 16: The expression kinetics of mRNA/DNA hybrid PDID NPs in H1299 cells as described in Example 19. DNA expression is measured by GFP fluorescence area, and mRNA expression is measured by mCherry fluorescence area. GFP expression increases over 100 hours, while mRNA expression peaks around 60 hours. The amount of DNA/mRNA co-expression as quantified by overlapping fluorescence signal has similar kinetics to mRNA expression, peaking around 65 hours. These results show successful co-delivery of DNA and mRNA to cells.

NPs were formulated with PD3(MN) as described in a) with GFP DNA and mCherry mRNA at a 1:1 weight ratio for a final nucleic acid concentration of 20 μg/mL. H1299 cells were plated in a tissue culture-treated 96-well plate at 10,000 cells/well 24 h prior to treatment. Immediately prior to treatment, growth media was removed and replaced with 100 μL Opti-MEM™ I Reduced-Serum Medium (ThermoFisher, Waltham, MA). 10 μL of nanoparticle solution was added to each well (200 ng/well nucleic acid dose. Nanoparticles were incubated with cells for 4 hours, then the Opti-MEM and nanoparticles were removed and replaced with growth medium. Expression of GFP and mCherry proteins were monitored using an Incucyte Live-Cell Analysis System (Sartorius, Göttingen, Germany), which captured fluorescence images of the cells every 4 hours. Images were analysed using Incucyte software to determine fluorescent area in the green (GFP) and red (mCherry) channels as well as the area of red and green signal overlap. The signal was normalized to peak signal area to monitor expression kinetics. Results are shown in FIG. 16.

e) Expression of mRNA and DNA in $C_2C12$ Cells

Figure 17:
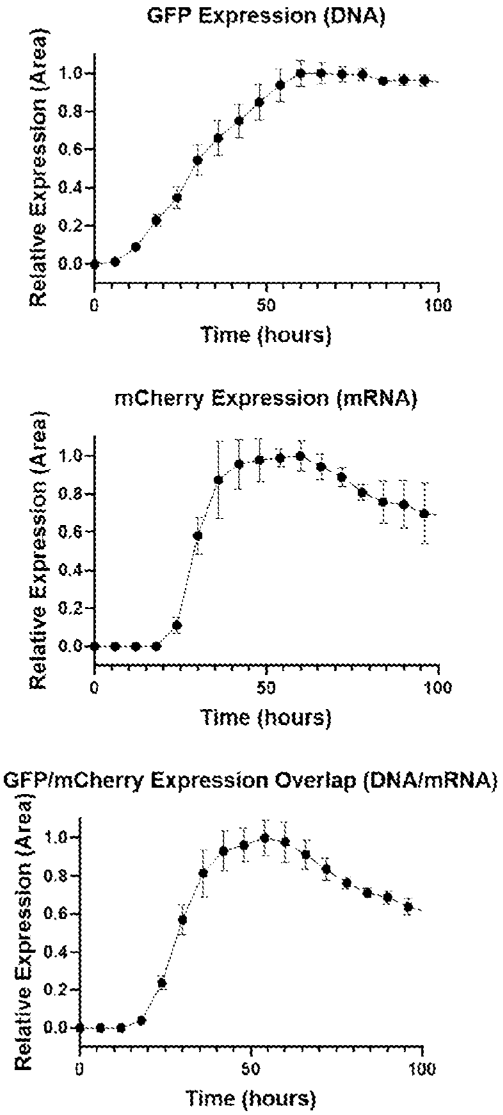
FIG. 17: The expression kinetics of mRNA/DNA hybrid PDID NPs in differentiated $C_2C12$ cells as described in Example 19. Differentiated C2C12 muscle cells have fused into myotubes and are non-dividing, making these cells difficult to transfect. DNA expression is measured by GFP fluorescence area, and mRNA expression is measured by mCherry expression area. GFP expression increases over 75 hours, followed by plateaued signal. mRNA expression peaks around 60 hours and slowly decreases. The amount of DNA/mRNA co-expression as quantified by overlapping fluorescence signal has similar kinetics to mRNA expression, peaking around 60 hours. These results show successful co-delivery of DNA and mRNA to non-dividing cells.

C2C12 cells were plated in a tissue culture-treated 96-well plate at 20,000 cells/well. Growth media was replaced with low serum differentiation media (DMEM+2% horse serum) and cultured for 7 days until fused elongated myotubes had formed. Nanoparticles were formulated with PD3(MN) as described in a) with GFP DNA and mCherry mRNA at a 1:1 weight ratio for a final nucleic acid concentration of 50 g/mL. Lipofectin® (DOTMA:DOPE (% w/w)=1) (Thermo Fischer Scientific, Waltham, MA) was added to the formulation. Lipofectin® was diluted in 20 mM HPES, pH 7.0 corresponding to a 1% w/w with nucleic acid. The Lipofectin® solution was added to PD3(MN) solution immediately before the addition of the RNA solution as previously described. Immediately prior to treatment, media was removed and replaced with 100 μL Opti-MEM™ I Reduced-Serum Medium (ThermoFisher, Waltham, MA). 10 μl of nanoparticle solution was added to each well (200 ng/well) nucleic acid dose. Nanoparticles were incubated with cells for 4 hours, then the Opti-MEM and nanoparticles were removed and replaced with growth medium. Expression of GFP and mCherry proteins were monitored using an Incucyte Live-Cell Analysis as described. Results are shown in FIG. 17.

SEQUENCE LISTING

```
Sequence total quantity: 48
SEQ ID NO: 1            moltype = AA  length = 4
FEATURE                 Location/Qualifiers
source                  1..4
                        mol_type = protein
                        organism = synthetic construct
SEQUENCE: 1
GGFG                                                                    4

SEQ ID NO: 2            moltype = AA  length = 4
FEATURE                 Location/Qualifiers
source                  1..4
                        mol_type = protein
                        organism = synthetic construct
SEQUENCE: 2
GFLG                                                                    4

SEQ ID NO: 3            moltype = AA  length = 21
FEATURE                 Location/Qualifiers
source                  1..21
                        mol_type = protein
                        organism = synthetic construct
MOD_RES                 1
                        note = ACETYLATION
CROSSLNK                11..16
                        note = Crosslinked via disulfide bonds
SEQUENCE: 3
KGGGAWSIID CSMNYCLYIE G                                                 21

SEQ ID NO: 4            moltype = AA  length = 5
FEATURE                 Location/Qualifiers
source                  1..5
                        mol_type = protein
                        organism = synthetic construct
REGION                  1..5
                        note = Circular
SITE                    4
                        note = D-Tyrosine
SEQUENCE: 4
RGDYK                                                                   5

SEQ ID NO: 5            moltype = AA  length = 7
FEATURE                 Location/Qualifiers
```

-continued

```
source                1..7
                      mol_type = protein
                      organism = synthetic construct
SITE                  3
                      note = Citrulline
SEQUENCE: 5
GVXGGSC                                                                  7

SEQ ID NO: 6          moltype = AA  length = 7
FEATURE               Location/Qualifiers
source                1..7
                      mol_type = protein
                      organism = synthetic construct
SEQUENCE: 6
ASSLNIA                                                                  7

SEQ ID NO: 7          moltype = AA  length = 16
FEATURE               Location/Qualifiers
source                1..16
                      mol_type = protein
                      organism = synthetic construct
SITE                  12
                      note = Citrulline
SITE                  3
                      note = Side chain of the lysine is linked via an amide
                       linkage to another sequence
SITE                  6
                      note = Side chain of the lysine is linked via an amide
                       linkage to another sequence
SITE                  9
                      note = Side chain of the lysine is linked via an amide
                       linkage to another sequence
SITE                  1..16
                      note = This sequence is one part of a branched amino acid
                       sequence
SEQUENCE: 7
LRKLRKLRKG VXGGSC                                                        16

SEQ ID NO: 8          moltype = AA  length = 8
FEATURE               Location/Qualifiers
source                1..8
                      mol_type = protein
                      organism = synthetic construct
SITE                  3
                      note = Side chain of the lysine is linked via an amide
                       linkage to another sequence
SITE                  6
                      note = Side chain of the lysine is linked via an amide
                       linkage to another sequence
SITE                  8
                      note = C-terminal amino acid is linked to another sequence
SITE                  1..8
                      note = This sequence is one part of a branched amino acid
                       sequence
SEQUENCE: 8
LRKLRKLR                                                                 8

SEQ ID NO: 9          moltype = AA  length = 5
FEATURE               Location/Qualifiers
source                1..5
                      mol_type = protein
                      organism = synthetic construct
SITE                  3
                      note = Side chain of the lysine is linked via an amide
                       linkage to another sequence
SITE                  5
                      note = C-terminal amino acid is linked to another sequence
SITE                  1..5
                      note = This sequence is one part of a branched amino acid
                       sequence
SEQUENCE: 9
LRKLR                                                                    5

SEQ ID NO: 10         moltype = AA  length = 19
FEATURE               Location/Qualifiers
source                1..19
                      mol_type = protein
                      organism = synthetic construct
SITE                  15
```

```
                        note = Citrulline
SITE                    4
                        note = Side chain of the lysine is linked via an amide
                         linkage to another sequence
SITE                    8
                        note = Side chain of the lysine is linked via an amide
                         linkage to another sequence
SITE                    12
                        note = Side chain of the lysine is linked via an amide
                         linkage to another sequence
SITE                    1..19
                        note = This sequence is one part of a branched amino acid
                         sequence
SEQUENCE: 10
RLKKRLKKRL KKGVXGGSC                                                   19

SEQ ID NO: 11           moltype = AA  length = 11
FEATURE                 Location/Qualifiers
source                  1..11
                        mol_type = protein
                        organism = synthetic construct
SITE                    4
                        note = Side chain of the lysine is linked via an amide
                         linkage to another sequence
SITE                    8
                        note = Side chain of the lysine is linked via an amide
                         linkage to another sequence
SITE                    11
                        note = C-terminal amino acid is linked to another sequence
SITE                    1..11
                        note = This sequence is one part of a branched amino acid
                         sequence
SEQUENCE: 11
RLKKRLKKRL K                                                           11

SEQ ID NO: 12           moltype = AA  length = 7
FEATURE                 Location/Qualifiers
source                  1..7
                        mol_type = protein
                        organism = synthetic construct
SITE                    4
                        note = Side chain of the lysine is linked via an amide
                         linkage to another sequence
SITE                    7
                        note = C-terminal amino acid is linked to another sequence
SITE                    1..7
                        note = This sequence is one part of a branched amino acid
                         sequence
SEQUENCE: 12
RLKKRLK                                                                7

SEQ ID NO: 13           moltype = AA  length = 19
FEATURE                 Location/Qualifiers
source                  1..19
                        mol_type = protein
                        organism = synthetic construct
SITE                    15
                        note = Citrulline
SITE                    4
                        note = Side chain of the lysine is linked via an amide
                         linkage to another sequence
SITE                    8
                        note = Side chain of the lysine is linked via an amide
                         linkage to another sequence
SITE                    12
                        note = Side chain of the lysine is linked via an amide
                         linkage to another sequence
SITE                    1..19
                        note = This sequence is one part of a branched amino acid
                         sequence
SEQUENCE: 13
KLRKKLRKKL RKGVXGGSC                                                   19

SEQ ID NO: 14           moltype = AA  length = 11
FEATURE                 Location/Qualifiers
source                  1..11
                        mol_type = protein
                        organism = synthetic construct
SITE                    4
```

```
                        note = Side chain of the lysine is linked via an amide
                         linkage to another sequence
SITE                    8
                        note = Side chain of the lysine is linked via an amide
                         linkage to another sequence
SITE                    11
                        note = C-terminal amino acid is linked to another sequence
SITE                    1..11
                        note = This sequence is one part of a branched amino acid
                         sequence
SEQUENCE: 14
KLRKKLRKKL R                                                                   11

SEQ ID NO: 15           moltype = AA  length = 7
FEATURE                 Location/Qualifiers
source                  1..7
                        mol_type = protein
                        organism = synthetic construct
SITE                    4
                        note = Side chain of the lysine is linked via an amide
                         linkage to another sequence
SITE                    7
                        note = C-terminal amino acid is linked to another sequence
SITE                    1..7
                        note = This sequence is one part of a branched amino acid
                         sequence
SEQUENCE: 15
KLRKKLR                                                                        7

SEQ ID NO: 16           moltype = AA  length = 19
FEATURE                 Location/Qualifiers
source                  1..19
                        mol_type = protein
                        organism = synthetic construct
SITE                    15
                        note = Citrulline
SITE                    4
                        note = Side chain of the lysine is linked via an amide
                         linkage to another sequence
SITE                    8
                        note = Side chain of the lysine is linked via an amide
                         linkage to another sequence
SITE                    12
                        note = Side chain of the lysine is linked via an amide
                         linkage to another sequence
SITE                    1..19
                        note = This sequence is one part of a branched amino acid
                         sequence
SEQUENCE: 16
HLRKHLRKHL RKGVXGGSC                                                           19

SEQ ID NO: 17           moltype = AA  length = 11
FEATURE                 Location/Qualifiers
source                  1..11
                        mol_type = protein
                        organism = synthetic construct
SITE                    4
                        note = Side chain of the lysine is linked via an amide
                         linkage to another sequence
SITE                    8
                        note = Side chain of the lysine is linked via an amide
                         linkage to another sequence
SITE                    11
                        note = C-terminal amino acid is linked to another sequence
SITE                    1..11
                        note = This sequence is one part of a branched amino acid
                         sequence
SEQUENCE: 17
HLRKHLRKHL R                                                                   11

SEQ ID NO: 18           moltype = AA  length = 7
FEATURE                 Location/Qualifiers
source                  1..7
                        mol_type = protein
                        organism = synthetic construct
SITE                    4
                        note = Side chain of the lysine is linked via an amide
                         linkage to another sequence
SITE                    7
```

-continued

```
                      note = C-terminal amino acid is linked to another sequence
SITE                  1..7
                      note = This sequence is one part of a branched amino acid
                       sequence
SEQUENCE: 18
HLRKHLR                                                              7

SEQ ID NO: 19         moltype = AA  length = 16
FEATURE               Location/Qualifiers
source                1..16
                      mol_type = protein
                      organism = synthetic construct
SITE                  2
                      note = N6-(2-morpholinoacetyl)-L-lysine
SITE                  5
                      note = N6-(2-morpholinoacetyl)-L-lysine
SITE                  8
                      note = N6-(2-morpholinoacetyl)-L-lysine
SITE                  3
                      note = Side chain of the lysine is linked via an amide
                       linkage to another sequence
SITE                  6
                      note = Side chain of the lysine is linked via an amide
                       linkage to another sequence
SITE                  9
                      note = Side chain of the lysine is linked via an amide
                       linkage to another sequence
SITE                  1..16
                      note = This sequence is one part of a branched amino acid
                       sequence
SITE                  12
                      note = Citrulline
SEQUENCE: 19
LXKLXKLXKG VXGGSC                                                    16

SEQ ID NO: 20         moltype = AA  length = 8
FEATURE               Location/Qualifiers
source                1..8
                      mol_type = protein
                      organism = synthetic construct
SITE                  2
                      note = N6-(2-morpholinoacetyl)-L-lysine
SITE                  5
                      note = N6-(2-morpholinoacetyl)-L-lysine
SITE                  8
                      note = N6-(2-morpholinoacetyl)-L-lysine
SITE                  3
                      note = Side chain of the lysine is linked via an amide
                       linkage to another sequence
SITE                  6
                      note = Side chain of the lysine is linked via an amide
                       linkage to another sequence
SITE                  8
                      note = C-terminal amino acid is linked to another sequence
SITE                  1..8
                      note = This sequence is one part of a branched amino acid
                       sequence
SEQUENCE: 20
LXKLXKLX                                                             8

SEQ ID NO: 21         moltype = AA  length = 16
FEATURE               Location/Qualifiers
source                1..16
                      mol_type = protein
                      organism = synthetic construct
SITE                  2
                      note = N6-(6-morpholinonicotinoyl)-L-lysine
SITE                  5
                      note = N6-(6-morpholinonicotinoyl)-L-lysine
SITE                  8
                      note = N6-(6-morpholinonicotinoyl)-L-lysine
SITE                  12
                      note = Citrulline
SITE                  3
                      note = Side chain of the lysine is linked via an amide
                       linkage to another sequence
SITE                  6
                      note = Side chain of the lysine is linked via an amide
                       linkage to another sequence
```

-continued

```
SITE                    9
                        note = Side chain of the lysine is linked via an amide
                         linkage to another sequence
SITE                    1..16
                        note = This sequence is one part of a branched amino acid
                         sequence
SEQUENCE: 21
LXKLXKLXKG VXGGSC                                                  16

SEQ ID NO: 22           moltype = AA  length = 8
FEATURE                 Location/Qualifiers
source                  1..8
                        mol_type = protein
                        organism = synthetic construct
SITE                    2
                        note = N6-(6-morpholinonicotinoyl)-L-lysine
SITE                    5
                        note = N6-(6-morpholinonicotinoyl)-L-lysine
SITE                    8
                        note = N6-(6-morpholinonicotinoyl)-L-lysine
SITE                    3
                        note = Side chain of the lysine is linked via an amide
                         linkage to another sequence
SITE                    6
                        note = Side chain of the lysine is linked via an amide
                         linkage to another sequence
SITE                    8
                        note = C-terminal amino acid is linked to another sequence
SITE                    1..8
                        note = This sequence is one part of a branched amino acid
                         sequence
SEQUENCE: 22
LXKLXKLX                                                           8

SEQ ID NO: 23           moltype = AA  length = 16
FEATURE                 Location/Qualifiers
source                  1..16
                        mol_type = protein
                        organism = synthetic construct
SITE                    2
                        note = N6-(thiomorpholine-3-carbonyl)-L-lysine
SITE                    5
                        note = N6-(thiomorpholine-3-carbonyl)-L-lysine
SITE                    8
                        note = N6-(thiomorpholine-3-carbonyl)-L-lysine
SITE                    12
                        note = Citrulline
SITE                    3
                        note = Side chain of the lysine is linked via an amide
                         linkage to another sequence
SITE                    6
                        note = Side chain of the lysine is linked via an amide
                         linkage to another sequence
SITE                    9
                        note = Side chain of the lysine is linked via an amide
                         linkage to another sequence
SITE                    1..16
                        note = This sequence is one part of a branched amino acid
                         sequence
SEQUENCE: 23
LXKLXKLXKG VXGGSC                                                  16

SEQ ID NO: 24           moltype = AA  length = 8
FEATURE                 Location/Qualifiers
source                  1..8
                        mol_type = protein
                        organism = synthetic construct
SITE                    2
                        note = N6-(thiomorpholine-3-carbonyl)-L-lysine
SITE                    5
                        note = N6-(thiomorpholine-3-carbonyl)-L-lysine
SITE                    8
                        note = N6-(thiomorpholine-3-carbonyl)-L-lysine
SITE                    3
                        note = Side chain of the lysine is linked via an amide
                         linkage to another sequence
SITE                    6
                        note = Side chain of the lysine is linked via an amide
                         linkage to another sequence
```

-continued

```
SITE                    8
                        note = C-terminal amino acid is linked to another sequence
SITE                    1..8
                        note = This sequence is one part of a branched amino acid
                         sequence
SEQUENCE: 24
LXKLXKLX                                                                   8

SEQ ID NO: 25           moltype = AA  length = 19
FEATURE                 Location/Qualifiers
source                  1..19
                        mol_type = protein
                        organism = synthetic construct
SITE                    3
                        note = N6-(2-morpholinoacetyl)-L-lysine
SITE                    4
                        note = Side chain of the lysine is linked via an amide
                         linkage to another sequence
SITE                    8
                        note = Side chain of the lysine is linked via an amide
                         linkage to another sequence
SITE                    12
                        note = Side chain of the lysine is linked via an amide
                         linkage to another sequence
SITE                    1..19
                        note = This sequence is one part of a branched amino acid
                         sequence
SITE                    15
                        note = Citrulline
SITE                    7
                        note = N6-(2-morpholinoacetyl)-L-lysine
SITE                    11
                        note = N6-(2-morpholinoacetyl)-L-lysine
SEQUENCE: 25
RLXKRLXKRL XKGVXGGSC                                                       19

SEQ ID NO: 26           moltype = AA  length = 11
FEATURE                 Location/Qualifiers
source                  1..11
                        mol_type = protein
                        organism = synthetic construct
SITE                    3
                        note = N6-(2-morpholinoacetyl)-L-lysine
SITE                    7
                        note = N6-(2-morpholinoacetyl)-L-lysine
SITE                    11
                        note = N6-(2-morpholinoacetyl)-L-lysine
SITE                    4
                        note = Side chain of the lysine is linked via an amide
                         linkage to another sequence
SITE                    8
                        note = Side chain of the lysine is linked via an amide
                         linkage to another sequence
SITE                    11
                        note = C-terminal amino acid is linked to another sequence
SITE                    1..11
                        note = This sequence is one part of a branched amino acid
                         sequence
SEQUENCE: 26
RLXKRLXKRL X                                                               11

SEQ ID NO: 27           moltype = AA  length = 7
FEATURE                 Location/Qualifiers
source                  1..7
                        mol_type = protein
                        organism = synthetic construct
SITE                    3
                        note = N6-(2-morpholinoacetyl)-L-lysine
SITE                    7
                        note = N6-(2-morpholinoacetyl)-L-lysine
SITE                    4
                        note = Side chain of the lysine is linked via an amide
                         linkage to another sequence
SITE                    7
                        note = C-terminal amino acid is linked to another sequence
SITE                    1..7
                        note = This sequence is one part of a branched amino acid
                         sequence
SEQUENCE: 27
```

-continued

```
RLXKRLX                                                 7

SEQ ID NO: 28           moltype = AA  length = 19
FEATURE                 Location/Qualifiers
source                  1..19
                        mol_type = protein
                        organism = synthetic construct
SITE                    3
                        note = N6-(6-morpholinonicotinoyl)-L-lysine
SITE                    7
                        note = N6-(6-morpholinonicotinoyl)-L-lysine
SITE                    11
                        note = N6-(6-morpholinonicotinoyl)-L-lysine
SITE                    15
                        note = Citrulline
SITE                    4
                        note = Side chain of the lysine is linked via an amide
                         linkage to another sequence
SITE                    8
                        note = Side chain of the lysine is linked via an amide
                         linkage to another sequence
SITE                    12
                        note = Side chain of the lysine is linked via an amide
                         linkage to another sequence
SITE                    1..19
                        note = This sequence is one part of a branched amino acid
                         sequence
SEQUENCE: 28
RLXKRLXKRL XKGVXGGSC                                    19

SEQ ID NO: 29           moltype = AA  length = 11
FEATURE                 Location/Qualifiers
source                  1..11
                        mol_type = protein
                        organism = synthetic construct
SITE                    3
                        note = N6-(6-morpholinonicotinoyl)-L-lysine
SITE                    7
                        note = N6-(6-morpholinonicotinoyl)-L-lysine
SITE                    11
                        note = N6-(6-morpholinonicotinoyl)-L-lysine
SITE                    4
                        note = Side chain of the lysine is linked via an amide
                         linkage to another sequence
SITE                    8
                        note = Side chain of the lysine is linked via an amide
                         linkage to another sequence
SITE                    11
                        note = C-terminal amino acid is linked to another sequence
SITE                    1..11
                        note = This sequence is one part of a branched amino acid
                         sequence
SEQUENCE: 29
RLXKRLXKRL X                                            11

SEQ ID NO: 30           moltype = AA  length = 7
FEATURE                 Location/Qualifiers
source                  1..7
                        mol_type = protein
                        organism = synthetic construct
SITE                    3
                        note = N6-(6-morpholinonicotinoyl)-L-lysine
SITE                    4
                        note = Side chain of the lysine is linked via an amide
                         linkage to another sequence
SITE                    7
                        note = C-terminal amino acid is linked to another sequence
SITE                    1..7
                        note = This sequence is one part of a branched amino acid
                         sequence
SITE                    7
                        note = N6-(6-morpholinonicotinoyl)-L-lysine
SEQUENCE: 30
RLXKRLX                                                 7

SEQ ID NO: 31           moltype = AA  length = 19
FEATURE                 Location/Qualifiers
source                  1..19
                        mol_type = protein
```

```
                         organism = synthetic construct
SITE                     3
                         note = N6-(thiomorpholine-3-carbonyl)-L-lysine
SITE                     7
                         note = N6-(thiomorpholine-3-carbonyl)-L-lysine
SITE                     11
                         note = N6-(thiomorpholine-3-carbonyl)-L-lysine
SITE                     15
                         note = Citrulline
SITE                     4
                         note = Side chain of the lysine is linked via an amide
                          linkage to another sequence
SITE                     8
                         note = Side chain of the lysine is linked via an amide
                          linkage to another sequence
SITE                     12
                         note = Side chain of the lysine is linked via an amide
                          linkage to another sequence
SITE                     1..19
                         note = This sequence is one part of a branched amino acid
                          sequence
SEQUENCE: 31
RLXKRLXKRL XKGVXGGSC                                             19

SEQ ID NO: 32            moltype = AA  length = 11
FEATURE                  Location/Qualifiers
source                   1..11
                         mol_type = protein
                         organism = synthetic construct
SITE                     3
                         note = N6-(thiomorpholine-3-carbonyl)-L-lysine
SITE                     7
                         note = N6-(thiomorpholine-3-carbonyl)-L-lysine
SITE                     11
                         note = N6-(thiomorpholine-3-carbonyl)-L-lysine
SITE                     4
                         note = Side chain of the lysine is linked via an amide
                          linkage to another sequence
SITE                     8
                         note = Side chain of the lysine is linked via an amide
                          linkage to another sequence
SITE                     11
                         note = C-terminal amino acid is linked to another sequence
SITE                     1..11
                         note = This sequence is one part of a branched amino acid
                          sequence
SEQUENCE: 32
RLXKRLXKRL X                                                     11

SEQ ID NO: 33            moltype = AA  length = 7
FEATURE                  Location/Qualifiers
source                   1..7
                         mol_type = protein
                         organism = synthetic construct
SITE                     3
                         note = N6-(thiomorpholine-3-carbonyl)-L-lysine
SITE                     7
                         note = N6-(thiomorpholine-3-carbonyl)-L-lysine
SITE                     4
                         note = Side chain of the lysine is linked via an amide
                          linkage to another sequence
SITE                     7
                         note = C-terminal amino acid is linked to another sequence
SITE                     1..7
                         note = This sequence is one part of a branched amino acid
                          sequence
SEQUENCE: 33
RLXKRLX                                                          7

SEQ ID NO: 34            moltype = AA  length = 19
FEATURE                  Location/Qualifiers
source                   1..19
                         mol_type = protein
                         organism = synthetic construct
SITE                     1
                         note = N6-(2-morpholinoacetyl)-L-lysine
SITE                     5
                         note = N6-(2-morpholinoacetyl)-L-lysine
SITE                     9
```

-continued

```
                          note = N6-(2-morpholinoacetyl)-L-lysine
SITE                      4
                          note = Side chain of the lysine is linked via an amide
                           linkage to another sequence
SITE                      8
                          note = Side chain of the lysine is linked via an amide
                           linkage to another sequence
SITE                      12
                          note = Side chain of the lysine is linked via an amide
                           linkage to another sequence
SITE                      1..19
                          note = This sequence is one part of a branched amino acid
                           sequence
SITE                      15
                          note = Citrulline
SEQUENCE: 34
XLRKXLRKXL RKGVXGGSC                                                19

SEQ ID NO: 35             moltype = AA  length = 11
FEATURE                   Location/Qualifiers
source                    1..11
                          mol_type = protein
                          organism = unidentified
SITE                      1
                          note = N6-(2-morpholinoacetyl)-L-lysine
SITE                      5
                          note = N6-(2-morpholinoacetyl)-L-lysine
SITE                      9
                          note = N6-(2-morpholinoacetyl)-L-lysine
SITE                      4
                          note = Side chain of the lysine is linked via an amide
                           linkage to another sequence
SITE                      8
                          note = Side chain of the lysine is linked via an amide
                           linkage to another sequence
SITE                      11
                          note = C-terminal amino acid is linked to another sequence
SITE                      1..11
                          note = This sequence is one part of a branched amino acid
                           sequence
SEQUENCE: 35
XLRKXLRKXL R                                                        11

SEQ ID NO: 36             moltype = AA  length = 7
FEATURE                   Location/Qualifiers
source                    1..7
                          mol_type = protein
                          organism = synthetic construct
SITE                      1
                          note = N6-(2-morpholinoacetyl)-L-lysine
SITE                      5
                          note = N6-(2-morpholinoacetyl)-L-lysine
SITE                      4
                          note = Side chain of the lysine is linked via an amide
                           linkage to another sequence
SITE                      7
                          note = C-terminal amino acid is linked to another sequence
SITE                      1..7
                          note = This sequence is one part of a branched amino acid
                           sequence
SEQUENCE: 36
XLRKXLR                                                             7

SEQ ID NO: 37             moltype = AA  length = 19
FEATURE                   Location/Qualifiers
source                    1..19
                          mol_type = protein
                          organism = synthetic construct
SITE                      1
                          note = N6-(6-morpholinonicotinoyl)-L-lysine
SITE                      5
                          note = N6-(6-morpholinonicotinoyl)-L-lysine
SITE                      9
                          note = N6-(6-morpholinonicotinoyl)-L-lysine
SITE                      4
                          note = Side chain of the lysine is linked via an amide
                           linkage to another sequence
SITE                      8
                          note = Side chain of the lysine is linked via an amide
```

```
                         linkage to another sequence
SITE                    12
                        note = Side chain of the lysine is linked via an amide
                         linkage to another sequence
SITE                    1..19
                        note = This sequence is one part of a branched amino acid
                         sequence
SITE                    15
                        note = Citrulline
SEQUENCE: 37
XLRKXLRKXL RKGVXGGSC                                                19

SEQ ID NO: 38           moltype = AA  length = 11
FEATURE                 Location/Qualifiers
source                  1..11
                        mol_type = protein
                        organism = unidentified
SITE                    1
                        note = N6-(6-morpholinonicotinoyl)-L-lysine
SITE                    5
                        note = N6-(6-morpholinonicotinoyl)-L-lysine
SITE                    9
                        note = N6-(6-morpholinonicotinoyl)-L-lysine
SITE                    4
                        note = Side chain of the lysine is linked via an amide
                         linkage to another sequence
SITE                    8
                        note = Side chain of the lysine is linked via an amide
                         linkage to another sequence
SITE                    11
                        note = C-terminal amino acid is linked to another sequence
SITE                    1..11
                        note = This sequence is one part of a branched amino acid
                         sequence
SEQUENCE: 38
XLRKXLRKXL R                                                        11

SEQ ID NO: 39           moltype = AA  length = 7
FEATURE                 Location/Qualifiers
source                  1..7
                        mol_type = protein
                        organism = synthetic construct
SITE                    1
                        note = N6-(6-morpholinonicotinoyl)-L-lysine
SITE                    5
                        note = N6-(6-morpholinonicotinoyl)-L-lysine
SITE                    4
                        note = Side chain of the lysine is linked via an amide
                         linkage to another sequence
SITE                    7
                        note = C-terminal amino acid is linked to another sequence
SITE                    1..7
                        note = This sequence is one part of a branched amino acid
                         sequence
SEQUENCE: 39
XLRKXLR                                                             7

SEQ ID NO: 40           moltype = AA  length = 19
FEATURE                 Location/Qualifiers
source                  1..19
                        mol_type = protein
                        organism = synthetic construct
SITE                    1
                        note = N6-(thiomorpholine-3-carbonyl)-L-lysine
SITE                    9
                        note = N6-(thiomorpholine-3-carbonyl)-L-lysine
SITE                    15
                        note = Citrulline
SITE                    4
                        note = Side chain of the lysine is linked via an amide
                         linkage to another sequence
SITE                    8
                        note = Side chain of the lysine is linked via an amide
                         linkage to another sequence
SITE                    12
                        note = Side chain of the lysine is linked via an amide
                         linkage to another sequence
SITE                    1..19
                        note = This sequence is one part of a branched amino acid
```

```
                         sequence
SITE                    5
                        note = N6-(thiomorpholine-3-carbonyl)-L-lysine
SEQUENCE: 40
XLRKXLRKXL RKGVXGGSC                                          19

SEQ ID NO: 41           moltype = AA  length = 11
FEATURE                 Location/Qualifiers
source                  1..11
                        mol_type = protein
                        organism = synthetic construct
SITE                    1
                        note = N6-(thiomorpholine-3-carbonyl)-L-lysine
SITE                    9
                        note = N6-(thiomorpholine-3-carbonyl)-L-lysine
SITE                    4
                        note = Side chain of the lysine is linked via an amide
                         linkage to another sequence
SITE                    8
                        note = Side chain of the lysine is linked via an amide
                         linkage to another sequence
SITE                    11
                        note = C-terminal amino acid is linked to another sequence
SITE                    1..11
                        note = This sequence is one part of a branched amino acid
                         sequence
SITE                    5
                        note = N6-(thiomorpholine-3-carbonyl)-L-lysine
SEQUENCE: 41
XLRKXLRKXL R                                                  11

SEQ ID NO: 42           moltype = AA  length = 7
FEATURE                 Location/Qualifiers
source                  1..7
                        mol_type = protein
                        organism = synthetic construct
SITE                    1
                        note = N6-(thiomorpholine-3-carbonyl)-L-lysine
SITE                    5
                        note = N6-(thiomorpholine-3-carbonyl)-L-lysine
SITE                    4
                        note = Side chain of the lysine is linked via an amide
                         linkage to another sequence
SITE                    7
                        note = C-terminal amino acid is linked to another sequence
SITE                    1..7
                        note = This sequence is one part of a branched amino acid
                         sequence
SEQUENCE: 42
XLRKXLR                                                       7

SEQ ID NO: 43           moltype = AA  length = 19
FEATURE                 Location/Qualifiers
source                  1..19
                        mol_type = protein
                        organism = synthetic construct
SITE                    1
                        note = N6-(6-morpholinonicotinoyl)-L-lysine
SITE                    5
                        note = N6-(6-morpholinonicotinoyl)-L-lysine
SITE                    15
                        note = Citrulline
SITE                    4
                        note = Side chain of the lysine is linked via an amide
                         linkage to another sequence
SITE                    8
                        note = Side chain of the lysine is linked via an amide
                         linkage to another sequence
SITE                    12
                        note = Side chain of the lysine is linked via an amide
                         linkage to another sequence
SITE                    1..19
                        note = This sequence is one part of a branched amino acid
                         sequence
SITE                    9
                        note = N6-(6-morpholinonicotinoyl)-L-lysine
SEQUENCE: 43
XLRKXLRKXL RKGVXGGSC                                          19
```

-continued

```
SEQ ID NO: 44           moltype = AA  length = 11
FEATURE                 Location/Qualifiers
source                  1..11
                        mol_type = protein
                        organism = synthetic construct
SITE                    1
                        note = N6-(6-morpholinonicotinoyl)-L-lysine
SITE                    5
                        note = N6-(6-morpholinonicotinoyl)-L-lysine
SITE                    9
                        note = N6-(6-morpholinonicotinoyl)-L-lysine
SITE                    4
                        note = Side chain of the lysine is linked via an amide
                         linkage to another sequence
SITE                    8
                        note = Side chain of the lysine is linked via an amide
                         linkage to another sequence
SITE                    11
                        note = C-terminal amino acid is linked to another sequence
SITE                    1..11
                        note = This sequence is one part of a branched amino acid
                         sequence
SEQUENCE: 44
XLRKXLRKXL R                                                          11

SEQ ID NO: 45           moltype = AA  length = 7
FEATURE                 Location/Qualifiers
source                  1..7
                        mol_type = protein
                        organism = synthetic construct
SITE                    1
                        note = N6-(6-morpholinonicotinoyl)-L-lysine
SITE                    5
                        note = N6-(6-morpholinonicotinoyl)-L-lysine
SITE                    4
                        note = Side chain of the lysine is linked via an amide
                         linkage to another sequence
SITE                    7
                        note = C-terminal amino acid is linked to another sequence
SITE                    1..7
                        note = This sequence is one part of a branched amino acid
                         sequence
SEQUENCE: 45
XLRKXLR                                                               7

SEQ ID NO: 46           moltype = AA  length = 19
FEATURE                 Location/Qualifiers
source                  1..19
                        mol_type = protein
                        organism = synthetic construct
SITE                    1
                        note = N6-(thiomorpholine-3-carbonyl)-L-lysine
SITE                    5
                        note = N6-(thiomorpholine-3-carbonyl)-L-lysine
SITE                    15
                        note = Citrulline
SITE                    4
                        note = Side chain of the lysine is linked via an amide
                         linkage to another sequence
SITE                    8
                        note = Side chain of the lysine is linked via an amide
                         linkage to another sequence
SITE                    12
                        note = Side chain of the lysine is linked via an amide
                         linkage to another sequence
SITE                    1..19
                        note = This sequence is one part of a branched amino acid
                         sequence
SITE                    9
                        note = N6-(thiomorpholine-3-carbonyl)-L-lysine
SEQUENCE: 46
XLRKXLRKXL RKGVXGGSC                                                  19

SEQ ID NO: 47           moltype = AA  length = 11
FEATURE                 Location/Qualifiers
source                  1..11
                        mol_type = protein
                        organism = synthetic construct
SITE                    1
```

-continued

```
                        note = N6-(thiomorpholine-3-carbonyl)-L-lysine
SITE                    5
                        note = N6-(thiomorpholine-3-carbonyl)-L-lysine
SITE                    9
                        note = N6-(thiomorpholine-3-carbonyl)-L-lysine
SITE                    4
                        note = Side chain of the lysine is linked via an amide
                         linkage to another sequence
SITE                    8
                        note = Side chain of the lysine is linked via an amide
                         linkage to another sequence
SITE                    11
                        note = C-terminal amino acid is linked to another sequence
SITE                    1..11
                        note = This sequence is one part of a branched amino acid
                         sequence
SEQUENCE: 47
XLRKXLRKXL R                                                   11

SEQ ID NO: 48           moltype = AA  length = 7
FEATURE                 Location/Qualifiers
source                  1..7
                        mol_type = protein
                        organism = synthetic construct
SITE                    1
                        note = N6-(thiomorpholine-3-carbonyl)-L-lysine
SITE                    5
                        note = N6-(thiomorpholine-3-carbonyl)-L-lysine
SITE                    4
                        note = Side chain of the lysine is linked via an amide
                         linkage to another sequence
SITE                    7
                        note = C-terminal amino acid is linked to another sequence
SITE                    1..7
                        note = This sequence is one part of a branched amino acid
                         sequence
SEQUENCE: 48
XLRKXLR                                                        7
```

What is claimed is:

1. A peptide dendron comprising one or more residues derived from a modified lysine, wherein the residue derived from a modified lysine is selected from:

(2S)-2-amino-6-{[6-(morpholin-4-yl) pyridine-3-carbonyl]amino}hexanoic acid;

(2S)-2-amino-6-[(thiomorpholine-3-carbonyl) amino] hexanoic acid; and (2S)-2-amino-6-2-(morpholin-4-yl) acetamido]hexanoic acid.

2. The peptide dendron of claim 1, wherein the dendron comprises fewer than six generations.

3. The peptide dendron of claim 2, wherein the peptide dendron comprises branch points, generation 0 and successive generations and wherein the branch points, generation 0 and successive generations together comprise fewer than 100 amino acid residues.

4. The peptide dendron of claim 3, wherein the peptide dendron comprises a peptide dendron of formula (II):

$$(\{X_3\}\{X_2\}\{X_1\})_8(\{\mathbf{BP}\}\{X_3\}\{X_2\}\{X_1\})_4(\{\mathbf{BP}\}\{X_3\}\{X_2\}\{X_1\})_2\{\mathbf{BP}\} \quad \text{(II)}$$

wherein:

one of $X_1$, $X_2$, or $X_3$ in each ($\{X_3\}$ $\{X_2\}$ $\{X_1\}$), is a basic amino acid residue;

another $X_1$, $X_2$, or $X_3$ in each ($\{X_3\}$ $\{X_2\}$ $\{X_1\}$), is a hydrophobic amino acid residue;

the remaining $X_1$, $X_2$, or $X_3$ in each ($\{X_3\}$ $\{X_2\}$ $\{X_1\}$), is a residue derived from a modified lysine as defined in claim 1; and BP is a branch point amino acid residue.

5. The peptide dendron of claim 4, wherein the basic amino acid residue is arginine.

6. The peptide dendron of claim 4, wherein the hydrophobic amino acid residue is leucine.

7. The peptide dendron of claim 4, wherein each BP is lysine.

8. The peptide dendron of claim 4, further comprising a Generation 0 sequence of amino acid residues attached to the first branch point amino acid of the peptide dendron.

9. The peptide dendron of claim 8, wherein the Generation 0 sequence consists of GLY-VAL-CIT-GLY-GLY-SER-CYS (SEQ ID NO 5) wherein the terminal CYS carboxy group has been amidated to form a $C(O)NH_2$ group.

10. The peptide dendron of claim 4, further comprising a polyethylene glycol group consisting of $-(OCH_2CH_2)_n-$ repeating subunits where n>3.

11. The peptide dendron of claim 4, further comprising a targeting group selected from a peptide, antibody, sugar or small molecule targeting group.

12. A pharmaceutical composition which comprises one or more peptide dendrons of claim 1 and a pharmaceutically active agent.

13. The pharmaceutical composition of claim 12, wherein the pharmaceutically active agent is a genetic material selected from DNA and RNA.

14. A method of gene therapy which comprises administering to said animal an effective amount of the pharmaceutical composition of claim 12.

* * * * *